United States Patent
Jackson et al.

(10) Patent No.: US 9,522,021 B2
(45) Date of Patent: *Dec. 20, 2016

(54) POLYAXIAL BONE ANCHOR WITH RETAINER WITH NOTCH FOR MONO-AXIAL MOTION

(71) Applicant: Roger P. Jackson, Prairie Village, KS (US)

(72) Inventors: Roger P Jackson, Prairie Village, KS (US); James L Surber, Kansas City, KS (US)

(73) Assignee: Roger P. Jackson, Prairie Village, KS (US)

(*) Notice: Subject to any disclaimer, the term of this patent is extended or adjusted under 35 U.S.C. 154(b) by 0 days.

This patent is subject to a terminal disclaimer.

(21) Appl. No.: 14/674,517

(22) Filed: Mar. 31, 2015

(65) Prior Publication Data
US 2015/0257792 A1  Sep. 17, 2015

Related U.S. Application Data

(60) Continuation of application No. 13/694,110, filed on Oct. 26, 2012, now Pat. No. 9,168,069, and a
(Continued)

(51) Int. Cl.
*A61B 17/70* (2006.01)
*A61B 17/86* (2006.01)

(52) U.S. Cl.
CPC ....... *A61B 17/7037* (2013.01); *A61B 17/8605* (2013.01)

(58) Field of Classification Search
CPC ............ A61B 17/7008; A61B 17/7031; A61B 17/7032; A61B 17/7037; A61B 17/7076; A61B 17/8605; A61B 17/864
(Continued)

(56) References Cited

U.S. PATENT DOCUMENTS 154,864 A    9/1874  Harvey
791,548 A    6/1905  Fischer
(Continued)

FOREIGN PATENT DOCUMENTS

AU    2012203959    8/2012
DE        373809    4/1923
(Continued)

OTHER PUBLICATIONS

Brochure of Tyco/Healthcare/Surgical Dynamics on Spiral Radius 90D, Publication Date: Sep. 2001, pp. 1-8.
(Continued)

*Primary Examiner* — Pedro Philogene
*Assistant Examiner* — David C Comstock
(74) *Attorney, Agent, or Firm* — Polsinelli PC

(57) ABSTRACT

A polyaxial bone screw assembly includes a threaded shank body having an integral upper portion receivable in an integral receiver, the receiver having an upper channel for receiving a longitudinal connecting member and a lower cavity cooperating with a lower opening. A down-loadable compression insert having a sub-structure, a down-loadable friction fit split retaining ring having inner and outer tangs and an up-loadable shank upper portion cooperate to provide for pop- or snap-on assembly of the shank with the receiver either prior to or after implantation of the shank into a vertebra. The shank and receiver once assembled cannot be disassembled.

14 Claims, 18 Drawing Sheets

Related U.S. Application Data continuation-in-part of application No. 13/896,842, filed on May 17, 2013, which is a continuation of application No. 13/506,365, filed on Apr. 13, 2012, now Pat. No. 8,444,681, application No. 14/674,517, which is a continuation-in-part of application No. 14/482,562, filed on Sep. 10, 2014, which is a division of application No. 12/927,673, filed on Nov. 19, 2010, now Pat. No. 9,216,039, which is a continuation of application No. 11/328,481, filed on Jan. 9, 2006, now Pat. No. 7,862,587, which is a continuation-in-part of application No. 11/272,508, filed on Nov. 10, 2005, now Pat. No. 9,050,148, application No. 14/674,517, which is a continuation-in-part of application No. 13/573,874, filed on Oct. 10, 2012, application No. 14/674,517, which is a continuation-in-part of application No. 14/061,393, filed on Oct. 23, 2013, now abandoned, application No. 14/674,517, which is a continuation-in-part of application No. 13/573,516, filed on Sep. 19, 2012, application No. 14/674,517, which is a continuation-in-part of application No. 13/573,303, filed on Sep. 7, 2012, application No. 14/674,517, which is a continuation-in-part of application No. 13/506,365, filed on Apr. 13, 2012, now Pat. No. 8,444,681, application No. 14/674,517, which is a continuation-in-part of application No. 13/385,212, filed on Feb. 8, 2012, now Pat. No. 9,216,041, application No. 14/674,517, which is a continuation-in-part of application No. 13/374,439, filed on Dec. 29, 2011, and a continuation-in-part of application No. 13/373,289, filed on Nov. 9, 2011, application No. 14/674,517, which is a continuation-in-part of application No. 13/136,331, filed on Jul. 28, 2011, now abandoned, application No. 14/674,517, which is a continuation-in-part of application No. 12/924,802, filed on Oct. 5, 2010, now Pat. No. 8,556,938, application No. 14/674,517, which is a continuation-in-part of application No. 12/802,849, filed on Jun. 15, 2010.

(60) Provisional application No. 61/628,222, filed on Oct. 26, 2011, provisional application No. 61/517,088, filed on Apr. 13, 2011, provisional application No. 60/630,536, filed on Nov. 23, 2004, provisional application No. 61/627,374, filed on Oct. 11, 2011, provisional application No. 61/851,223, filed on Mar. 4, 2013, provisional application No. 61/795,984, filed on Oct. 31, 2012, provisional application No. 61/626,250, filed on Sep. 23, 2011, provisional application No. 61/573,508, filed on Sep. 7, 2011, provisional application No. 61/463,037, filed on Feb. 11, 2011, provisional application No. 61/456,649, filed on Nov. 10, 2010, provisional application No. 61/460,234, filed on Dec. 29, 2010, provisional application No. 61/400,504, filed on Jul. 29, 2010, provisional application No. 61/403,915, filed on Sep. 23, 2010, provisional application No. 61/278,240, filed on Oct. 5, 2009, provisional application No. 61/336,911, filed on Jan. 28, 2010, provisional application No. 61/343,737, filed on May 3, 2010, provisional application No. 61/395,564, filed on May 14, 2010, provisional application No. 61/395,752, filed on May 17, 2010, provisional application No. 61/396,390, filed on May 26, 2010, provisional application No. 61/398,807, filed on Jul. 1, 2010, provisional application No. 61/400,504, filed on Jul. 29, 2010, provisional application No. 61/402,959, filed on Sep. 8, 2010, provisional application No. 61/403,696, filed on Sep. 20, 2010, provisional application No. 61/403,915, filed on Sep. 23, 2010, provisional application No. 61/268,708, filed on Jun. 15, 2009, provisional application No. 61/270,754, filed on Jul. 13, 2009, provisional application No. 61/336,911, filed on Jan. 28, 2010, provisional application No. 61/395,564, filed on May 14, 2010, provisional application No. 61/395,752, filed on May 17, 2010, provisional application No. 61/396,390, filed on May 26, 2010.

(58) Field of Classification Search
USPC ........ 606/246, 264–270, 272–275, 279, 301, 606/305, 308, 328; 403/362; 411/393
See application file for complete search history.

(56) References Cited

U.S. PATENT DOCUMENTS

| | | |
|---|---|---|
| 1,300,275 A | 4/1919 | Johnson |
| 1,330,673 A | 2/1920 | Anderson |
| 1,472,464 A | 10/1923 | Ellison |
| 2,083,092 A | 6/1937 | Richer |
| 2,201,087 A | 5/1940 | Hallowell |
| 2,239,352 A | 4/1941 | Cherry |
| 2,243,717 A | 5/1941 | Moreira |
| 2,295,314 A | 9/1942 | Whitney |
| 2,346,346 A | 4/1944 | Anderson |
| 2,362,999 A | 11/1944 | Elmer |
| 2,445,978 A | 7/1948 | Stellin |
| 2,531,892 A | 11/1950 | Reese |
| 2,532,815 A | 12/1950 | Kindsvatter et al. |
| 2,537,029 A | 1/1951 | Cambern |
| 2,553,337 A | 5/1951 | Shafer |
| 2,778,265 A | 1/1957 | Brown |
| 2,813,450 A | 11/1957 | Dzus |
| 2,877,681 A | 3/1959 | Brown |
| 2,927,332 A | 3/1960 | Moore |
| 2,969,250 A | 1/1961 | Kull |
| 3,013,244 A | 12/1961 | Rudy |
| 3,143,029 A | 8/1964 | Brown |
| D200,217 S | 2/1965 | Curtiss |
| 3,236,275 A | 2/1966 | Smith |
| 3,370,341 A | 2/1968 | Allsop |
| 3,444,775 A | 5/1969 | Hills |
| 3,498,174 A | 3/1970 | Schuster et al. |
| 3,584,667 A | 6/1971 | Reiland |
| 3,604,487 A | 9/1971 | Gilbert |
| 3,640,416 A | 2/1972 | Temple |
| 3,812,757 A | 5/1974 | Reiland |
| 3,963,322 A | 6/1976 | Gryctko |
| 3,989,284 A | 11/1976 | Blose |
| 3,997,138 A | 12/1976 | Crock et al. |
| 4,013,071 A | 3/1977 | Rosenberg |
| 4,033,139 A | 7/1977 | Frederick |
| 4,041,939 A | 8/1977 | Hall |
| 4,103,422 A | 8/1978 | Weiss et al. |
| 4,190,091 A | 2/1980 | Colognori |
| 4,269,246 A | 5/1981 | Larson et al. |
| 4,323,326 A | 4/1982 | Okada et al. |
| 4,347,845 A | 9/1982 | Mayfield |
| 4,369,769 A | 1/1983 | Edwards |
| 4,373,754 A | 2/1983 | Bollfrass et al. |
| 4,409,968 A | 10/1983 | Drummond |
| 4,448,191 A | 5/1984 | Rodnyansky et al. |
| 4,484,570 A | 11/1984 | Sutter et al. |
| 4,492,500 A | 1/1985 | Ewing |
| 4,506,917 A | 3/1985 | Hansen |
| 4,577,448 A | 3/1986 | Howorth |
| 4,600,224 A | 7/1986 | Blose |
| 4,600,225 A | 7/1986 | Blose |
| 4,641,636 A | 2/1987 | Cotrel |

(56) References Cited

U.S. PATENT DOCUMENTS

| | | |
|---|---|---|
| 4,653,481 A | 3/1987 | Howland et al. |
| 4,653,486 A | 3/1987 | Coker |
| 4,703,954 A | 11/1987 | Ortloff et al. |
| 4,707,001 A | 11/1987 | Johnson |
| 4,743,260 A | 5/1988 | Burton |
| 4,748,260 A | 5/1988 | Marlett |
| 4,759,672 A | 7/1988 | Nilsen et al. |
| 4,763,644 A | 8/1988 | Webb |
| 4,764,068 A | 8/1988 | Crispell |
| 4,790,297 A | 12/1988 | Luque |
| 4,805,602 A | 2/1989 | Puno et al. |
| 4,815,453 A | 3/1989 | Cotrel |
| 4,836,196 A | 6/1989 | Park et al. |
| 4,838,264 A | 6/1989 | Bremer et al. |
| 4,850,775 A | 7/1989 | Lee et al. |
| 4,877,020 A | 10/1989 | Vich |
| 4,887,596 A | 12/1989 | Sherman |
| 4,917,606 A | 4/1990 | Miller |
| 4,946,458 A | 8/1990 | Harms et al. |
| 4,950,269 A | 8/1990 | Gaines, Jr. |
| 4,961,740 A | 10/1990 | Ray et al. |
| 5,005,562 A | 4/1991 | Cotrel |
| 5,019,080 A | 5/1991 | Hemer |
| 5,022,791 A | 6/1991 | Isler |
| 5,034,011 A | 7/1991 | Howland |
| 5,042,982 A | 8/1991 | Harms et al. |
| 5,056,492 A | 10/1991 | Banse |
| 5,067,428 A | 11/1991 | Dickerson et al. |
| 5,067,955 A | 11/1991 | Cotrel |
| 5,073,074 A | 12/1991 | Corrigan et al. |
| 5,084,048 A | 1/1992 | Jacob et al. |
| 5,092,635 A | 3/1992 | DeLange et al. |
| 5,102,412 A | 4/1992 | Rogozinski |
| 5,129,388 A | 7/1992 | Vignaud et al. |
| 5,129,899 A | 7/1992 | Small et al. |
| 5,147,360 A | 9/1992 | Dubousset |
| 5,147,363 A | 9/1992 | Harle |
| 5,154,719 A | 10/1992 | Cotrel |
| 5,176,483 A | 1/1993 | Baumann et al. |
| 5,176,678 A | 1/1993 | Tsou |
| 5,176,679 A | 1/1993 | Lin |
| 5,176,680 A | 1/1993 | Vignaud et al. |
| 5,180,393 A | 1/1993 | Commarmond |
| 5,201,734 A | 4/1993 | Cozad et al. |
| 5,207,678 A | 5/1993 | Harms et al. |
| 5,217,497 A | 6/1993 | Mehdian |
| 5,257,993 A | 11/1993 | Asher et al. |
| 5,261,907 A | 11/1993 | Vignaud et al. |
| 5,263,953 A | 11/1993 | Bagby |
| 5,275,601 A | 1/1994 | Gogolewski et al. |
| 5,282,707 A | 2/1994 | Palm |
| 5,282,862 A | 2/1994 | Barker et al. |
| 5,282,863 A | 2/1994 | Burton |
| 5,306,275 A | 4/1994 | Bryan |
| 5,312,404 A | 5/1994 | Asher et al. |
| 5,321,901 A | 6/1994 | Kelly |
| 5,330,472 A | 7/1994 | Metz-Stavenhagen |
| 5,334,203 A | 8/1994 | Wagner |
| 5,346,493 A | 9/1994 | Stahurski et al. |
| 5,354,292 A | 10/1994 | Braeuer et al. |
| 5,354,299 A | 10/1994 | Coleman |
| 5,358,289 A | 10/1994 | Banker et al. |
| 5,360,431 A | 11/1994 | Puno et al. |
| 5,364,400 A | 11/1994 | Rego, Jr. et al. |
| 5,375,823 A | 12/1994 | Navas |
| 5,382,248 A | 1/1995 | Jacobson et al. |
| 5,385,583 A | 1/1995 | Cotrel |
| 5,387,211 A | 2/1995 | Saadatmanesh et al. |
| 5,387,212 A | 2/1995 | Yuan et al. |
| 5,395,371 A | 3/1995 | Miller et al. |
| 5,409,488 A | 4/1995 | Ulrich |
| 5,409,489 A | 4/1995 | Sioufi |
| 5,415,661 A | 5/1995 | Holmes |
| 5,423,816 A | 6/1995 | Lin |
| 5,427,418 A | 6/1995 | Watts |
| 5,429,639 A | 7/1995 | Judet |
| 5,434,001 A | 7/1995 | Yamada et al. |
| 5,443,467 A | 8/1995 | Biedermann et al. |
| 5,466,237 A | 11/1995 | Byrd, III et al. |
| 5,466,238 A | 11/1995 | Lin |
| 5,468,241 A | 11/1995 | Metz-Stavenhagen et al. |
| 5,474,551 A | 12/1995 | Finn et al. |
| 5,474,555 A | 12/1995 | Puno et al. |
| 5,476,462 A | 12/1995 | Allard et al. |
| 5,476,464 A | 12/1995 | Metz-Stavenhagen et al. |
| 5,480,401 A | 1/1996 | Navas |
| 5,484,440 A | 1/1996 | Allard |
| 5,487,742 A | 1/1996 | Cotrel |
| 5,489,307 A | 2/1996 | Kuslich et al. |
| 5,490,750 A | 2/1996 | Gundy |
| 5,499,892 A | 3/1996 | Reed |
| 5,501,684 A | 3/1996 | Schlapfer et al. |
| 5,505,731 A | 4/1996 | Tornier |
| 5,507,745 A | 4/1996 | Logroscino et al. |
| 5,507,747 A | 4/1996 | Yuan et al. |
| 5,534,001 A | 7/1996 | Schlapfer et al. |
| 5,540,688 A | 7/1996 | Navas |
| 5,545,165 A | 8/1996 | Biedermann et al. |
| 5,549,607 A | 8/1996 | Olson et al. |
| 5,549,608 A | 8/1996 | Errico et al. |
| 5,554,157 A | 9/1996 | Errico et al. |
| 5,562,660 A | 10/1996 | Grob |
| 5,562,663 A | 10/1996 | Wisnewski et al. |
| 5,569,247 A | 10/1996 | Morrison |
| 5,569,251 A | 10/1996 | Baker et al. |
| 5,578,033 A | 11/1996 | Errico et al. |
| 5,584,834 A | 12/1996 | Errico et al. |
| 5,586,984 A | 12/1996 | Errico et al. |
| 5,591,166 A | 1/1997 | Bernhardt et al. |
| 5,601,553 A | 2/1997 | Trebing et al. |
| 5,605,458 A | 2/1997 | Bailey et al. |
| 5,607,304 A | 3/1997 | Bailey et al. |
| 5,607,425 A | 3/1997 | Rogozinski |
| 5,607,426 A | 3/1997 | Ralph et al. |
| 5,607,428 A | 3/1997 | Lin |
| 5,609,593 A | 3/1997 | Errico et al. |
| 5,609,594 A | 3/1997 | Errico et al. |
| 5,611,800 A | 3/1997 | Davis et al. |
| 5,628,740 A | 5/1997 | Mullane |
| 5,630,817 A | 5/1997 | Rokegem |
| 5,641,256 A | 6/1997 | Gundy |
| 5,643,260 A | 7/1997 | Doherty |
| 5,643,261 A | 7/1997 | Schafer et al. |
| 5,647,873 A | 7/1997 | Errico et al. |
| 5,653,710 A | 8/1997 | Harle |
| 5,662,652 A | 9/1997 | Schafer et al. |
| 5,662,653 A | 9/1997 | Songer et al. |
| 5,667,508 A | 9/1997 | Errico et al. |
| 5,669,909 A | 9/1997 | Zdeblick et al. |
| 5,669,911 A | 9/1997 | Errico et al. |
| 5,672,175 A | 9/1997 | Martin |
| 5,672,176 A | 9/1997 | Biedermann |
| 5,676,665 A | 10/1997 | Bryan |
| 5,676,703 A | 10/1997 | Gelbard |
| 5,681,319 A | 10/1997 | Biedermann et al. |
| 5,683,390 A | 11/1997 | Metz-Stavenhagen et al. |
| 5,683,391 A | 11/1997 | Boyd |
| 5,690,630 A | 11/1997 | Errico et al. |
| 5,702,393 A | 12/1997 | Pfaifer |
| 5,711,709 A | 1/1998 | McCoy |
| 5,713,705 A | 2/1998 | Grunbichler |
| 5,713,898 A | 2/1998 | Stuecker et al. |
| 5,716,356 A | 2/1998 | Biedermann et al. |
| 5,720,751 A | 2/1998 | Jackson |
| 5,723,013 A | 3/1998 | Jeanson et al. |
| 5,725,527 A | 3/1998 | Biedermann et al. |
| 5,725,528 A | 3/1998 | Errico et al. |
| 5,728,098 A | 3/1998 | Sherman et al. |
| 5,733,286 A | 3/1998 | Errico et al. |
| 5,738,685 A | 4/1998 | Halm et al. |
| 5,741,254 A | 4/1998 | Henry et al. |
| 5,752,957 A | 5/1998 | Ralph et al. |
| 5,782,833 A | 7/1998 | Haider |
| 5,797,911 A | 8/1998 | Sherman et al. |

(56) References Cited

U.S. PATENT DOCUMENTS

| | | |
|---|---|---|
| 5,800,435 A | 9/1998 | Errico et al. |
| 5,800,547 A | 9/1998 | Schaefer et al. |
| 5,817,094 A | 10/1998 | Errico et al. |
| 5,863,293 A | 1/1999 | Richelsoph |
| 5,873,878 A | 2/1999 | Harms et al. |
| D407,302 S | 3/1999 | Lawson |
| 5,876,402 A | 3/1999 | Errico et al. |
| 5,879,351 A | 3/1999 | Viart |
| 5,882,350 A | 3/1999 | Ralph et al. |
| 5,902,303 A | 5/1999 | Eckhof et al. |
| RE36,221 E | 6/1999 | Breard et al. |
| 5,910,141 A | 6/1999 | Morrison et al. |
| 5,910,142 A | 6/1999 | Tatar |
| 5,928,236 A | 7/1999 | Augagneur et al. |
| 5,938,663 A | 8/1999 | Petreto |
| 5,941,880 A | 8/1999 | Errico et al. |
| 5,944,465 A | 8/1999 | Janitzki |
| 5,951,553 A | 9/1999 | Betz et al. |
| 5,961,517 A | 10/1999 | Biedermann et al. |
| 5,964,760 A | 10/1999 | Richelsoph |
| 5,964,767 A | 10/1999 | Tapia et al. |
| 5,997,539 A | 12/1999 | Errico et al. |
| 6,001,098 A | 12/1999 | Metz-Stavenhagen et al. |
| 6,004,349 A | 12/1999 | Jackson |
| 6,010,503 A | 1/2000 | Richelsoph et al. |
| 6,019,759 A | 2/2000 | Rogozinski |
| 6,022,350 A | 2/2000 | Ganem |
| 6,053,078 A | 4/2000 | Parker |
| 6,056,753 A | 5/2000 | Jackson |
| 6,063,088 A | 5/2000 | Winslow |
| 6,074,391 A | 6/2000 | Metz-Stavenhagen et al. |
| 6,077,262 A | 6/2000 | Schlapfer et al. |
| 6,086,588 A | 7/2000 | Ameil et al. |
| 6,090,110 A | 7/2000 | Metz-Stavenhagen |
| 6,090,111 A | 7/2000 | Nichols |
| 6,099,528 A | 8/2000 | Saurat |
| 6,110,172 A | 8/2000 | Jackson |
| 6,113,601 A | 9/2000 | Tatar |
| 6,117,137 A | 9/2000 | Halm et al. |
| 6,129,763 A | 10/2000 | Chauvin et al. |
| 6,132,431 A | 10/2000 | Nilsson et al. |
| 6,136,002 A | 10/2000 | Shih et al. |
| 6,136,003 A | 10/2000 | Hoeck et al. |
| 6,139,549 A | 10/2000 | Keller |
| 6,143,032 A | 11/2000 | Schafer et al. |
| 6,146,383 A | 11/2000 | Studer et al. |
| 6,149,533 A | 11/2000 | Finn |
| 6,162,223 A | 12/2000 | Orsak et al. |
| 6,168,597 B1 | 1/2001 | Biedermann et al. |
| 6,224,596 B1 | 1/2001 | Jackson |
| 6,183,472 B1 | 2/2001 | Lutz |
| 6,186,718 B1 | 2/2001 | Fogard |
| 6,193,719 B1 | 2/2001 | Gournay et al. |
| 6,193,720 B1 | 2/2001 | Yuan et al. |
| 6,214,012 B1 | 4/2001 | Karpman et al. |
| RE37,161 E | 5/2001 | Michelson et al. |
| 6,224,598 B1 | 5/2001 | Jackson |
| 6,235,028 B1 | 5/2001 | Brumfield et al. |
| 6,235,034 B1 | 5/2001 | Bray |
| 6,241,730 B1 | 6/2001 | Alby |
| 6,241,731 B1 | 6/2001 | Fiz |
| 6,248,105 B1 | 6/2001 | Schlapfer et al. |
| 6,248,107 B1 | 6/2001 | Foley et al. |
| 6,251,112 B1 | 6/2001 | Jackson |
| 6,254,602 B1 | 7/2001 | Justis |
| 6,261,039 B1 | 7/2001 | Reed |
| 6,267,764 B1 | 7/2001 | Elberg |
| 6,267,765 B1 | 7/2001 | Taylor et al. |
| 6,280,445 B1 | 8/2001 | Morrison et al. |
| 6,287,308 B1 | 9/2001 | Betz et al. |
| 6,296,642 B1 | 10/2001 | Morrison et al. |
| 6,296,643 B1 | 10/2001 | Hopf et al. |
| 6,299,613 B1 | 10/2001 | Ogilvie et al. |
| 6,299,616 B1 | 10/2001 | Beger |
| 6,302,888 B1 | 10/2001 | Mellinger et al. |
| 6,309,391 B1 | 10/2001 | Crandall et al. |
| 6,315,564 B1 | 11/2001 | Levisman |
| 6,322,108 B1 | 11/2001 | Riesselmann et al. |
| RE37,665 E | 4/2002 | Ralph et al. |
| 6,368,321 B1 | 4/2002 | Jackson |
| 6,371,957 B1 | 4/2002 | Amrein |
| 6,379,356 B1 | 4/2002 | Jackson |
| 6,402,757 B1 | 6/2002 | Moore et al. |
| 6,440,133 B1 | 8/2002 | Beale et al. |
| 6,443,956 B1 | 9/2002 | Ray |
| 6,467,958 B1 | 10/2002 | Sasaki et al. |
| 6,471,703 B1 | 10/2002 | Ashman |
| 6,478,797 B1 | 11/2002 | Paul |
| 6,478,798 B1 | 11/2002 | Howland |
| 6,485,491 B1 | 11/2002 | Farris et al. |
| 6,485,492 B1 | 11/2002 | Halm et al. |
| 6,485,494 B1 | 11/2002 | Haider |
| 6,520,962 B1 | 2/2003 | Taylor et al. |
| 6,527,804 B1 | 3/2003 | Gauchet et al. |
| 6,533,786 B1 | 3/2003 | Needham et al. |
| 6,554,831 B1 | 4/2003 | Rivard et al. |
| 6,554,834 B1 | 4/2003 | Crozet et al. |
| 6,562,040 B1 | 5/2003 | Wagner |
| 6,565,565 B1 | 5/2003 | Yuan et al. |
| 6,565,567 B1 | 5/2003 | Haider |
| 6,595,992 B1 | 7/2003 | Wagner et al. |
| 6,602,255 B1 | 8/2003 | Campbell et al. |
| 6,613,050 B1 | 9/2003 | Wagner et al. |
| 6,616,667 B1 | 9/2003 | Steiger et al. |
| 6,648,885 B1 | 11/2003 | Friesem |
| 6,648,888 B1 | 11/2003 | Shluzas |
| 6,652,526 B1 | 11/2003 | Arafiles |
| 6,652,765 B1 | 11/2003 | Beaty |
| 6,656,179 B1 | 12/2003 | Schaefer et al. |
| 6,663,632 B1 | 12/2003 | Frigg |
| 6,673,073 B1 | 1/2004 | Schaefer |
| 6,676,661 B1 | 1/2004 | Benlloch et al. |
| 6,712,818 B1 | 3/2004 | Michelson |
| 6,716,214 B1 | 4/2004 | Jackson |
| 6,743,231 B1 | 6/2004 | Gray et al. |
| 6,755,829 B1 | 6/2004 | Bono et al. |
| 6,778,861 B1 | 8/2004 | Liebrecht et al. |
| 6,835,196 B2 | 12/2004 | Biedermann et al. |
| 6,872,208 B1 | 3/2005 | McBride et al. |
| 6,896,677 B1 | 5/2005 | Lin |
| 7,001,389 B1 | 2/2006 | Navarro et al. |
| RE39,035 E | 3/2006 | Finn et al. |
| RE39,089 E | 5/2006 | Ralph et al. |
| 7,081,116 B1 | 7/2006 | Carly |
| 7,179,261 B2 | 2/2007 | Sicvol et al. |
| 7,316,684 B1 | 1/2008 | Baccelli et al. |
| 7,625,394 B2 | 12/2009 | Molz, IV et al. |
| 7,686,833 B1 | 3/2010 | Muhanna et al. |
| 7,766,941 B2 | 8/2010 | Paul |
| 7,766,943 B1 | 8/2010 | Fallin et al. |
| 7,833,251 B1 | 11/2010 | Ahlgren et al. |
| 7,862,587 B2 | 1/2011 | Jackson |
| 7,947,065 B2 | 5/2011 | Hammill, Sr. et al. |
| 7,972,364 B2 | 7/2011 | Biedermann et al. |
| 8,043,340 B1 | 10/2011 | Law |
| 8,092,499 B1 | 1/2012 | Roth |
| 8,114,133 B2 | 2/2012 | Logan |
| 8,114,134 B2 | 2/2012 | Winslow et al. |
| 8,133,262 B2 | 3/2012 | Whipple |
| 8,167,914 B1 | 5/2012 | Hunt et al. |
| 8,197,517 B1 | 6/2012 | Lab et al. |
| 8,206,422 B2 | 6/2012 | Hestad et al. |
| 8,211,110 B1 | 7/2012 | Corin et al. |
| 8,236,035 B1 | 8/2012 | Bedor |
| 8,388,659 B1 | 3/2013 | Lab et al. |
| 8,394,133 B2 | 3/2013 | Jackson |
| 8,439,922 B1 | 5/2013 | Arnold et al. |
| 8,439,924 B1 | 5/2013 | McBride et al. |
| 8,444,681 B2 | 5/2013 | Jackson et al. |
| 8,470,009 B1 | 6/2013 | Rezach |
| 8,500,780 B2 | 8/2013 | Petit et al. |
| 9,168,069 B2 * | 10/2015 | Jackson ............ A61B 17/7037 |
| 2001/0007941 A1 | 7/2001 | Steiner et al. |
| 2001/0010000 A1 | 7/2001 | Gertzbein et al. |

(56) References Cited

U.S. PATENT DOCUMENTS

| | | |
|---|---|---|
| 2001/0011172 A1 | 8/2001 | Orbay et al. |
| 2001/0012937 A1 | 8/2001 | Schaffler-Wachter et al. |
| 2001/0023350 A1 | 9/2001 | Choi |
| 2001/0037111 A1 | 11/2001 | Dixon et al. |
| 2001/0041894 A1 | 11/2001 | Campbell et al. |
| 2001/0047173 A1 | 11/2001 | Schlapfer et al. |
| 2001/0047174 A1 | 11/2001 | Donno et al. |
| 2001/0047175 A1 | 11/2001 | Doubler et al. |
| 2001/0052438 A1 | 12/2001 | Spencer |
| 2002/0004683 A1 | 1/2002 | Michelson |
| 2002/0007184 A1 | 1/2002 | Ogilvie et al. |
| 2002/0010467 A1 | 1/2002 | Cooper et al. |
| 2002/0013586 A1 | 1/2002 | Justis et al. |
| 2002/0016594 A1 | 2/2002 | Schlapfer et al. |
| 2002/0022764 A1 | 2/2002 | Smith et al. |
| 2002/0022842 A1 | 2/2002 | Horvath et al. |
| 2002/0029040 A1 | 3/2002 | Morrison et al. |
| 2002/0035365 A1 | 3/2002 | Kumar et al. |
| 2002/0035366 A1 | 3/2002 | Walder et al. |
| 2002/0035367 A1 | 3/2002 | Ritland |
| 2002/0045898 A1 | 4/2002 | Freid et al. |
| 2002/0045899 A1 | 4/2002 | Errico et al. |
| 2002/0049446 A1 | 4/2002 | Harkey, III et al. |
| 2002/0055740 A1 | 5/2002 | Lieberman |
| 2002/0055741 A1 | 5/2002 | Schlapfer et al. |
| 2002/0058942 A1 | 5/2002 | Biedermann et al. |
| 2002/0068975 A1 | 6/2002 | Teitelbaum et al. |
| 2002/0072750 A1 | 6/2002 | Jackson |
| 2002/0072751 A1 | 6/2002 | Jackson |
| 2002/0082602 A1 | 6/2002 | Biedermann et al. |
| 2002/0082603 A1 | 6/2002 | Dixon et al. |
| 2002/0087159 A1 | 7/2002 | Thomas |
| 2002/0087161 A1 | 7/2002 | Randall et al. |
| 2002/0091386 A1 | 7/2002 | Martin et al. |
| 2002/0095153 A1 | 7/2002 | Jones et al. |
| 2002/0095154 A1 | 7/2002 | Atkinson et al. |
| 2002/0095881 A1 | 7/2002 | Shreiner |
| 2002/0103487 A1 | 8/2002 | Errico et al. |
| 2002/0111627 A1 | 8/2002 | Vincent-Prestigiacomo |
| 2002/0116001 A1 | 8/2002 | Schafer et al. |
| 2002/0120270 A1 | 8/2002 | Trieu et al. |
| 2002/0123752 A1 | 9/2002 | Schultheiss et al. |
| 2002/0133154 A1 | 9/2002 | Saint Martin |
| 2002/0133158 A1 | 9/2002 | Saint Martin |
| 2002/0133159 A1 | 9/2002 | Jackson |
| 2002/0138076 A1 | 9/2002 | Biedermann et al. |
| 2002/0138077 A1 | 9/2002 | Ferree |
| 2002/0143328 A1 | 10/2002 | Shluzas et al. |
| 2002/0143330 A1 | 10/2002 | Shluzas |
| 2002/0143332 A1 | 10/2002 | Lin et al. |
| 2002/0143338 A1 | 10/2002 | Orbay et al. |
| 2002/0143341 A1 | 10/2002 | Biedermann et al. |
| 2002/0161368 A1 | 10/2002 | Foley et al. |
| 2002/0161370 A1 | 10/2002 | Frigg et al. |
| 2002/0173791 A1 | 11/2002 | Howland |
| 2002/0183747 A1 | 12/2002 | Jao et al. |
| 2002/0198526 A1 | 12/2002 | Shaolian et al. |
| 2003/0004519 A1 | 1/2003 | Torode et al. |
| 2003/0023243 A1 | 1/2003 | Biedermann et al. |
| 2003/0028191 A1 | 2/2003 | Shluzas |
| 2003/0032957 A1 | 2/2003 | McKinley |
| 2003/0055426 A1 | 3/2003 | Carbone et al. |
| 2003/0055427 A1 | 3/2003 | Graf |
| 2003/0060826 A1 | 3/2003 | Foley et al. |
| 2003/0073995 A1 | 4/2003 | Reed |
| 2003/0073996 A1 | 4/2003 | Doubler et al. |
| 2003/0073998 A1 | 4/2003 | Pagliuca et al. |
| 2003/0078580 A1 | 4/2003 | Shitoto |
| 2003/0083657 A1 | 5/2003 | Drewry et al. |
| 2003/0083667 A1 | 5/2003 | Ralph et al. |
| 2003/0093077 A1 | 5/2003 | Schlapfer et al. |
| 2003/0093078 A1 | 5/2003 | Ritland |
| 2003/0100896 A1 | 5/2003 | Biedermann et al. |
| 2003/0100897 A1 | 5/2003 | Metz-Stavenhagen |
| 2003/0100904 A1 | 5/2003 | Biedermann |
| 2003/0105460 A1 | 6/2003 | Crandall et al. |
| 2003/0109880 A1 | 6/2003 | Shirado et al. |
| 2003/0114852 A1 | 6/2003 | Biedermann et al. |
| 2003/0120275 A1 | 6/2003 | Lenke et al. |
| 2003/0125741 A1 | 7/2003 | Biedermann et al. |
| 2003/0125749 A1 | 7/2003 | Yuan et al. |
| 2003/0130659 A1 | 7/2003 | Haider |
| 2003/0130661 A1 | 7/2003 | Osman |
| 2003/0135210 A1 | 7/2003 | Dixon et al. |
| 2003/0135217 A1 | 7/2003 | Buttermann et al. |
| 2003/0139745 A1 | 7/2003 | Ashman |
| 2003/0149430 A1 | 8/2003 | Ferrante et al. |
| 2003/0149431 A1 | 8/2003 | Varieur |
| 2003/0149432 A1 | 8/2003 | Frigg et al. |
| 2003/0149435 A1 | 8/2003 | Baynham et al. |
| 2003/0153911 A1 | 8/2003 | Shluzas |
| 2003/0153912 A1 | 8/2003 | Graf |
| 2003/0153920 A1 | 8/2003 | Ralph et al. |
| 2003/0163133 A1 | 8/2003 | Altarac et al. |
| 2003/0167058 A1 | 9/2003 | Shluzas |
| 2003/0171749 A1 | 9/2003 | Le Couedic et al. |
| 2003/0176863 A1 | 9/2003 | Ueyama et al. |
| 2003/0181913 A1 | 9/2003 | Lieberman |
| 2003/0187433 A1 | 10/2003 | Lin |
| 2003/0187434 A1 | 10/2003 | Lin |
| 2003/0191470 A1 | 10/2003 | Ritland |
| 2003/0199872 A1 | 10/2003 | Markworth et al. |
| 2003/0199873 A1 | 10/2003 | Richelsoph |
| 2003/0208204 A1 | 11/2003 | Bailey et al. |
| 2003/0212398 A1 | 11/2003 | Jackson |
| 2003/0216735 A1 | 11/2003 | Altarac et al. |
| 2003/0220642 A1 | 11/2003 | Freudiger |
| 2003/0220643 A1 | 11/2003 | Ferree |
| 2003/0225408 A1 | 12/2003 | Nichols et al. |
| 2003/0229345 A1 | 12/2003 | Stahurski |
| 2003/0229347 A1 | 12/2003 | Sherman et al. |
| 2003/0236529 A1 | 12/2003 | Shluzas et al. |
| 2004/0006342 A1 | 1/2004 | Altarac et al. |
| 2004/0039383 A1 | 2/2004 | Jackson |
| 2004/0039384 A1 | 2/2004 | Boehm, Jr. et al. |
| 2004/0039385 A1 | 2/2004 | Mazda et al. |
| 2004/0049189 A1 | 3/2004 | Le Couedic et al. |
| 2004/0049190 A1 | 3/2004 | Biedermann et al. |
| 2004/0073215 A1 | 4/2004 | Carli |
| 2004/0073218 A1 | 4/2004 | Dahners |
| 2004/0078051 A1 | 4/2004 | Davison et al. |
| 2004/0078082 A1 | 4/2004 | Lange |
| 2004/0087949 A1 | 5/2004 | Bono et al. |
| 2004/0087950 A1 | 5/2004 | Teitelbaum |
| 2004/0087952 A1 | 5/2004 | Borgstrom et al. |
| 2004/0092934 A1 | 5/2004 | Howland |
| 2004/0092938 A1 | 5/2004 | Carli |
| 2004/0097933 A1 | 5/2004 | Lourdel et al. |
| 2004/0106925 A1 | 6/2004 | Culbert |
| 2004/0111091 A1 | 6/2004 | Ogilvie et al. |
| 2004/0122442 A1 | 6/2004 | Lewis |
| 2004/0127897 A1 | 7/2004 | Freid et al. |
| 2004/0127904 A1 | 7/2004 | Konieczynski et al. |
| 2004/0133207 A1 | 7/2004 | Abdou |
| 2004/0138660 A1 | 7/2004 | Serhan |
| 2004/0138662 A1 | 7/2004 | Landry et al. |
| 2004/0143265 A1 | 7/2004 | Landry et al. |
| 2004/0147928 A1 | 7/2004 | Landry et al. |
| 2004/0147929 A1 | 7/2004 | Biedermann et al. |
| 2004/0147937 A1 | 7/2004 | Dunbar, Jr. et al. |
| 2004/0153068 A1 | 8/2004 | Janowski et al. |
| 2004/0158245 A1 | 8/2004 | Chin |
| 2004/0158247 A1 | 8/2004 | Sitiso et al. |
| 2004/0158258 A1 | 8/2004 | Bonati et al. |
| 2004/0162560 A1 | 8/2004 | Raynor et al. |
| 2004/0167523 A1 | 8/2004 | Jackson |
| 2004/0167525 A1 | 8/2004 | Jackson |
| 2004/0172025 A1 | 9/2004 | Drewry et al. |
| 2004/0172031 A1 | 9/2004 | Rubecamp et al. |
| 2004/0172032 A1 | 9/2004 | Jackson |
| 2004/0176776 A1 | 9/2004 | Zubok et al. |
| 2004/0186473 A1 | 9/2004 | Cournoyer et al. |
| 2004/0186474 A1 | 9/2004 | Matthis et al. |
| 2004/0186475 A1 | 9/2004 | Falahee |

(56) References Cited

U.S. PATENT DOCUMENTS

| | | |
|---|---|---|
| 2004/0210216 A1 | 10/2004 | Farris et al. |
| 2004/0210227 A1 | 10/2004 | Trail et al. |
| 2004/0215190 A1 | 10/2004 | Nguyen et al. |
| 2004/0215191 A1 | 10/2004 | Kitchen |
| 2004/0220567 A1 | 11/2004 | Eisermann et al. |
| 2004/0220671 A1 | 11/2004 | Ralph et al. |
| 2004/0225289 A1 | 11/2004 | Biedermann et al. |
| 2004/0230100 A1 | 11/2004 | Shluzas |
| 2004/0236327 A1 | 11/2004 | Paul et al. |
| 2004/0236328 A1 | 11/2004 | Paul et al. |
| 2004/0236330 A1 | 11/2004 | Purcell et al. |
| 2004/0249378 A1 | 12/2004 | Saint Martin et al. |
| 2004/0254574 A1 | 12/2004 | Morrison et al. |
| 2004/0260283 A1 | 12/2004 | Wu et al. |
| 2004/0267264 A1 | 12/2004 | Konieczynski et al. |
| 2005/0010219 A1 | 1/2005 | Dalton |
| 2005/0010220 A1 | 1/2005 | Casutt et al. |
| 2005/0021036 A1 | 1/2005 | Whitemore et al. |
| 2005/0027296 A1 | 2/2005 | Thramann et al. |
| 2005/0033298 A1 | 2/2005 | Hawkes et al. |
| 2005/0033436 A1 | 2/2005 | Schlapfer et al. |
| 2005/0033439 A1 | 2/2005 | Gordon et al. |
| 2005/0038430 A1 | 2/2005 | McKinley |
| 2005/0038432 A1 | 2/2005 | Shaolian et al. |
| 2005/0038433 A1 | 2/2005 | Young |
| 2005/0049588 A1 | 3/2005 | Jackson |
| 2005/0049589 A1 | 3/2005 | Jackson |
| 2005/0055026 A1 | 3/2005 | Biedermann et al. |
| 2005/0065514 A1 | 3/2005 | Studer |
| 2005/0065515 A1 | 3/2005 | Jahng |
| 2005/0065516 A1 | 3/2005 | Jahng |
| 2005/0065517 A1 | 3/2005 | Chin |
| 2005/0070899 A1 | 3/2005 | Doubler et al. |
| 2005/0070901 A1 | 3/2005 | David |
| 2005/0080415 A1 | 4/2005 | Keyer et al. |
| 2005/0085812 A1 | 4/2005 | Sherman et al. |
| 2005/0085813 A1 | 4/2005 | Spitler et al. |
| 2005/0085815 A1 | 4/2005 | Harms et al. |
| 2005/0085816 A1 | 4/2005 | Michelson |
| 2005/0090821 A1 | 4/2005 | Berrevoets et al. |
| 2005/0096652 A1 | 5/2005 | Burton |
| 2005/0096653 A1 | 5/2005 | Doubler et al. |
| 2005/0096654 A1 | 5/2005 | Lin |
| 2005/0107788 A1 | 5/2005 | Beaurain et al. |
| 2005/0113927 A1 | 5/2005 | Malek |
| 2005/0119658 A1 | 6/2005 | Ralph et al. |
| 2005/0124991 A1 | 6/2005 | Jahng |
| 2005/0131404 A1 | 6/2005 | Mazda et al. |
| 2005/0131405 A1 | 6/2005 | Molz, IV et al. |
| 2005/0131406 A1 | 6/2005 | Reiley et al. |
| 2005/0131407 A1 | 6/2005 | Sicvol et al. |
| 2005/0131408 A1 | 6/2005 | Sicvol et al. |
| 2005/0131413 A1 | 6/2005 | O'Driscoll et al. |
| 2005/0131419 A1 | 6/2005 | McCord et al. |
| 2005/0131421 A1 | 6/2005 | Anderson et al. |
| 2005/0131422 A1 | 6/2005 | Anderson |
| 2005/0137594 A1 | 6/2005 | Doubler et al. |
| 2005/0137597 A1 | 6/2005 | Butler et al. |
| 2005/0141986 A1 | 6/2005 | Flesher |
| 2005/0143737 A1 | 6/2005 | Pafford et al. |
| 2005/0143823 A1 | 6/2005 | Boyd et al. |
| 2005/0149020 A1 | 7/2005 | Jahng |
| 2005/0149053 A1 | 7/2005 | Varieur |
| 2005/0154389 A1 | 7/2005 | Selover et al. |
| 2005/0154390 A1 | 7/2005 | Biedermann et al. |
| 2005/0154391 A1 | 7/2005 | Doherty et al. |
| 2005/0159750 A1 | 7/2005 | Doherty |
| 2005/0165400 A1 | 7/2005 | Fernandez |
| 2005/0171540 A1 | 8/2005 | Lim et al. |
| 2005/0171543 A1 | 8/2005 | Timm et al. |
| 2005/0177154 A1 | 8/2005 | Moumene et al. |
| 2005/0177166 A1 | 8/2005 | Timm et al. |
| 2005/0182401 A1 | 8/2005 | Timm et al. |
| 2005/0182410 A1 | 8/2005 | Jackson |
| 2005/0187548 A1 | 8/2005 | Butler et al. |
| 2005/0187555 A1 | 8/2005 | Biedermann et al. |
| 2005/0192571 A1 | 9/2005 | Abdelgany |
| 2005/0192572 A1 | 9/2005 | Abdelgany et al. |
| 2005/0192573 A1 | 9/2005 | Abdelgany et al. |
| 2005/0192579 A1 | 9/2005 | Jackson |
| 2005/0192580 A1 | 9/2005 | Dalton |
| 2005/0192589 A1 | 9/2005 | Raymond et al. |
| 2005/0203511 A1 | 9/2005 | Wilson-MacDonald et al. |
| 2005/0203513 A1 | 9/2005 | Jahng et al. |
| 2005/0203514 A1 | 9/2005 | Jahng et al. |
| 2005/0203516 A1 | 9/2005 | Harms et al. |
| 2005/0203518 A1 | 9/2005 | Biedermann et al. |
| 2005/0203519 A1 | 9/2005 | Harms et al. |
| 2005/0215999 A1 | 9/2005 | Birkmeyer et al. |
| 2005/0216000 A1 | 9/2005 | Colleran et al. |
| 2005/0216001 A1 | 9/2005 | David |
| 2005/0216003 A1 | 9/2005 | Biedermann et al. |
| 2005/0228326 A1 | 10/2005 | Kalfas et al. |
| 2005/0228379 A1 | 10/2005 | Jackson |
| 2005/0228385 A1 | 10/2005 | Lee et al. |
| 2005/0228400 A1 | 10/2005 | Chao |
| 2005/0228501 A1 | 10/2005 | Miller et al. |
| 2005/0234450 A1 | 10/2005 | Barker |
| 2005/0234451 A1 | 10/2005 | Markworth |
| 2005/0234452 A1 | 10/2005 | Malandain |
| 2005/0234453 A1 | 10/2005 | Shaolian et al. |
| 2005/0234454 A1 | 10/2005 | Chin |
| 2005/0234456 A1 | 10/2005 | Malandain |
| 2005/0234459 A1 | 10/2005 | Falahee et al. |
| 2005/0240181 A1 | 10/2005 | Boomer et al. |
| 2005/0240183 A1 | 10/2005 | Vaughan |
| 2005/0245930 A1 | 11/2005 | Timm et al. |
| 2005/0251137 A1 | 11/2005 | Ball |
| 2005/0251139 A1 | 11/2005 | Roh |
| 2005/0251140 A1 | 11/2005 | Shaolian et al. |
| 2005/0251141 A1 | 11/2005 | Frigg et al. |
| 2005/0260058 A1 | 11/2005 | Cassagne, III |
| 2005/0261687 A1 | 11/2005 | Garamszegi et al. |
| 2005/0267470 A1 | 12/2005 | McBride |
| 2005/0267471 A1 | 12/2005 | Biedermann et al. |
| 2005/0267472 A1 | 12/2005 | Biedermann et al. |
| 2005/0267474 A1 | 12/2005 | Dalton |
| 2005/0267477 A1 | 12/2005 | Jackson |
| 2005/0273099 A1 | 12/2005 | Baccelli et al. |
| 2005/0273101 A1 | 12/2005 | Schumacher |
| 2005/0277919 A1 | 12/2005 | Slivka et al. |
| 2005/0277922 A1 | 12/2005 | Trieu et al. |
| 2005/0277923 A1 | 12/2005 | Sweeney |
| 2005/0277925 A1 | 12/2005 | Mujwid |
| 2005/0277927 A1 | 12/2005 | Guenther et al. |
| 2005/0277928 A1 | 12/2005 | Boschert |
| 2005/0277931 A1 | 12/2005 | Sweeney et al. |
| 2005/0277934 A1 | 12/2005 | Vardiman |
| 2005/0278023 A1 | 12/2005 | Zwirkoski |
| 2005/0283152 A1 | 12/2005 | Lindemann et al. |
| 2005/0283157 A1 | 12/2005 | Coates et al. |
| 2005/0283238 A1 | 12/2005 | Reiley |
| 2005/0283244 A1 | 12/2005 | Gordon et al. |
| 2005/0288669 A1 | 12/2005 | Abdou |
| 2005/0288670 A1 | 12/2005 | Panjabi |
| 2005/0288672 A1 | 12/2005 | Ferree |
| 2005/0288673 A1 | 12/2005 | Catbagan et al. |
| 2006/0004359 A1 | 1/2006 | Kramer et al. |
| 2006/0004363 A1 | 1/2006 | Brockmeyer et al. |
| 2006/0009767 A1 | 1/2006 | Kiester |
| 2006/0009769 A1 | 1/2006 | Lieberman |
| 2006/0009770 A1 | 1/2006 | Speirs et al. |
| 2006/0009780 A1 | 1/2006 | Foley et al. |
| 2006/0015099 A1 | 1/2006 | Cannon et al. |
| 2006/0025767 A1 | 2/2006 | Khalili |
| 2006/0025768 A1 | 2/2006 | Iott et al. |
| 2006/0025770 A1 | 2/2006 | Schlapfer et al. |
| 2006/0025771 A1 | 2/2006 | Jackson |
| 2006/0030850 A1 | 2/2006 | Keegan et al. |
| 2006/0036240 A1 | 2/2006 | Colleran et al. |
| 2006/0036242 A1 | 2/2006 | Nilsson et al. |
| 2006/0036243 A1 | 2/2006 | Sasso et al. |
| 2006/0036244 A1 | 2/2006 | Spitler et al. |
| 2006/0036246 A1 | 2/2006 | Carl et al. |

(56) References Cited

U.S. PATENT DOCUMENTS

| | | |
|---|---|---|
| 2006/0036252 A1 | 2/2006 | Baynham et al. |
| 2006/0036254 A1 | 2/2006 | Lim |
| 2006/0036256 A1 | 2/2006 | Carl et al. |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0052780 A1 | 3/2006 | Errico et al. |
| 2006/0052783 A1 | 3/2006 | Dant et al. |
| 2006/0052784 A1 | 3/2006 | Dant et al. |
| 2006/0052786 A1 | 3/2006 | Dant et al. |
| 2006/0058788 A1 | 3/2006 | Hammer et al. |
| 2006/0058790 A1 | 3/2006 | Carl et al. |
| 2006/0064090 A1 | 3/2006 | Park |
| 2006/0064091 A1 | 3/2006 | Ludwig et al. |
| 2006/0064092 A1 | 3/2006 | Howland |
| 2006/0069390 A1 | 3/2006 | Frigg et al. |
| 2006/0074418 A1 | 4/2006 | Jackson |
| 2006/0074419 A1 | 4/2006 | Taylor et al. |
| 2006/0079894 A1 | 4/2006 | Colleran et al. |
| 2006/0079895 A1 | 4/2006 | McLeer |
| 2006/0079896 A1 | 4/2006 | Kwak et al. |
| 2006/0079898 A1 | 4/2006 | Ainsworth |
| 2006/0079899 A1 | 4/2006 | Ritland |
| 2006/0084977 A1 | 4/2006 | Lieberman |
| 2006/0084980 A1 | 4/2006 | Melkent et al. |
| 2006/0084981 A1 | 4/2006 | Shluzas |
| 2006/0084982 A1 | 4/2006 | Kim |
| 2006/0084983 A1 | 4/2006 | Kim |
| 2006/0084984 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0084989 A1 | 4/2006 | Dickinson et al. |
| 2006/0084991 A1 | 4/2006 | Borgstrom et al. |
| 2006/0085069 A1 | 4/2006 | Kim |
| 2006/0085070 A1 | 4/2006 | Kim |
| 2006/0089643 A1 | 4/2006 | Mujwid |
| 2006/0089644 A1 | 4/2006 | Felix |
| 2006/0089645 A1 | 4/2006 | Eckman |
| 2006/0095035 A1 | 5/2006 | Jones et al. |
| 2006/0095037 A1 | 5/2006 | Jones et al. |
| 2006/0095038 A1 | 5/2006 | Jackson |
| 2006/0100621 A1 | 5/2006 | Jackson |
| 2006/0100622 A1 | 5/2006 | Jackson |
| 2006/0106381 A1 | 5/2006 | Ferree et al. |
| 2006/0106394 A1 | 5/2006 | Colleran |
| 2006/0111713 A1 | 5/2006 | Jackson |
| 2006/0111715 A1 | 5/2006 | Jackson |
| 2006/0116677 A1 | 6/2006 | Burd et al. |
| 2006/0122597 A1 | 6/2006 | Jones et al. |
| 2006/0122599 A1 | 6/2006 | Drewry et al. |
| 2006/0129147 A1 | 6/2006 | Biedermann et al. |
| 2006/0129149 A1 | 6/2006 | Iott et al. |
| 2006/0129239 A1 | 6/2006 | Kwak |
| 2006/0142758 A1 | 6/2006 | Petit |
| 2006/0142760 A1 | 6/2006 | McDonnell |
| 2006/0149228 A1 | 7/2006 | Schlapfer et al. |
| 2006/0149229 A1 | 7/2006 | Kwak et al. |
| 2006/0149232 A1 | 7/2006 | Sasing |
| 2006/0149235 A1 | 7/2006 | Jackson |
| 2006/0149238 A1 | 7/2006 | Sherman et al. |
| 2006/0149240 A1 | 7/2006 | Jackson |
| 2006/0149241 A1 | 7/2006 | Richelsoph et al. |
| 2006/0149251 A1 | 7/2006 | Ziolo et al. |
| 2006/0155277 A1 | 7/2006 | Metz-Stavenhagen |
| 2006/0161152 A1 | 7/2006 | Ensign et al. |
| 2006/0166535 A1 | 7/2006 | Brumfield et al. |
| 2006/0167454 A1 | 7/2006 | Ludwig et al. |
| 2006/0167455 A1 | 7/2006 | Clement et al. |
| 2006/0173454 A1 | 8/2006 | Spitler et al. |
| 2006/0173456 A1 | 8/2006 | Hawkes et al. |
| 2006/0184171 A1 | 8/2006 | Biedermann |
| 2006/0184180 A1 | 8/2006 | Augostino |
| 2006/0189983 A1 | 8/2006 | Fallin et al. |
| 2006/0189985 A1 | 8/2006 | Lewis |
| 2006/0195090 A1 | 8/2006 | Suddaby |
| 2006/0195093 A1 | 8/2006 | Jahng |
| 2006/0195198 A1 | 8/2006 | James |
| 2006/0200023 A1 | 9/2006 | Melkent et al. |
| 2006/0200128 A1 | 9/2006 | Mueller |
| 2006/0200130 A1 | 9/2006 | Hawkins et al. |
| 2006/0200131 A1 | 9/2006 | Chao et al. |
| 2006/0200132 A1 | 9/2006 | Chao et al. |
| 2006/0200133 A1 | 9/2006 | Jackson |
| 2006/0200149 A1 | 9/2006 | Hoy et al. |
| 2006/0212033 A1 | 9/2006 | Rothman et al. |
| 2006/0212034 A1 | 9/2006 | Triplett et al. |
| 2006/0217713 A1 | 9/2006 | Serhan et al. |
| 2006/0217716 A1 | 9/2006 | Baker et al. |
| 2006/0217719 A1 | 9/2006 | Albert et al. |
| 2006/0229608 A1 | 10/2006 | Foster et al. |
| 2006/0229609 A1 | 10/2006 | Wang |
| 2006/0229613 A1 | 10/2006 | Timm |
| 2006/0229614 A1 | 10/2006 | Foley et al. |
| 2006/0229615 A1 | 10/2006 | Abdou |
| 2006/0241593 A1 | 10/2006 | Sherman et al. |
| 2006/0241595 A1 | 10/2006 | Molz, IV et al. |
| 2006/0241599 A1 | 10/2006 | Konieczynski |
| 2006/0241600 A1 | 10/2006 | Ensign et al. |
| 2006/0241601 A1 | 10/2006 | Trautwein et al. |
| 2006/0241603 A1 | 10/2006 | Jackson |
| 2006/0247624 A1 | 11/2006 | Banouskou et al. |
| 2006/0247630 A1 | 11/2006 | Iott et al. |
| 2006/0247631 A1 | 11/2006 | Ahn et al. |
| 2006/0247632 A1 | 11/2006 | Winslow et al. |
| 2006/0247633 A1 | 11/2006 | Winslow et al. |
| 2006/0247635 A1 | 11/2006 | Gordon et al. |
| 2006/0247658 A1 | 11/2006 | Pond, Jr. et al. |
| 2006/0247779 A1 | 11/2006 | Gordon |
| 2006/0260483 A1 | 11/2006 | Hartmann et al. |
| 2006/0264933 A1 | 11/2006 | Baker et al. |
| 2006/0264934 A1 | 11/2006 | Fallin |
| 2006/0264935 A1 | 11/2006 | White |
| 2006/0264936 A1 | 11/2006 | Partin et al. |
| 2006/0264962 A1 | 11/2006 | Chin et al. |
| 2006/0271047 A1 | 11/2006 | Jackson |
| 2006/0276787 A1 | 12/2006 | Zubok et al. |
| 2006/0276789 A1 | 12/2006 | Jackson |
| 2006/0276791 A1 | 12/2006 | Shluzas |
| 2006/0276792 A1 | 12/2006 | Ensign et al. |
| 2006/0282075 A1 | 12/2006 | Labrom et al. |
| 2006/0282076 A1 | 12/2006 | Labrom et al. |
| 2006/0282077 A1 | 12/2006 | Labrom et al. |
| 2006/0282078 A1 | 12/2006 | Labrom et al. |
| 2006/0282079 A1 | 12/2006 | Labrom et al. |
| 2006/0282080 A1 | 12/2006 | Albert |
| 2006/0293657 A1 | 12/2006 | Hartmann |
| 2006/0293659 A1 | 12/2006 | Alvarez |
| 2006/0293663 A1 | 12/2006 | Walkenhorst |
| 2006/0293666 A1 | 12/2006 | Matthis et al. |
| 2006/0293693 A1 | 12/2006 | Farr et al. |
| 2007/0005062 A1 | 1/2007 | Lange et al. |
| 2007/0005063 A1 | 1/2007 | Bruneau et al. |
| 2007/0005137 A1 | 1/2007 | Kwak |
| 2007/0016190 A1 | 1/2007 | Martinez et al. |
| 2007/0016194 A1 | 1/2007 | Shaolian et al. |
| 2007/0016200 A1 | 1/2007 | Jackson |
| 2007/0021750 A1 | 1/2007 | Shluzas et al. |
| 2007/0032123 A1 | 2/2007 | Timm et al. |
| 2007/0043356 A1 | 2/2007 | Timm et al. |
| 2007/0043357 A1 | 2/2007 | Kirschman |
| 2007/0043358 A1 | 2/2007 | Molz, IV et al. |
| 2007/0043359 A1 | 2/2007 | Altarac et al. |
| 2007/0043364 A1 | 2/2007 | Cawley et al. |
| 2007/0049931 A1 | 3/2007 | Justis et al. |
| 2007/0049933 A1 | 3/2007 | Ahn et al. |
| 2007/0049936 A1 | 3/2007 | Colleran et al. |
| 2007/0055236 A1 | 3/2007 | Hudgins et al. |
| 2007/0055239 A1 | 3/2007 | Sweeney et al. |
| 2007/0055240 A1 | 3/2007 | Matthis et al. |
| 2007/0055241 A1 | 3/2007 | Matthis et al. |
| 2007/0055242 A1 | 3/2007 | Bailly |
| 2007/0055244 A1 | 3/2007 | Jackson |
| 2007/0073289 A1 | 3/2007 | Kwak et al. |

(56) References Cited

U.S. PATENT DOCUMENTS

| | | |
|---|---|---|
| 2007/0073290 A1 | 3/2007 | Boehm, Jr. |
| 2007/0073291 A1 | 3/2007 | Cordaro et al. |
| 2007/0073293 A1 | 3/2007 | Martz et al. |
| 2007/0073294 A1 | 3/2007 | Chin et al. |
| 2007/0078460 A1 | 4/2007 | Frigg et al. |
| 2007/0078461 A1 | 4/2007 | Shluzas |
| 2007/0083199 A1 | 4/2007 | Baccelli |
| 2007/0088357 A1 | 4/2007 | Johnson et al. |
| 2007/0088359 A1 | 4/2007 | Woods et al. |
| 2007/0090238 A1 | 4/2007 | Justis |
| 2007/0093813 A1 | 4/2007 | Callahan et al. |
| 2007/0093814 A1 | 4/2007 | Callahan, II et al. |
| 2007/0093815 A1 | 4/2007 | Callahan, II et al. |
| 2007/0093818 A1 | 4/2007 | Biedermann et al. |
| 2007/0093819 A1 | 4/2007 | Albert |
| 2007/0093824 A1 | 4/2007 | Hestad et al. |
| 2007/0093826 A1 | 4/2007 | Hawkes et al. |
| 2007/0093833 A1 | 4/2007 | Kuiper et al. |
| 2007/0100341 A1 | 5/2007 | Reglos et al. |
| 2007/0118117 A1 | 5/2007 | Altarac et al. |
| 2007/0118118 A1 | 5/2007 | Kwak et al. |
| 2007/0118119 A1 | 5/2007 | Hestad |
| 2007/0118122 A1 | 5/2007 | Butler et al. |
| 2007/0118123 A1 | 5/2007 | Strausbaugh et al. |
| 2007/0118124 A1 | 5/2007 | Biedermann et al. |
| 2007/0123867 A1 | 5/2007 | Kirschman |
| 2007/0123870 A1 | 5/2007 | Jeon et al. |
| 2007/0129729 A1 | 6/2007 | Petit et al. |
| 2007/0156142 A1 | 7/2007 | Rezach et al. |
| 2007/0161986 A1 | 7/2007 | Levy |
| 2007/0161991 A1 | 7/2007 | Altarac et al. |
| 2007/0161994 A1 | 7/2007 | Lowery et al. |
| 2007/0161995 A1 | 7/2007 | Trautwein et al. |
| 2007/0161996 A1 | 7/2007 | Biedermann et al. |
| 2007/0161997 A1 | 7/2007 | Thramann et al. |
| 2007/0161999 A1 | 7/2007 | Biedermann et al. |
| 2007/0167948 A1 | 7/2007 | Abdou |
| 2007/0167949 A1 | 7/2007 | Altarac et al. |
| 2007/0173818 A1 | 7/2007 | Hestad et al. |
| 2007/0173819 A1 | 7/2007 | Sandlin |
| 2007/0173820 A1 | 7/2007 | Trieu |
| 2007/0173822 A1 | 7/2007 | Bruneau et al. |
| 2007/0173828 A1 | 7/2007 | Firkins et al. |
| 2007/0173832 A1 | 7/2007 | Tebbe et al. |
| 2007/0191832 A1 | 8/2007 | Trieu |
| 2007/0191839 A1 | 8/2007 | Justis et al. |
| 2007/0191841 A1 | 8/2007 | Justis et al. |
| 2007/0191846 A1 | 8/2007 | Bruneau et al. |
| 2007/0198014 A1 | 8/2007 | Graf et al. |
| 2007/0208344 A1 | 9/2007 | Young |
| 2007/0213720 A1 | 9/2007 | Gordon et al. |
| 2007/0219554 A1 | 9/2007 | Landry et al. |
| 2007/0225707 A1 | 9/2007 | Wisnewski et al. |
| 2007/0225708 A1 | 9/2007 | Biedermann et al. |
| 2007/0225711 A1 | 9/2007 | Ensign |
| 2007/0233073 A1 | 10/2007 | Wisnewski et al. |
| 2007/0233078 A1 | 10/2007 | Justis et al. |
| 2007/0233080 A1 | 10/2007 | Na et al. |
| 2007/0233085 A1 | 10/2007 | Biedermann et al. |
| 2007/0233086 A1 | 10/2007 | Harms et al. |
| 2007/0233089 A1 | 10/2007 | Dipoto et al. |
| 2007/0233092 A1 | 10/2007 | Falahee |
| 2007/0233094 A1 | 10/2007 | Colleran et al. |
| 2007/0233095 A1 | 10/2007 | Schlapfer |
| 2007/0233155 A1 | 10/2007 | Lovell |
| 2007/0244481 A1 | 10/2007 | Timm |
| 2007/0244482 A1 | 10/2007 | Aferzon |
| 2007/0250061 A1 | 10/2007 | Chin et al. |
| 2007/0260243 A1 | 11/2007 | Kagami |
| 2007/0270813 A1 | 11/2007 | Garamszegi |
| 2007/0270821 A1 | 11/2007 | Trieu et al. |
| 2007/0270836 A1 | 11/2007 | Bruneau et al. |
| 2007/0270837 A1 | 11/2007 | Eckhardt et al. |
| 2007/0270838 A1 | 11/2007 | Bruneau et al. |
| 2007/0270843 A1 | 11/2007 | Matthis et al. |
| 2007/0270869 A1 | 11/2007 | Young et al. |
| 2007/0276371 A1 | 11/2007 | Baynham et al. |
| 2007/0276379 A1 | 11/2007 | Miller et al. |
| 2007/0276380 A1 | 11/2007 | Jahng et al. |
| 2007/0288004 A1 | 12/2007 | Alvarez |
| 2007/0288012 A1 | 12/2007 | Colleran et al. |
| 2007/0293862 A1 | 12/2007 | Jackson |
| 2008/0009862 A1 | 1/2008 | Hoffman |
| 2008/0009864 A1 | 1/2008 | Forton et al. |
| 2008/0015578 A1 | 1/2008 | Erickson et al. |
| 2008/0015579 A1 | 1/2008 | Whipple |
| 2008/0015580 A1 | 1/2008 | Chao |
| 2008/0015597 A1 | 1/2008 | Whipple |
| 2008/0021454 A1 | 1/2008 | Chao et al. |
| 2008/0021455 A1 | 1/2008 | Chao et al. |
| 2008/0021462 A1 | 1/2008 | Trieu |
| 2008/0021464 A1 | 1/2008 | Morin et al. |
| 2008/0021465 A1 | 1/2008 | Shadduck et al. |
| 2008/0027432 A1 | 1/2008 | Strauss et al. |
| 2008/0039843 A1 | 2/2008 | Abdou |
| 2008/0045951 A1 | 2/2008 | Fanger et al. |
| 2008/0045955 A1 | 2/2008 | Berrevoets et al. |
| 2008/0051780 A1 | 2/2008 | Vaidya et al. |
| 2008/0051787 A1 | 2/2008 | Remington et al. |
| 2008/0058811 A1 | 3/2008 | Alleyne et al. |
| 2008/0058812 A1 | 3/2008 | Zehnder |
| 2008/0065071 A1 | 3/2008 | Park |
| 2008/0065073 A1 | 3/2008 | Perriello et al. |
| 2008/0065075 A1 | 3/2008 | Dant |
| 2008/0065077 A1 | 3/2008 | Ferree |
| 2008/0065079 A1 | 3/2008 | Bruneau et al. |
| 2008/0071273 A1 | 3/2008 | Hawkes et al. |
| 2008/0071274 A1 | 3/2008 | Ensign |
| 2008/0077136 A1 | 3/2008 | Triplett et al. |
| 2008/0077138 A1 | 3/2008 | Cohen et al. |
| 2008/0077139 A1 | 3/2008 | Landry et al. |
| 2008/0077143 A1 | 3/2008 | Shluzas |
| 2008/0086131 A1 | 4/2008 | Daly et al. |
| 2008/0086132 A1 | 4/2008 | Biedermann et al. |
| 2008/0091213 A1 | 4/2008 | Jackson |
| 2008/0097441 A1 | 4/2008 | Hayes et al. |
| 2008/0103502 A1 | 5/2008 | Capote et al. |
| 2008/0108992 A1 | 5/2008 | Barry et al. |
| 2008/0114362 A1 | 5/2008 | Justis et al. |
| 2008/0114403 A1 | 5/2008 | Kuester et al. |
| 2008/0119849 A1 | 5/2008 | Beardsley et al. |
| 2008/0119857 A1 | 5/2008 | Potash et al. |
| 2008/0119858 A1 | 5/2008 | Potash |
| 2008/0125777 A1 | 5/2008 | Veldman et al. |
| 2008/0125787 A1 | 5/2008 | Doubler et al. |
| 2008/0125813 A1 | 5/2008 | Erickson et al. |
| 2008/0132957 A1 | 6/2008 | Matthis et al. |
| 2008/0140075 A1 | 6/2008 | Ensign et al. |
| 2008/0140076 A1 | 6/2008 | Jackson |
| 2008/0140133 A1 | 6/2008 | Allard et al. |
| 2008/0140136 A1 | 6/2008 | Jackson |
| 2008/0147121 A1 | 6/2008 | Justis et al. |
| 2008/0147122 A1 | 6/2008 | Jackson |
| 2008/0147129 A1 | 6/2008 | Biedermann et al. |
| 2008/0147195 A1 | 6/2008 | Kwak et al. |
| 2008/0154279 A1 | 6/2008 | Schumacher et al. |
| 2008/0154308 A1 | 6/2008 | Sherman et al. |
| 2008/0154315 A1 | 6/2008 | Jackson |
| 2008/0161857 A1 | 7/2008 | Hestad et al. |
| 2008/0161863 A1 | 7/2008 | Arnold et al. |
| 2008/0167687 A1 | 7/2008 | Colleran et al. |
| 2008/0172090 A1 | 7/2008 | Molz |
| 2008/0172091 A1 | 7/2008 | Anderson |
| 2008/0172096 A1 | 7/2008 | Hawkins |
| 2008/0177316 A1 | 7/2008 | Bergeron et al. |
| 2008/0177317 A1 | 7/2008 | Jackson |
| 2008/0177321 A1 | 7/2008 | Drewry et al. |
| 2008/0177322 A1 | 7/2008 | Davis et al. |
| 2008/0177323 A1 | 7/2008 | Null et al. |
| 2008/0177388 A1 | 7/2008 | Patterson et al. |
| 2008/0183212 A1 | 7/2008 | Veldman et al. |
| 2008/0183213 A1 | 7/2008 | Veldman et al. |
| 2008/0183215 A1 | 7/2008 | Altarac et al. |
| 2008/0183216 A1 | 7/2008 | Jackson |

(56) References Cited

U.S. PATENT DOCUMENTS

| | | |
|---|---|---|
| 2008/0183219 A1 | 7/2008 | Bertram |
| 2008/0183223 A1 | 7/2008 | Jeon et al. |
| 2008/0188898 A1 | 8/2008 | Jackson |
| 2008/0195153 A1 | 8/2008 | Thompson |
| 2008/0195155 A1 | 8/2008 | Hoffman et al. |
| 2008/0195159 A1 | 8/2008 | Kloss et al. |
| 2008/0200918 A1 | 8/2008 | Spitler et al. |
| 2008/0200956 A1 | 8/2008 | Beckwith et al. |
| 2008/0215095 A1 | 9/2008 | Biedermann et al. |
| 2008/0228184 A1 | 9/2008 | Hestad |
| 2008/0228228 A1 | 9/2008 | Hestad et al. |
| 2008/0234736 A1 | 9/2008 | Trieu et al. |
| 2008/0234737 A1 | 9/2008 | Boschert |
| 2008/0234738 A1 | 9/2008 | Zylber et al. |
| 2008/0234739 A1 | 9/2008 | Hudgins et al. |
| 2008/0234744 A1 | 9/2008 | Zylber et al. |
| 2008/0234756 A1 | 9/2008 | Sutcliffe et al. |
| 2008/0234759 A1 | 9/2008 | Marino |
| 2008/0234761 A1 | 9/2008 | Jackson |
| 2008/0243052 A1 | 10/2008 | Pond et al. |
| 2008/0243185 A1 | 10/2008 | Felix et al. |
| 2008/0243193 A1 | 10/2008 | Ensign et al. |
| 2008/0249570 A1 | 10/2008 | Carson et al. |
| 2008/0262548 A1 | 10/2008 | Lange et al. |
| 2008/0262551 A1 | 10/2008 | Rice et al. |
| 2008/0262554 A1 | 10/2008 | Hayes et al. |
| 2008/0262556 A1 | 10/2008 | Jacofsky et al. |
| 2008/0269742 A1 | 10/2008 | Levy et al. |
| 2008/0269804 A1 | 10/2008 | Holt |
| 2008/0269805 A1 | 10/2008 | Dekutoski et al. |
| 2008/0269809 A1 | 10/2008 | Garamszegi |
| 2008/0275456 A1 | 11/2008 | Vonwiller et al. |
| 2008/0275504 A1 | 11/2008 | Bonin et al. |
| 2008/0287994 A1 | 11/2008 | Perez-Cruet et al. |
| 2008/0288002 A1 | 11/2008 | Crall et al. |
| 2008/0294203 A1 | 11/2008 | Kovach et al. |
| 2008/0300630 A1 | 12/2008 | Bonnema et al. |
| 2008/0300631 A1 | 12/2008 | Tornier |
| 2008/0300633 A1 | 12/2008 | Jackson |
| 2008/0306513 A1 | 12/2008 | Winslow et al. |
| 2008/0306525 A1 | 12/2008 | Mitchell et al. |
| 2008/0306526 A1 | 12/2008 | Winslow et al. |
| 2008/0306533 A1 | 12/2008 | Winslow et al. |
| 2008/0306536 A1 | 12/2008 | Frigg et al. |
| 2008/0306540 A1 | 12/2008 | Mitchell et al. |
| 2008/0306543 A1 | 12/2008 | Cain et al. |
| 2008/0312655 A1 | 12/2008 | Kirschman et al. |
| 2008/0312692 A1 | 12/2008 | Brennan et al. |
| 2008/0312696 A1 | 12/2008 | Butters et al. |
| 2008/0312701 A1 | 12/2008 | Butters et al. |
| 2008/0312703 A1 | 12/2008 | Hestad et al. |
| 2008/0312704 A1 | 12/2008 | Hestad et al. |
| 2008/0319482 A1 | 12/2008 | Jackson |
| 2008/0319490 A1 | 12/2008 | Jackson |
| 2009/0005787 A1 | 1/2009 | Crall et al. |
| 2009/0005813 A1 | 1/2009 | Crall et al. |
| 2009/0005814 A1 | 1/2009 | Miller et al. |
| 2009/0012562 A1 | 1/2009 | Hestad et al. |
| 2009/0012567 A1 | 1/2009 | Biedermann et al. |
| 2009/0018557 A1 | 1/2009 | Pisharodi |
| 2009/0018583 A1 | 1/2009 | Song et al. |
| 2009/0024165 A1 | 1/2009 | Ferree |
| 2009/0024169 A1 | 1/2009 | Triplett et al. |
| 2009/0030457 A1 | 1/2009 | Janowski et al. |
| 2009/0030464 A1 | 1/2009 | Hestad et al. |
| 2009/0036929 A1 | 2/2009 | Reglos et al. |
| 2009/0036932 A1 | 2/2009 | Rouyer et al. |
| 2009/0036934 A1 | 2/2009 | Biedermann et al. |
| 2009/0048601 A1 | 2/2009 | Forton et al. |
| 2009/0048631 A1 | 2/2009 | Bhatnagar et al. |
| 2009/0062860 A1 | 3/2009 | Frasier et al. |
| 2009/0062865 A1 | 3/2009 | Schumacher |
| 2009/0062866 A1 | 3/2009 | Jackson |
| 2009/0062867 A1 | 3/2009 | Schumacher |
| 2009/0062914 A1 | 3/2009 | Marino |
| 2009/0069849 A1 | 3/2009 | Oh et al. |
| 2009/0069852 A1 | 3/2009 | Farris et al. |
| 2009/0069853 A1 | 3/2009 | Schumacher |
| 2009/0076550 A1 | 3/2009 | Bernhardt, Jr. et al. |
| 2009/0076552 A1 | 3/2009 | Tornier |
| 2009/0082666 A1 | 3/2009 | Geist et al. |
| 2009/0082812 A1 | 3/2009 | Lewis |
| 2009/0082815 A1 | 3/2009 | Zylber et al. |
| 2009/0082819 A1 | 3/2009 | Blain et al. |
| 2009/0088769 A1 | 4/2009 | Poletti |
| 2009/0088799 A1 | 4/2009 | Yeh |
| 2009/0088803 A1 | 4/2009 | Justis et al. |
| 2009/0088807 A1 | 4/2009 | Castaneda et al. |
| 2009/0093820 A1 | 4/2009 | Trieu et al. |
| 2009/0093843 A1 | 4/2009 | Lemoine et al. |
| 2009/0093846 A1 | 4/2009 | Hestad et al. |
| 2009/0099606 A1 | 4/2009 | Hestad et al. |
| 2009/0099608 A1 | 4/2009 | Szczesny |
| 2009/0105769 A1 | 4/2009 | Rock et al. |
| 2009/0105770 A1 | 4/2009 | Berrevoets et al. |
| 2009/0105771 A1 | 4/2009 | Lei et al. |
| 2009/0105820 A1 | 4/2009 | Jackson |
| 2009/0112265 A1 | 4/2009 | Hudgins et al. |
| 2009/0112266 A1 | 4/2009 | Weng et al. |
| 2009/0112269 A1 | 4/2009 | Lieberman et al. |
| 2009/0118772 A1 | 5/2009 | Diederich et al. |
| 2009/0131983 A1 | 5/2009 | Biedermann et al. |
| 2009/0138044 A1 | 5/2009 | Bergeron et al. |
| 2009/0138052 A1 | 5/2009 | Biedermann et al. |
| 2009/0143827 A1 | 6/2009 | Levy et al. |
| 2009/0143828 A1 | 6/2009 | Stad et al. |
| 2009/0149885 A1 | 6/2009 | Durward et al. |
| 2009/0149892 A1 | 6/2009 | Stad et al. |
| 2009/0157120 A1 | 6/2009 | Marino et al. |
| 2009/0163901 A1 | 6/2009 | Fisher et al. |
| 2009/0163953 A1 | 6/2009 | Biedermann et al. |
| 2009/0163954 A1 | 6/2009 | Kwak |
| 2009/0163955 A1 | 6/2009 | Moumene et al. |
| 2009/0163956 A1 | 6/2009 | Biedermann et al. |
| 2009/0163961 A1 | 6/2009 | Kirschman |
| 2009/0163963 A1 | 6/2009 | Berrevoets |
| 2009/0171392 A1 | 7/2009 | Garcia-Bengochea et al. |
| 2009/0171395 A1 | 7/2009 | Jeon et al. |
| 2009/0177232 A1 | 7/2009 | Kiester |
| 2009/0177237 A1 | 7/2009 | Zucherman et al. |
| 2009/0182380 A1 | 7/2009 | Abdelgany |
| 2009/0182430 A1 | 7/2009 | Tyber et al. |
| 2009/0192548 A1 | 7/2009 | Jeon et al. |
| 2009/0192551 A1 | 7/2009 | Cianfrani et al. |
| 2009/0198280 A1 | 8/2009 | Spratt et al. |
| 2009/0198281 A1 | 8/2009 | Rice et al. |
| 2009/0198289 A1 | 8/2009 | Manderson |
| 2009/0198291 A1 | 8/2009 | Kevin et al. |
| 2009/0204155 A1 | 8/2009 | Aschmann |
| 2009/0216278 A1 | 8/2009 | Song |
| 2009/0216280 A1 | 8/2009 | Hutchinson |
| 2009/0221877 A1 | 9/2009 | Woods |
| 2009/0228045 A1 | 9/2009 | Hayes et al. |
| 2009/0240292 A1 | 9/2009 | Butler et al. |
| 2009/0248030 A1 | 10/2009 | Butler et al. |
| 2009/0248075 A1 | 10/2009 | Ogilvie et al. |
| 2009/0248077 A1 | 10/2009 | Johns |
| 2009/0248083 A1 | 10/2009 | Patterson et al. |
| 2009/0248088 A1 | 10/2009 | Biedermann |
| 2009/0254125 A1 | 10/2009 | Predick |
| 2009/0259254 A1 | 10/2009 | Pisharodi |
| 2009/0259257 A1 | 10/2009 | Prevost |
| 2009/0259258 A1 | 10/2009 | Perez-Cruet et al. |
| 2009/0264895 A1 | 10/2009 | Gasperut et al. |
| 2009/0264896 A1 | 10/2009 | Biedermann et al. |
| 2009/0264930 A1 | 10/2009 | McBride |
| 2009/0264933 A1 | 10/2009 | Carls et al. |
| 2009/0270916 A1 | 10/2009 | Ramsay et al. |
| 2009/0270917 A1 | 10/2009 | Boehm |
| 2009/0270920 A1 | 10/2009 | Douget et al. |
| 2009/0270921 A1 | 10/2009 | Krause |
| 2009/0270922 A1 | 10/2009 | Biedermann et al. |
| 2009/0275981 A1 | 11/2009 | Abdelgany et al. |
| 2009/0275983 A1 | 11/2009 | Veldman et al. |

(56) References Cited

U.S. PATENT DOCUMENTS

| | | |
|---|---|---|
| 2009/0275985 A1 | 11/2009 | Jackson |
| 2009/0275986 A1 | 11/2009 | Prevost et al. |
| 2009/0281542 A1 | 11/2009 | Justis |
| 2009/0281571 A1 | 11/2009 | Weaver et al. |
| 2009/0281572 A1 | 11/2009 | White |
| 2009/0281573 A1 | 11/2009 | Biedermann et al. |
| 2009/0281574 A1 | 11/2009 | Jackson |
| 2009/0287252 A1 | 11/2009 | Marik et al. |
| 2009/0287253 A1 | 11/2009 | Felix et al. |
| 2009/0299411 A1 | 12/2009 | Laskowitz et al. |
| 2009/0299415 A1 | 12/2009 | Pimenta |
| 2009/0306719 A1 | 12/2009 | Meyer, III et al. |
| 2009/0306720 A1 | 12/2009 | Doubler et al. |
| 2009/0312804 A1 | 12/2009 | Gamache et al. |
| 2009/0326582 A1 | 12/2009 | Songer et al. |
| 2009/0326583 A1 | 12/2009 | Moumene et al. |
| 2009/0326586 A1 | 12/2009 | Duarte |
| 2010/0004692 A1 | 1/2010 | Biedermann et al. |
| 2010/0004694 A1 | 1/2010 | Little |
| 2010/0004695 A1 | 1/2010 | Stad et al. |
| 2010/0010540 A1 | 1/2010 | Park |
| 2010/0010542 A1 | 1/2010 | Jackson |
| 2010/0010543 A1 | 1/2010 | Jackson |
| 2010/0023061 A1 | 1/2010 | Randol et al. |
| 2010/0030224 A1 | 2/2010 | Winslow et al. |
| 2010/0030272 A1 | 2/2010 | Winslow et al. |
| 2010/0030283 A1 | 2/2010 | King et al. |
| 2010/0036417 A1 | 2/2010 | James et al. |
| 2010/0036422 A1 | 2/2010 | Flynn et al. |
| 2010/0036423 A1 | 2/2010 | Hayes et al. |
| 2010/0036425 A1 | 2/2010 | Barrus et al. |
| 2010/0036432 A1 | 2/2010 | Ely |
| 2010/0036443 A1 | 2/2010 | Hutton et al. |
| 2010/0042149 A1 | 2/2010 | Chao et al. |
| 2010/0042152 A1 | 2/2010 | Semler et al. |
| 2010/0042155 A1 | 2/2010 | Biedermann et al. |
| 2010/0042156 A1 | 2/2010 | Harms et al. |
| 2010/0057125 A1 | 3/2010 | Viker |
| 2010/0057126 A1 | 3/2010 | Hestad |
| 2010/0057131 A1 | 3/2010 | Ely et al. |
| 2010/0063544 A1 | 3/2010 | Butler |
| 2010/0063545 A1 | 3/2010 | Richelsoph |
| 2010/0063546 A1 | 3/2010 | Miller et al. |
| 2010/0063547 A1 | 3/2010 | Morin et al. |
| 2010/0063550 A1 | 3/2010 | Felix et al. |
| 2010/0063552 A1 | 3/2010 | Chin et al. |
| 2010/0069919 A1 | 3/2010 | Carls et al. |
| 2010/0069969 A1 | 3/2010 | Ampuero et al. |
| 2010/0082066 A1 | 4/2010 | Biyani |
| 2010/0087858 A1 | 4/2010 | Abdou |
| 2010/0087862 A1 | 4/2010 | Biedermann et al. |
| 2010/0087863 A1 | 4/2010 | Biedermann et al. |
| 2010/0087864 A1 | 4/2010 | Klein et al. |
| 2010/0087865 A1 | 4/2010 | Biedermann et al. |
| 2010/0094343 A1 | 4/2010 | Pham et al. |
| 2010/0094348 A1 | 4/2010 | Biedermann et al. |
| 2010/0094349 A1 | 4/2010 | Hammer et al. |
| 2010/0094352 A1 | 4/2010 | Iott et al. |
| 2010/0094353 A1 | 4/2010 | Shim et al. |
| 2010/0100136 A1 | 4/2010 | Won et al. |
| 2010/0100137 A1 | 4/2010 | Justis et al. |
| 2010/0106189 A1 | 4/2010 | Miller |
| 2010/0106192 A1 | 4/2010 | Barry |
| 2010/0114165 A1 | 5/2010 | Ely |
| 2010/0114170 A1 | 5/2010 | Barrus et al. |
| 2010/0114171 A1 | 5/2010 | Boachie-Adjei et al. |
| 2010/0114179 A1 | 5/2010 | Moore et al. |
| 2010/0114180 A1 | 5/2010 | Rock et al. |
| 2010/0114182 A1 | 5/2010 | Wilcox et al. |
| 2010/0121386 A1 | 5/2010 | Peultier et al. |
| 2010/0125302 A1 | 5/2010 | Hammill, Sr. et al. |
| 2010/0137908 A1 | 6/2010 | Zhang |
| 2010/0137912 A1 | 6/2010 | Alcock et al. |
| 2010/0137918 A1 | 6/2010 | Wilcox et al. |
| 2010/0137920 A1 | 6/2010 | Hammill, Sr. et al. |
| 2010/0152776 A1 | 6/2010 | Keyer et al. |
| 2010/0152785 A1 | 6/2010 | Forton et al. |
| 2010/0152787 A1 | 6/2010 | Walsh et al. |
| 2010/0160965 A1 | 6/2010 | Viker |
| 2010/0160967 A1 | 6/2010 | Capozzoli |
| 2010/0160968 A1 | 6/2010 | Joshi et al. |
| 2010/0160974 A1 | 6/2010 | Viker |
| 2010/0160976 A1 | 6/2010 | Biedermann et al. |
| 2010/0168796 A1 | 7/2010 | Eliasen et al. |
| 2010/0168800 A1 | 7/2010 | Biedermann et al. |
| 2010/0168801 A1 | 7/2010 | Biedermann et al. |
| 2010/0168803 A1 | 7/2010 | Hestad et al. |
| 2010/0174322 A1 | 7/2010 | Abdelgany et al. |
| 2010/0179602 A1 | 7/2010 | Dauster et al. |
| 2010/0191293 A1 | 7/2010 | Jackson |
| 2010/0204735 A1 | 8/2010 | Gephart et al. |
| 2010/0211104 A1 | 8/2010 | Moumene et al. |
| 2010/0211105 A1 | 8/2010 | Moumene et al. |
| 2010/0211114 A1 | 8/2010 | Jackson |
| 2010/0222822 A1 | 9/2010 | Farris et al. |
| 2010/0222828 A1 | 9/2010 | Stad et al. |
| 2010/0228292 A1 | 9/2010 | Arnold et al. |
| 2010/0234902 A1 | 9/2010 | Biedermann et al. |
| 2010/0249843 A1 | 9/2010 | Wegzyn, III |
| 2010/0249846 A1 | 9/2010 | Simonson |
| 2010/0249856 A1 | 9/2010 | Iott et al. |
| 2010/0262185 A1 | 10/2010 | Gelfand et al. |
| 2010/0262187 A1 | 10/2010 | Marik et al. |
| 2010/0262190 A1 | 10/2010 | Ballard et al. |
| 2010/0262191 A1 | 10/2010 | Marik et al. |
| 2010/0262192 A1 | 10/2010 | Foley |
| 2010/0274285 A1 | 10/2010 | Rouleau |
| 2010/0274287 A1 | 10/2010 | Rouleau et al. |
| 2010/0274288 A1 | 10/2010 | Prevost et al. |
| 2010/0298891 A1 | 11/2010 | Jackson |
| 2010/0305621 A1 | 12/2010 | Wang et al. |
| 2010/0312288 A1 | 12/2010 | Hammill, Sr. et al. |
| 2010/0331885 A1 | 12/2010 | Remington et al. |
| 2011/0004256 A1 | 1/2011 | Biedermann et al. |
| 2011/0009906 A1 | 1/2011 | Hestad et al. |
| 2011/0009911 A1 | 1/2011 | Hammill et al. |
| 2011/0029022 A1 | 2/2011 | Zehnder et al. |
| 2011/0040338 A1 | 2/2011 | Jackson |
| 2011/0046683 A1 | 2/2011 | Biedermann et al. |
| 2011/0093015 A1 | 4/2011 | Ramsay et al. |
| 2011/0093021 A1 | 4/2011 | Fanger et al. |
| 2011/0106174 A1 | 5/2011 | Rezach |
| 2011/0106175 A1 | 5/2011 | Rezach |
| 2011/0130792 A1 | 6/2011 | Nydegger et al. |
| 2011/0152939 A1 | 6/2011 | Aldridge |
| 2011/0152949 A1 | 6/2011 | Biedermann et al. |
| 2011/0160778 A1 | 6/2011 | Elsbury |
| 2011/0166610 A1 | 7/2011 | Altarac et al. |
| 2011/0178558 A1 | 7/2011 | Barry |
| 2011/0178560 A1 | 7/2011 | Butler et al. |
| 2011/0184469 A1 | 7/2011 | Ballard et al. |
| 2011/0184471 A1 | 7/2011 | Foley et al. |
| 2011/0190822 A1 | 8/2011 | Spitler et al. |
| 2011/0196430 A1 | 8/2011 | Walsh |
| 2011/0202094 A1 | 8/2011 | Pereira et al. |
| 2011/0202095 A1 | 8/2011 | Semler et al. |
| 2011/0230915 A1 | 9/2011 | Anderson et al. |
| 2011/0238119 A1 | 9/2011 | Moumene et al. |
| 2011/0251644 A1 | 10/2011 | Hestad et al. |
| 2011/0257685 A1 | 10/2011 | Hay et al. |
| 2011/0257687 A1 | 10/2011 | Trieu et al. |
| 2011/0257689 A1 | 10/2011 | Fiechter et al. |
| 2011/0257690 A1 | 10/2011 | Rezach |
| 2011/0263945 A1 | 10/2011 | Peterson et al. |
| 2011/0313460 A1 | 12/2011 | Mclean et al. |
| 2011/0313463 A1 | 12/2011 | McLean |
| 2011/0313471 A1 | 12/2011 | McLean et al. |
| 2012/0029568 A1 | 2/2012 | Jackson |
| 2012/0046699 A1 | 2/2012 | Jones et al. |
| 2012/0053636 A1 | 3/2012 | Schmocker |
| 2012/0071928 A1 | 3/2012 | Jackson |
| 2012/0078307 A1 | 3/2012 | Nihalani |
| 2012/0197314 A1 | 8/2012 | Farris |
| 2012/0232598 A1 | 9/2012 | Hestad et al. |

(56) References Cited

U.S. PATENT DOCUMENTS

| | | |
|---|---|---|
| 2012/0310284 A1 | 12/2012 | Gerchow |
| 2013/0046350 A1* | 2/2013 | Jackson ............. A61B 17/7037 606/305 |
| 2013/0072992 A1* | 3/2013 | Jackson ............. A61B 17/8605 606/305 |
| 2013/0103097 A1 | 4/2013 | May et al. |
| 2013/0150852 A1 | 6/2013 | Shluzas et al. |

FOREIGN PATENT DOCUMENTS

| | | |
|---|---|---|
| DE | 3630863 | 3/1988 |
| DE | G9202745.8 | 4/1992 |
| DE | 4425392 | 11/1995 |
| DE | 29806563 | 6/1998 |
| DE | 29810798 | 12/1999 |
| DE | 19951145 | 5/2001 |
| DE | 102007055745 | 7/2008 |
| EP | 0195455 | 9/1986 |
| EP | 0172130 | 2/1987 |
| EP | 0276153 | 7/1988 |
| EP | 0667127 | 8/1995 |
| EP | 0669109 | 8/1995 |
| EP | 0677277 | 10/1995 |
| EP | 1277444 | 1/2003 |
| EP | 2082709 | 7/2009 |
| EP | 2468198 | 12/2010 |
| ES | 2384773 | 7/2012 |
| FR | 2467312 | 4/1981 |
| FR | 2715825 | 8/1995 |
| FR | 2717370 | 9/1995 |
| FR | 2718946 | 10/1995 |
| FR | 2799949 | 4/2001 |
| FR | 2814936 | 4/2002 |
| FR | 2815535 | 4/2002 |
| FR | 2856578 | 6/2003 |
| FR | 2865377 | 1/2004 |
| FR | 2846223 | 4/2004 |
| FR | 2857850 | 4/2004 |
| FR | 2925288 | 6/2009 |
| GB | 203508 | 9/1923 |
| GB | 2082709 | 3/1982 |
| GB | 2140523 | 11/1984 |
| GB | 2365345 | 2/2002 |
| GB | 2382304 | 5/2003 |
| JP | S4867159 | 9/1973 |
| JP | S50106061 | 8/1975 |
| JP | H10277070 | 10/1998 |
| JP | 2000325358 | 3/2000 |
| JP | 2002052030 | 2/2002 |
| JP | 2002221218 | 8/2002 |
| SU | 371359 | 2/1973 |
| WO | 8909030 | 10/1989 |
| WO | 8912431 | 12/1989 |
| WO | 9116018 | 10/1991 |
| WO | 9116020 | 10/1991 |
| WO | 9203100 | 3/1992 |
| WO | 9321848 | 11/1993 |
| WO | 9325161 | 12/1993 |
| WO | 9410927 | 5/1994 |
| WO | 9410944 | 5/1994 |
| WO | 9426191 | 11/1994 |
| WO | 9428824 | 12/1994 |
| WO | 9501132 | 1/1995 |
| WO | 9513755 | 5/1995 |
| WO | 9528889 | 11/1995 |
| WO | 9531947 | 11/1995 |
| WO | 9535067 | 12/1995 |
| WO | 9606576 | 3/1996 |
| WO | 9621396 | 7/1996 |
| WO | 9625104 | 8/1996 |
| WO | 9628105 | 9/1996 |
| WO | 9628118 | 9/1996 |
| WO | 9641582 | 12/1996 |
| WO | 9714366 | 4/1997 |
| WO | 9714368 | 4/1997 |
| WO | 9727812 | 8/1997 |
| WO | 9730649 | 8/1997 |
| WO | 9737604 | 10/1997 |
| WO | 9737605 | 10/1997 |
| WO | 9812977 | 4/1998 |
| WO | 9815233 | 4/1998 |
| WO | 9825534 | 6/1998 |
| WO | 9832386 | 7/1998 |
| WO | 9834554 | 8/1998 |
| WO | 9834556 | 8/1998 |
| WO | 9838924 | 9/1998 |
| WO | 9903415 | 1/1999 |
| WO | 9905980 | 2/1999 |
| WO | 9932084 | 7/1999 |
| WO | 9938463 | 8/1999 |
| WO | 9947083 | 9/1999 |
| WO | 9949802 | 10/1999 |
| WO | 0015125 | 3/2000 |
| WO | 0022997 | 4/2000 |
| WO | 0027297 | 5/2000 |
| WO | 0072769 | 7/2000 |
| WO | 0065268 | 11/2000 |
| WO | 0066045 | 11/2000 |
| WO | 0106940 | 2/2001 |
| WO | 0108574 | 2/2001 |
| WO | 0110317 | 2/2001 |
| WO | 0115612 | 3/2001 |
| WO | 0122893 | 4/2001 |
| WO | 0128435 | 4/2001 |
| WO | 0128436 | 4/2001 |
| WO | 0145576 | 6/2001 |
| WO | 0149191 | 7/2001 |
| WO | 0158370 | 8/2001 |
| WO | 0167972 | 9/2001 |
| WO | 0167974 | 9/2001 |
| WO | 0222030 | 3/2002 |
| WO | 0234150 | 5/2002 |
| WO | 02054966 | 7/2002 |
| WO | 02102259 | 12/2002 |
| WO | 03007828 | 1/2003 |
| WO | 03026523 | 4/2003 |
| WO | 03037199 | 5/2003 |
| WO | 03047442 | 6/2003 |
| WO | 03068083 | 8/2003 |
| WO | 03068088 | 8/2003 |
| WO | 03084415 | 10/2003 |
| WO | 03094699 | 11/2003 |
| WO | 2004021900 | 3/2004 |
| WO | 2004022108 | 3/2004 |
| WO | 2004041100 | 5/2004 |
| WO | 2004075778 | 9/2004 |
| WO | 2004089245 | 10/2004 |
| WO | 2004098452 | 11/2004 |
| WO | 2004105577 | 12/2004 |
| WO | 2004107997 | 12/2004 |
| WO | 2005000136 | 1/2005 |
| WO | 2005000137 | 1/2005 |
| WO | 2005013839 | 2/2005 |
| WO | 2005018466 | 3/2005 |
| WO | 2005018471 | 3/2005 |
| WO | 2005020829 | 3/2005 |
| WO | 2005030068 | 4/2005 |
| WO | 2005065374 | 7/2005 |
| WO | 2005072632 | 8/2005 |
| WO | 2005082262 | 9/2005 |
| WO | 2005087121 | 9/2005 |
| WO | 2005099400 | 10/2005 |
| WO | 2005102195 | 11/2005 |
| WO | 2005104969 | 11/2005 |
| WO | 2006005198 | 1/2006 |
| WO | 2006017616 | 2/2006 |
| WO | 2006020530 | 2/2006 |
| WO | 2006042188 | 4/2006 |
| WO | 2006047711 | 5/2006 |
| WO | 2006054111 | 5/2006 |
| WO | 2006065607 | 6/2006 |
| WO | 2006066685 | 6/2006 |
| WO | 2006068711 | 6/2006 |

(56) References Cited

FOREIGN PATENT DOCUMENTS

| | | |
|---|---|---|
| WO | 2006071742 | 7/2006 |
| WO | 2006079531 | 8/2006 |
| WO | 2006096240 | 9/2006 |
| WO | 2006096351 | 9/2006 |
| WO | 2006104874 | 10/2006 |
| WO | 2006110463 | 10/2006 |
| WO | 2006116437 | 11/2006 |
| WO | 2006119447 | 11/2006 |
| WO | 2007002409 | 1/2007 |
| WO | 2007038350 | 4/2007 |
| WO | 2007040750 | 4/2007 |
| WO | 2007040888 | 4/2007 |
| WO | 2007041702 | 4/2007 |
| WO | 2007053566 | 5/2007 |
| WO | 2007060534 | 5/2007 |
| WO | 2007075454 | 7/2007 |
| WO | 2007081849 | 8/2007 |
| WO | 2007087469 | 8/2007 |
| WO | 2007087628 | 8/2007 |
| WO | 2007090021 | 8/2007 |
| WO | 2007092056 | 8/2007 |
| WO | 2007092870 | 8/2007 |
| WO | 2007097905 | 8/2007 |
| WO | 2007109470 | 9/2007 |
| WO | 2007114834 | 10/2007 |
| WO | 2007118045 | 10/2007 |
| WO | 2007121030 | 10/2007 |
| WO | 2007121057 | 10/2007 |
| WO | 2007121271 | 10/2007 |
| WO | 2007123920 | 11/2007 |
| WO | 2007124222 | 11/2007 |
| WO | 2007124249 | 11/2007 |
| WO | 2007127595 | 11/2007 |
| WO | 2007127604 | 11/2007 |
| WO | 2007130835 | 11/2007 |
| WO | 2007130840 | 11/2007 |
| WO | 2007130941 | 11/2007 |
| WO | 2007138270 | 12/2007 |
| WO | 2007146032 | 12/2007 |
| WO | 2008005740 | 1/2008 |
| WO | 2008006098 | 1/2008 |
| WO | 2008008511 | 1/2008 |
| WO | 2008013892 | 1/2008 |
| WO | 2008027860 | 3/2008 |
| WO | 2008033742 | 3/2008 |
| WO | 2008036975 | 3/2008 |
| WO | 2008037256 | 4/2008 |
| WO | 2008039777 | 4/2008 |
| WO | 2008042948 | 4/2008 |
| WO | 2008048923 | 4/2008 |
| WO | 2008048953 | 4/2008 |
| WO | 2008051737 | 4/2008 |
| WO | 2008069420 | 6/2008 |
| WO | 2008070716 | 6/2008 |
| WO | 2008134703 | 6/2008 |
| WO | 2008078163 | 7/2008 |
| WO | 2008082737 | 7/2008 |
| WO | 2008100590 | 8/2008 |
| WO | 2008118295 | 10/2008 |
| WO | 2008119006 | 10/2008 |
| WO | 2008124772 | 10/2008 |
| WO | 2008140756 | 11/2008 |
| WO | 2008157589 | 12/2008 |
| WO | 2009003153 | 12/2008 |
| WO | 2009006225 | 1/2009 |
| WO | 2009011845 | 1/2009 |
| WO | 2009014540 | 1/2009 |
| WO | 2009015100 | 1/2009 |
| WO | 2009018086 | 2/2009 |
| WO | 2009029928 | 3/2009 |
| WO | 2009055028 | 4/2009 |
| WO | 2009055400 | 4/2009 |
| WO | 2009055407 | 4/2009 |
| WO | 2009152302 | 12/2009 |
| WO | 2009155360 | 12/2009 |
| WO | 2010017631 | 2/2010 |
| WO | 2010018316 | 2/2010 |
| WO | 2010018317 | 2/2010 |
| WO | 2010019857 | 2/2010 |
| WO | 2010030916 | 3/2010 |
| WO | 2010045383 | 4/2010 |
| WO | 2010065648 | 6/2010 |
| WO | 2010078901 | 7/2010 |
| WO | 2010111500 | 9/2010 |
| WO | 2010120989 | 10/2010 |
| WO | 2010147639 | 12/2010 |
| WO | 2011043805 | 4/2011 |
| WO | 2011068818 | 6/2011 |
| WO | 2012033532 | 3/2012 |
| WO | 2012075827 | 6/2012 |
| WO | 2012088890 | 7/2012 |

OTHER PUBLICATIONS

CD Horizon M8 Multi Axial Screw Spinal System Brochure, Medtronic Sofamor Danek, no publish date.
Claris Instrumentation Brochure, G Med, pub. 1997.
Contour Spinal System Brochure, Ortho Development, no publish date.
EBI Omega 21 Brochure, EBI Spine Systems, pub. 1999.
SDRS Surgical Dynamics Rod System Brochure, Surgical Dynamics, pub. 1998-99.
Silhouette Spinal Fixation System Brochure, Sulzer Medica Spine-Tech, no publish date.
Spine, Lipcott, Williams & Wilkins, Inc. vol. 24, No. 15, p. 1495.
The Moss Miami 6.0mm System Advertisement, author unknown, no publish date.
The Rod Plate System Brochure, Stryker Howmedica Osteonics, pub. Oct. 1999.
The Strength of Innovation Advertisement, Blackstone Medical Inc., no publish date.
Versalok Low Back Fixation System Brochure, Wright Medical Technology, Inc., pub. 1997.
VLS System Variable Locking Screw Brochure, Interpore Cross International, 1999.
Xia Spinal System Brochure, Stryker Howmedica Osteonics, no publish date.
Brochure of DePuySpine on Surgical Technique, Published 2004, pp. 1-36.

* cited by examiner

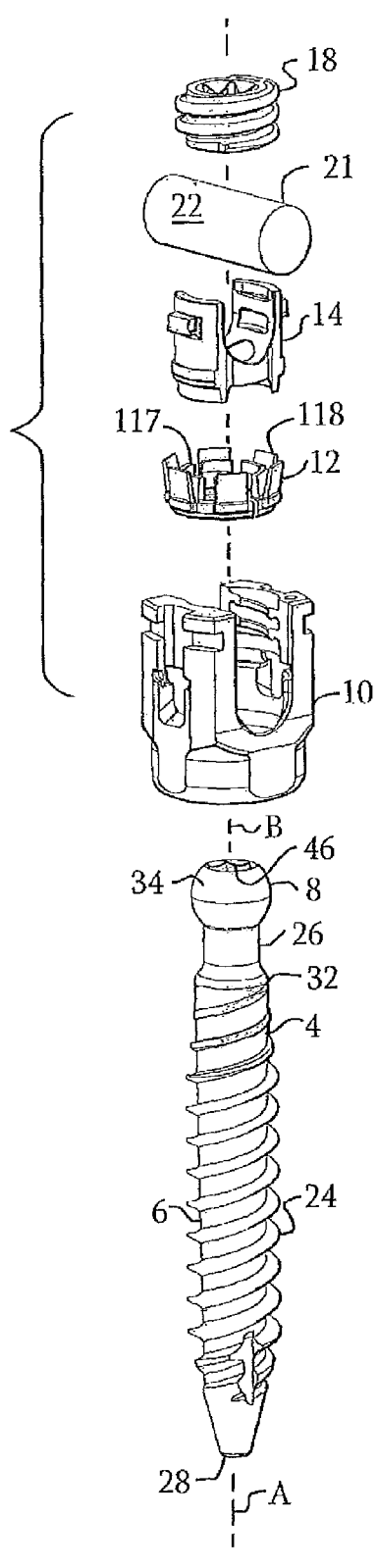
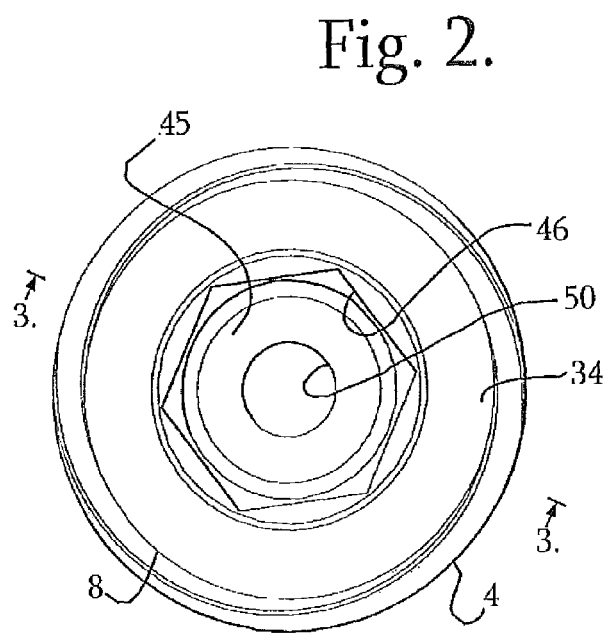
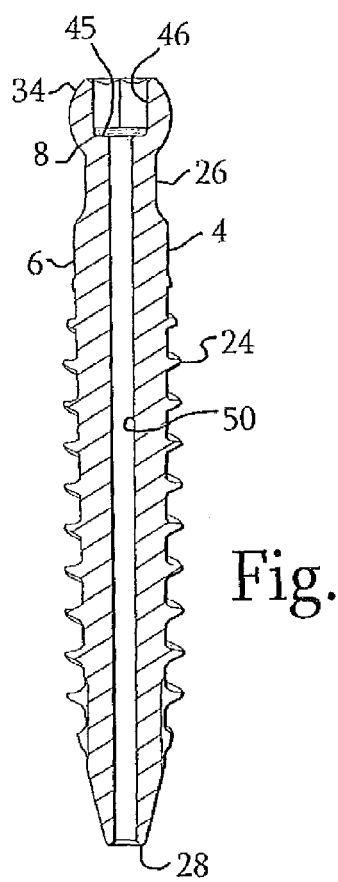
Fig. 1.
Fig. 2.
Fig. 3.

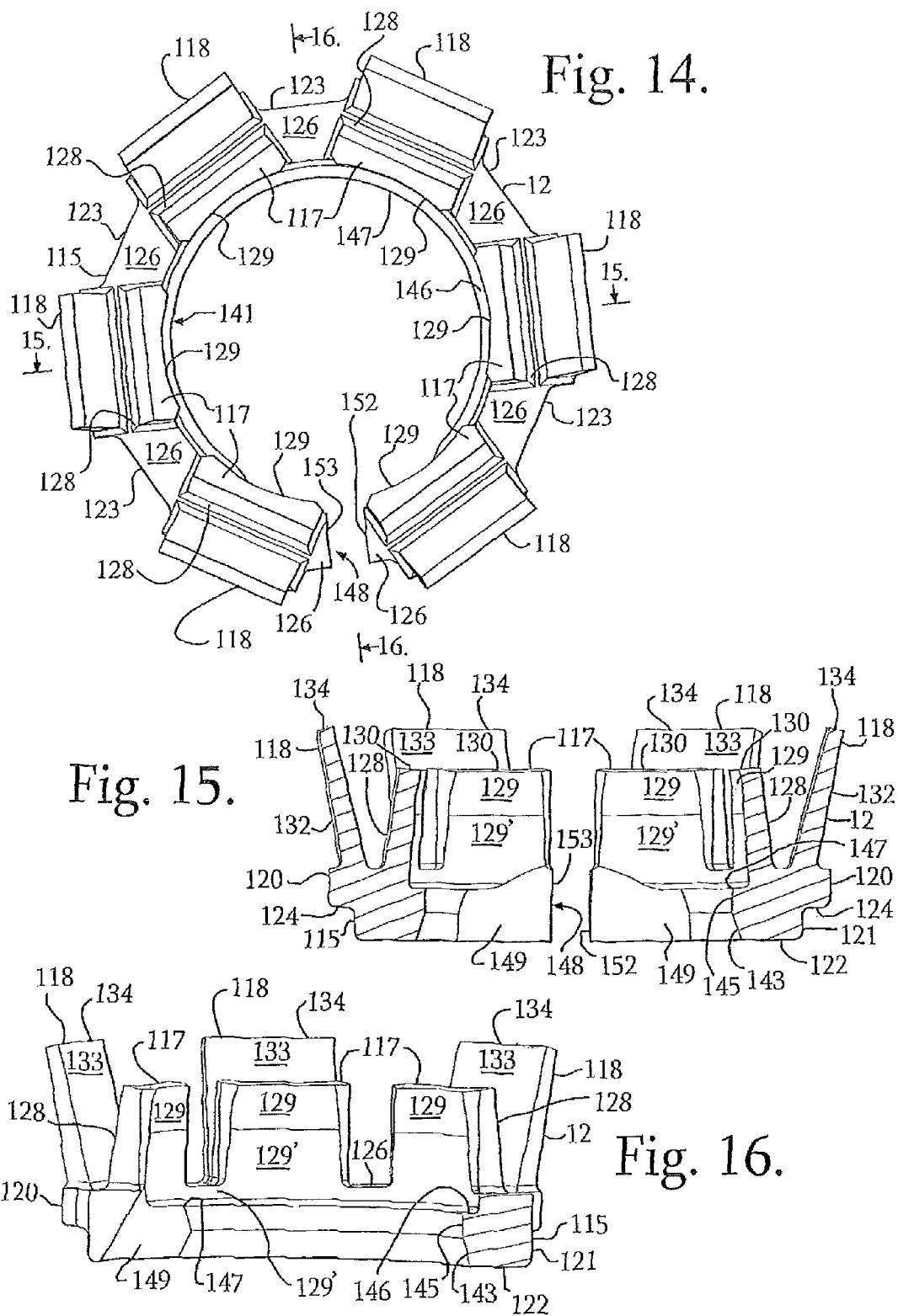

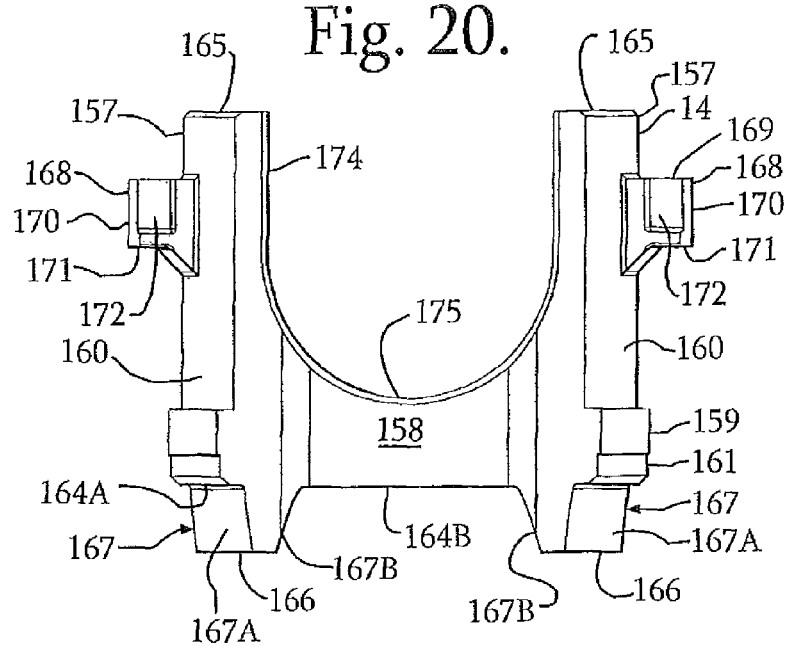
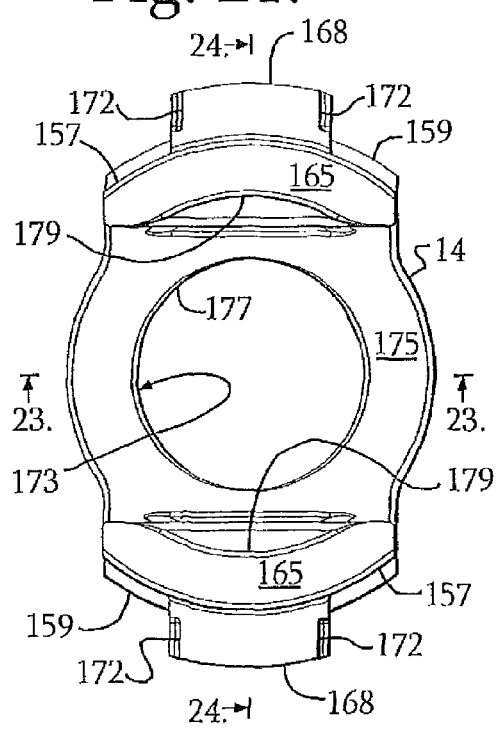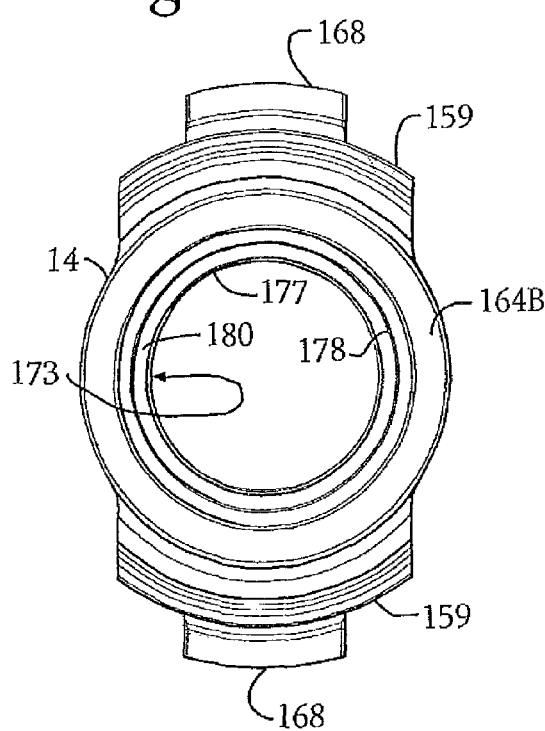

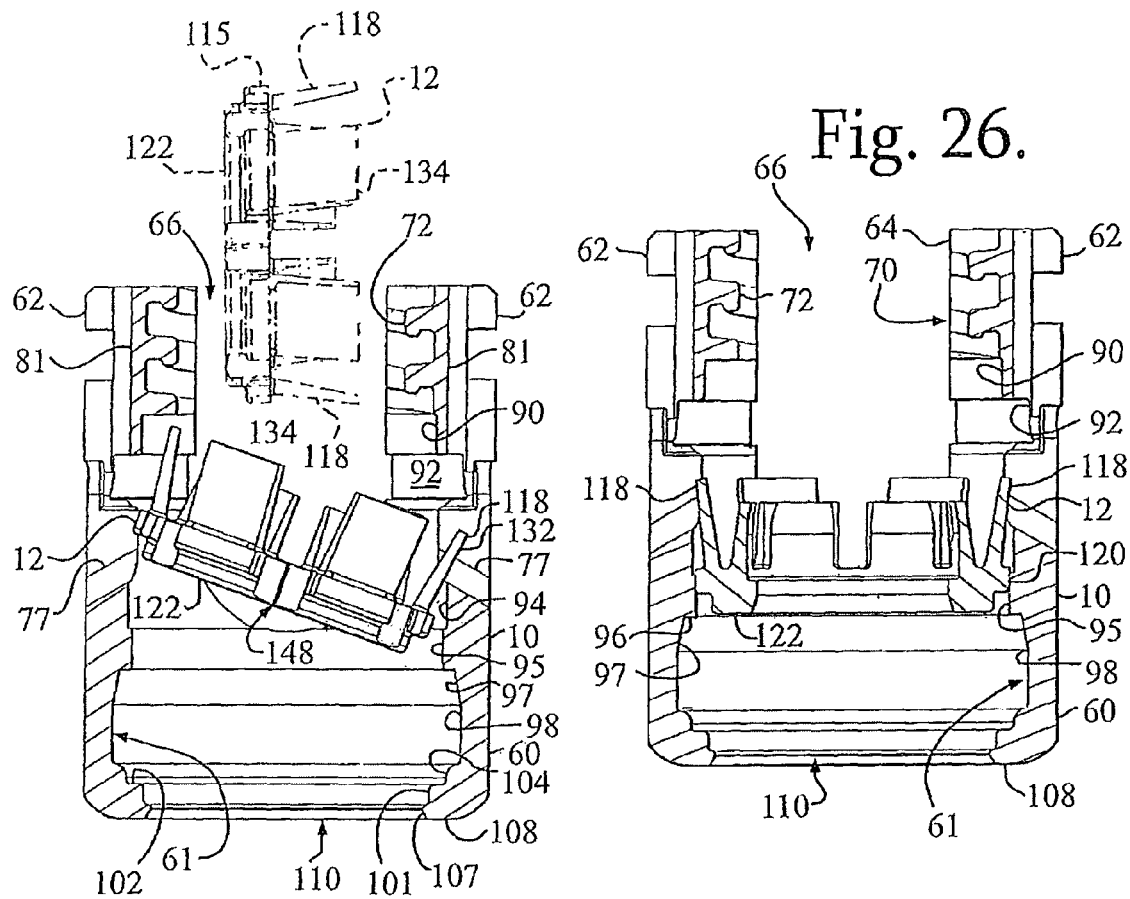
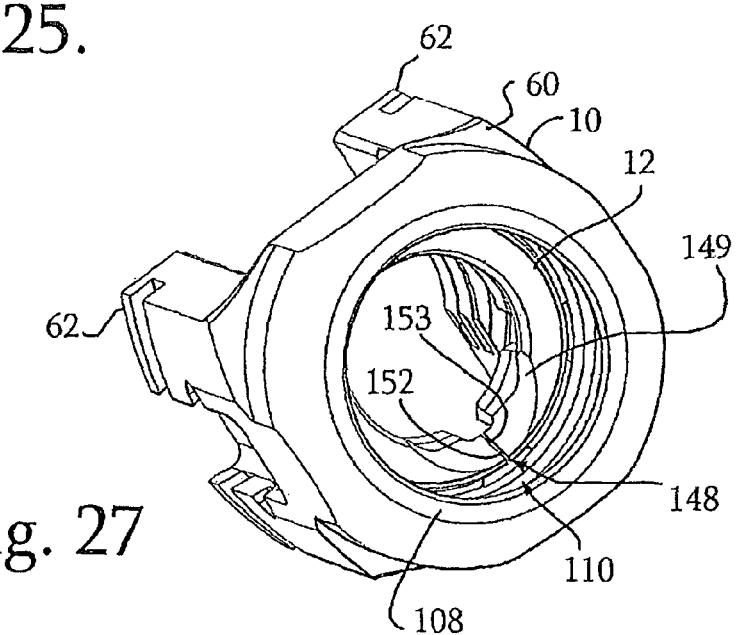

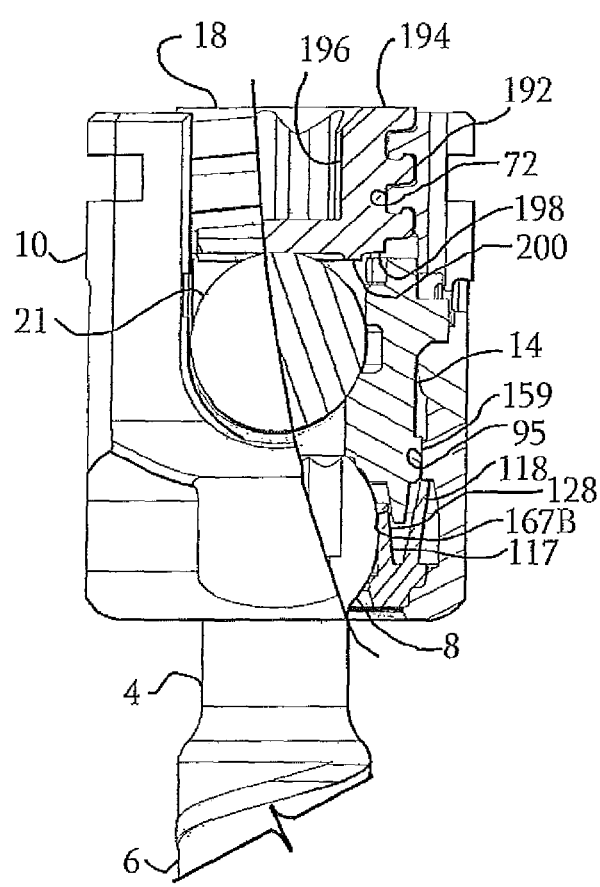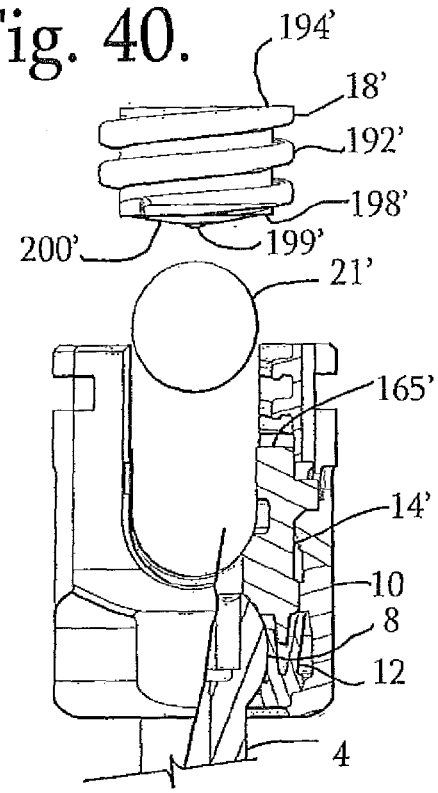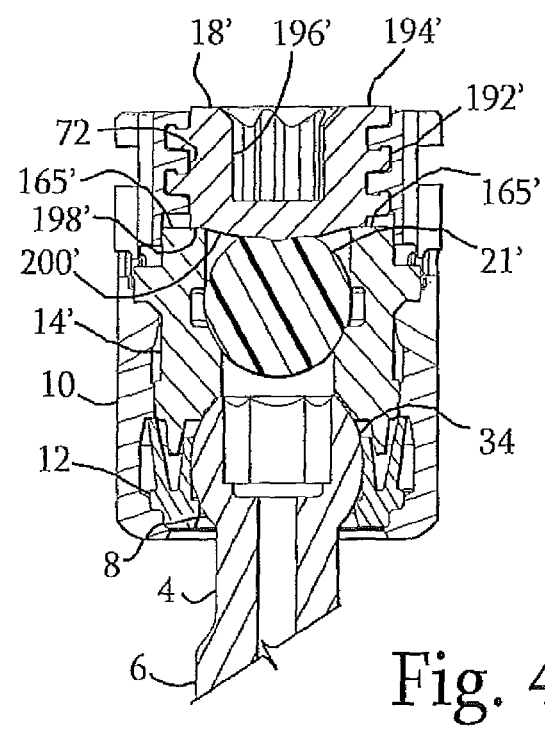

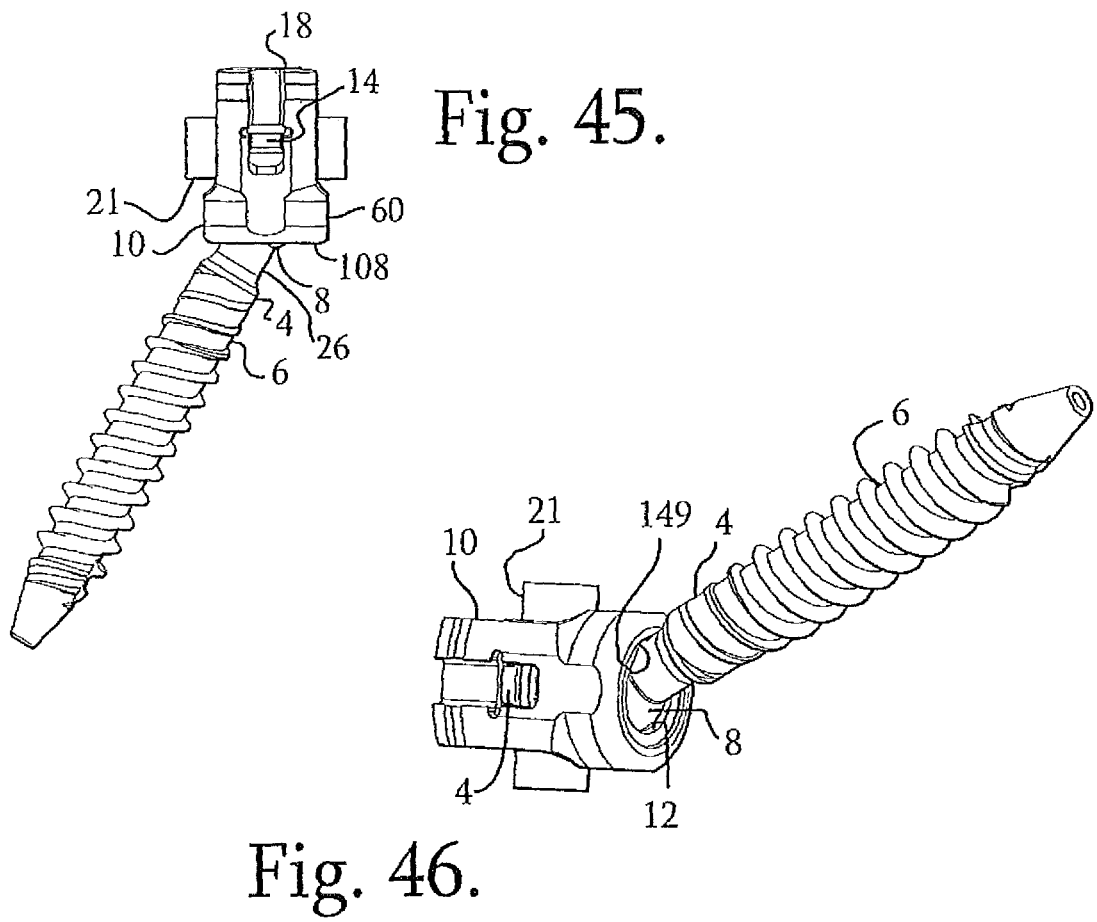
Fig. 45.
Fig. 46.
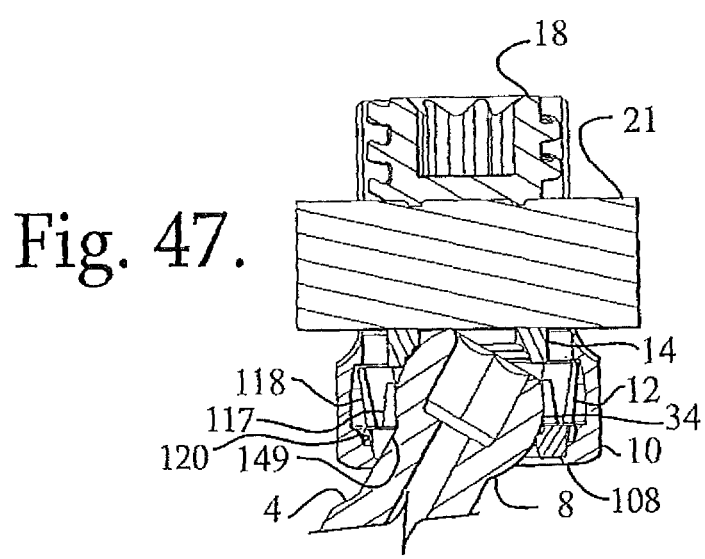
Fig. 47.

POLYAXIAL BONE ANCHOR WITH RETAINER WITH NOTCH FOR MONO-AXIAL MOTION

CROSS-REFERENCE TO RELATED APPLICATIONS

This application is a continuation of U.S. patent application Ser. No. 13/694,110, which claims the benefit of U.S. Provisional Patent Application Ser. No. 61/628,222 filed Oct. 26, 2011, each of which are incorporated by reference herein.

This application is also a continuation-in-part of U.S. patent application Ser. No. 13/896,842, filed May 17, 2013, which is a continuation of U.S. patent application Ser. No. 13/506,365, now U.S. Pat. No. 8,444,681, filed Apr. 13, 2012, which claimed the benefit of U.S. Provisional Patent Application Ser. No. 61/517,088, filed Apr. 13, 2011, each of which are incorporated by reference herein.

This application is a continuation in part of U.S. patent application Ser. No. 14/482,562, filed Sep. 10, 2014, which is a divisional of U.S. patent application Ser. No. 12/927,673, filed Nov. 19, 2010, which is a continuation of U.S. patent application Ser. No. 11/328,481, filed Jan. 9, 2006, which issued as U.S. Pat. No. 7,862,587 on Jan. 4, 2011, that is a continuation-in-part of U.S. patent application Ser. No. 11/272,508 filed Nov. 10, 2005, pending, that claims the benefit of U.S. Provisional Application No. 60/630,536 filed Nov. 23, 2004, each of which are incorporated by reference herein.

This application is also a continuation-in-part of U.S. patent application Ser. No. 13/573,874, filed Oct. 10, 2012, which claims the benefit of U.S. Provisional Patent Application Ser. No. 61/627,374, filed Oct. 11, 2011, each of which are incorporated by reference herein.

This application is also a continuation-in-part of U.S. patent application Ser. No. 14/061,393, filed Oct. 23, 2013 that claims the benefit of U.S. Provisional Patent Application Ser. Nos. 61/851,223, filed Mar. 4, 2013, and 61/795,984, filed Oct. 31, 2012, each of which are incorporated by reference herein.

This application is also a continuation-in-part of U.S. patent application Ser. No. 13/573,516 filed Sep. 19, 2012 that claims the benefit of U.S. Provisional Patent Application Ser. No. 61/626,250 filed Sep. 23, 2011, both of which are incorporated by reference herein.

This application is also a continuation-in-part of U.S. patent application Ser. No. 13/573,303 filed Sep. 7, 2012 that claims the benefit of U.S. Provisional Patent Application Ser. No. 61/573,508 filed Sep. 7, 2011, both of which are incorporated by reference herein.

This application is also a continuation-in-part of U.S. patent application Ser. No. 13/506,365 filed Apr. 13, 2012 that claims the benefit of U.S. Provisional Patent Application Ser. No. 61/517,088 filed Apr. 13, 2011, both of which are incorporated by reference herein.

This application is also a continuation-in-part of U.S. patent application Ser. No. 13/385,212 filed Feb. 8, 2012 that claims the benefit of U.S. Provisional Patent Application Ser. No. 61/463,037 filed Feb. 11, 2011, both of which are incorporated by reference herein.

This application is also a continuation-in-part of U.S. patent application Ser. No. 13/374,439 filed Dec. 29, 2011 is incorporated by reference herein.

This application is also an continuation-in-part of U.S. patent application Ser. No. 13/373,289, filed Nov. 9, 2011 that claims the benefit of U.S. Provisional Patent Application Ser. No. 61/456,649 filed Nov. 10, 2010 and Provisional Patent Application Ser. No. 61/460,234 filed Dec. 29, 2010, all of which are incorporated by reference herein.

This application is also a continuation-in-part of U.S. patent application Ser. No. 13/136,331 filed Jul. 28, 2011 that claims the benefit of U.S. Provisional Patent Application Ser. Nos. 61/400,504 filed Jul. 29, 2010, and 61/403,915 filed Sep. 23, 2010, all of which are incorporated by reference herein.

This application is also a continuation-in-part of U.S. patent application Ser. No. 12/924,802 filed Oct. 5, 2010 that claims the benefit of the following U.S. Provisional Patent Application Ser. Nos. 61/278,240, filed Oct. 5, 2009; 61/336,911, filed Jan. 28, 2010; 61/343,737 filed May 3, 2010; 61/395,564 filed May 14, 2010; 61/395,752 filed May 17, 2010; 61/396,390 filed May 26, 2010; 61/398,807 filed Jul. 1, 2010; 61/400,504 filed Jul. 29, 2010; 61/402,959 filed Sep. 8, 2010; 61/403,696 filed Sep. 20, 2010; and 61/403,915 filed Sep. 23, 2010, all of which are incorporated by reference herein.

This application is also a continuation-in-part of U.S. patent application Ser. No. 12/802,849 filed Jun. 15, 2010 that claims the benefit of the following U.S. Provisional Patent Application Ser. Nos. 61/268,708 filed Jun. 15, 2009; 61/270,754, filed Jul. 13, 2009; 61/336,911 filed Jan. 28, 2010; 61/395,564 filed May 14, 2010; 61/395,752 filed May 17, 2010; and 61/396,390 filed May 26, 2010, all of which are incorporated by reference herein.

BACKGROUND OF THE INVENTION

The present invention is directed to polyaxial bone screws for use in bone surgery, particularly spinal surgery and particularly to such screws with compression or pressure inserts and expansion lock split retainers to snap over, capture and retain the bone screw shank head in the receiver member assembly and later fix the bone screw shank with respect to the receiver assembly.

Bone screws are utilized in many types of spinal surgery in order to secure various implants to vertebrae along the spinal column for the purpose of stabilizing and/or adjusting spinal alignment. Although both closed-ended and open-ended bone screws are known, open-ended screws are particularly well suited for connections to rods and connector arms, because such rods or arms do not need to be passed through a closed bore, but rather can be laid or urged into an open channel within a receiver or head of such a screw. Generally, the screws must be inserted into the bone as an integral unit along with the head, or as a preassembled unit in the form of a shank and pivotal receiver, such as a polyaxial bone screw assembly.

Typical open-ended bone screws include a threaded shank with a pair of parallel projecting branches or arms which form a yoke with a U-shaped slot or channel to receive a rod. Hooks and other types of connectors, as are used in spinal fixation techniques, may also include similar open ends for receiving rods or portions of other fixation and stabilization structure.

A common approach for providing vertebral column support is to implant bone screws into certain bones which then in turn support a longitudinal structure such as a rod, or are supported by such a rod. Bone screws of this type may have a fixed head or receiver relative to a shank thereof, or may be of a polyaxial screw nature. In the fixed bone screws, the rod receiver head cannot be moved relative to the shank and the rod must be favorably positioned in order for it to be placed within the receiver head. This is sometimes very difficult or impossible to do. Therefore, polyaxial bone screws are commonly preferred. Open-ended polyaxial bone screws typically allow for a loose or floppy rotation of the head or receiver about the shank until a desired rotational position of the receiver is achieved by fixing such position relative to the shank during a final stage of a medical procedure when a rod or other longitudinal connecting member is inserted into the receiver, followed by a locking screw or other closure. This floppy feature can be, in some cases, undesirable and make the procedure more difficult. Also, it is often desirable to insert the bone screw shank separate from the receiver or head due to its bulk which can get in the way of what the surgeon needs to do. Such screws that allow for this capability are sometimes referred to as modular polyaxial screws.

With specific reference to modular snap-on or pop-on polyaxial pedicle screw systems having shank receiver assemblies, the prior art has shown and taught the concept of the receiver and certain retainer parts forming an assembly wherein a contractile locking engagement between the parts is created to fix the shank head with respect to the receiver and retainer. The receiver and shank head retainer assemblies in the prior art have included a slotted contractile retainer ring and/or a lower pressure slotted insert with an expansion and contraction collet-type of structure having contractile locking engagement for the shank head due to direct contact between the retainer and/or the collet structure with the receiver resulting in contraction of the slotted retainer ring and/or the collet-type structure of the insert against the shank head. The receiver and slotted insert have generally included tapered locking engagement surfaces.

The prior art for modular polyaxial screw assemblies has also shown and taught that the contact surfaces on the outside of the slotted collet and/or retainer and the inside of the receiver, in addition to being tapered, can be conical, radiused, spherical, curvate, multi-curvate, rounded, as well as other configurations to create a contractile type of locking engagement for the shank head with respect to the receiver.

In addition, the prior art for modular polyaxial screw assemblies has shown and taught that the shank head can both enter and escape from a collet-like structure on the insert or from the retainer when the insert or retainer is in the up position and within an expansion recess or chamber of the receiver. This is the case unless the slotted insert and/or the slotted retainer are blocked or constrained from being able to be pushed or manipulated back up into the receiver bore or cavity, or unless the screw assemblies are otherwise uniquely configured to prevent this from happening.

SUMMARY OF THE INVENTION

The present invention differentiates from the prior art by not allowing the receiver to be removed from the shank head once the parts are snapped-on and connected. This is true even if the retainer can go back up into the expansion chamber. This approach or design has been found to be more secure and to provide more resistance to pull-out forces compared to the prior art for modular polyaxial screw designs. The present invention also differentiates from the prior art by providing a split retainer ring characterized by a base portion providing expansion to receive and capture the shank head and then having expansion (not contraction) locking engagement between the shank head and the retainer ring base and between the retainer ring base and horizontal and vertical loading surfaces near a bottom opening of the receiver. The expansion-only retainer ring base portion of an embodiment according to the present invention is positioned entirely below the shank head hemisphere in the receiver and can be a stronger, more substantial structure to resist larger pull out forces on the assembly. The retainer ring base can also be better supported on a generally horizontal loading surface near the lower opening in the bottom of the receiver. This design has been found to be stronger and more secure when compared to that of the prior art which uses some type of contractile locking engagement between the parts, as described above; and, again, once assembled it cannot be disassembled.

Thus, a polyaxial bone screw assembly embodiments according to the invention includes a shank having an integral upper portion or integral radiused or spherical head and a body for fixation to a bone; a separate receiver defining an upper open channel, a central bore, a lower cavity and a lower opening; a top drop and turn in place lower compression insert; and a friction fit resilient expansion locking split retainer for capturing the shank head in the receiver lower cavity, the shank head being frictionally engaged with, but still movable in a non-floppy manner with respect to the friction fit retainer and the receiver prior to locking of the shank into a desired configuration. The shank is finally locked into a fixed position relative to the receiver by frictional engagement between the insert and a lower split ring-like portion of the retainer, as described previously, due to a downward force placed on the compression insert by a closure top pressing on a rod, or other longitudinal connecting member, captured within the receiver bore and channel. In the illustrated embodiments, retainers and compression inserts are downloaded into the receiver, but uploaded embodiments are also foreseen. The shank head can be positioned into the receiver lower cavity at the lower opening thereof prior to or after insertion of the shank into bone. In some embodiments, the compression insert may include a lock and release feature for independent locking of the polyaxial mechanism so the screw can be used like a fixed monoaxial screw. The insert may also include a sub-structure that advantageously presses upon a portion of the retainer during final locking. Also, in some embodiments, the shank (as well as other components of the assembly, including the closure top) can be cannulated for minimally invasive surgery applications. The retainer includes upwardly extending tangs that are deployed in the receiver cavity so that the retainer and captured shank head are stabilized and retained in the region of the receiver locking chamber once, but are free to rotate within the cavity. In this way, the shank head and retainer are partially constrained and cannot go back up into the receiver cavity, but can be manipulated there-within.

Again, a pre-assembled receiver, compression insert and friction fit split retainer may be "pushed-on", "snapped-on" or "popped-on" to the shank head prior to or after implantation of the shank into a vertebra. Such a "snapping on" procedure includes the steps of uploading the shank head into the receiver lower opening, the shank head pressing against the base portion of the split retainer ring and expanding the resilient lower open retainer portion out into an expansion portion or chamber of the receiver cavity followed by an elastic return of the retainer back to a nominal or near nominal shape thereof after the hemisphere of the shank head or upper portion passes through the lower ring-like portion of the retainer. The shank head enters into friction fit engagement with portions of the retainer, defined at least in part, by inner tangs of the retainer. The retainer snapping onto the shank head as the retainer returns to a neutral or close to neutral orientation, providing a non-floppy connection between the retainer and the shank head.

In the illustrated embodiments, when the shank is ultimately locked between the compression insert and the lower portion of the retainer, at least one lower, inner retainer edge surface locks against the shank head. The inner retainer tangs that would otherwise move away from the shank head during locking of the polyaxial mechanism are instead pressed toward the head by the downwardly moving insert substructure. The final fixation occurs as a result of a locking expansion-type of contact between the shank head and the lower edge portion of the split retainer and an expansion-type of non-tapered locking engagement between the lower portion of the retainer ring and the locking chamber in the lower portion of the receiver cavity. The retainer can expand more in the upper portion or expansion chamber of the receiver cavity to allow the shank head to pass through, but has restricted expansion to retain the shank head when the retainer lower ring portion is against the locking chamber surfaces in the lower portion of the receiver cavity and the shank head is forced down against the retainer ring during final locking. In some embodiments, when the polyaxial mechanism is locked, the pressure or compression insert is forced or wedged against a surface of the receiver resulting in an interference locking engagement, allowing for adjustment or removal of the rod or other connecting member without loss of a desired angular relationship between the shank and the receiver. This independent locking feature allows the polyaxial screw to function like a fixed monoaxial screw.

The lower pressure insert may also be configured to be independently locked by a tool or instrument, thereby allowing the pop-on polyaxial screw to be distracted, compressed and/or rotated along and around the rod to provide for improved spinal correction techniques. Such a tool engages the receiver from the sides and then engages outwardly extending winged arms of the insert to force or wedge the insert down into a locked position within the receiver. With the tool still in place and the correction maintained, the rod is then locked within the receiver channel by a closure top followed by removal of the tool. This process may involve multiple screws all being manipulated simultaneously with multiple tools to achieve the desired correction.

Objects of the invention further include providing apparatus and methods that are easy to use and especially adapted for the intended use thereof and wherein the tools are comparatively inexpensive to produce. Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is an exploded perspective view of an embodiment of a polyaxial bone screw assembly according to the present invention including a shank, a receiver, an open friction fit retainer and a top drop and turn in place lower compression insert, further shown with a portion of a longitudinal connecting member in the form of a rod and a closure top.

FIG. 2 is an enlarged top plan view of the shank of FIG. 1.

FIG. 3 is a reduced cross-sectional view taken along the line 3-3 of FIG. 2.

FIG. 14 is a top view of the retainer of FIG. 11.

FIG. 15 is an enlarged cross-sectional view taken along the line 15-15 of FIG. 14.

FIG. 16 is an enlarged cross-sectional view taken along the line 16-16 of FIG. 14.

FIG. 20 is a front elevational view of the insert of FIG. 17.

FIG. 21 is a top plan view of the insert of FIG. 17.

FIG. 22 is a bottom plan view of the insert of FIG. 17.

FIG. 25 is an enlarged front elevational view of the retainer and receiver of FIG. 1 with portions of the receiver broken away to show the detail thereof, the retainer being shown downloaded into the receiver (in phantom) to a tipped, partially inserted stage of assembly.

FIG. 26 is a front elevational view of the retainer and receiver with portions broken away, similar to what is shown in FIG. 25, showing the retainer in a subsequent stage of assembly and in a maximum state of compression.

FIG. 27 is a partial bottom perspective view of the receiver and retainer of FIG. 26.

FIG. 39 is an enlarged and partial front elevational view with portions broken away, similar to FIG. 37, the insert being shown pushed down into a fully seated position within the lower receiver cavity by pressure being placed thereon from above by the rod and closure top, the insert being placed in locking interference fit with the receiver and also pressing against inner tangs of the retainer.

FIG. 40 is a reduced and partial front elevational view with portions broken away, similar to FIG. 39, but with the rod and closure top removed and a locking insert keeping the shank locked in place, the figure showing an alternative locking insert, a deformable rod and cooperating closure top being installed in the receiver.

FIG. 41 is an enlarged and partial front elevational view with portions broken away, similar to FIG. 39, showing the alternative rod and closure top fixed to the receiver.

FIG. 45 is an enlarged side elevational view of the assembly of FIG. 1, shown fully assembled with the shank disposed at a thirty degree (caudad) angle with respect to the receiver.

FIG. 46 is a perspective view of the assembly of FIG. 45.

FIG. 47 is an enlarged and partial side elevational view of the assembly of FIG. 45 with portions broken away to show the detail thereof.

DETAILED DESCRIPTION OF THE INVENTION

Figure 4:
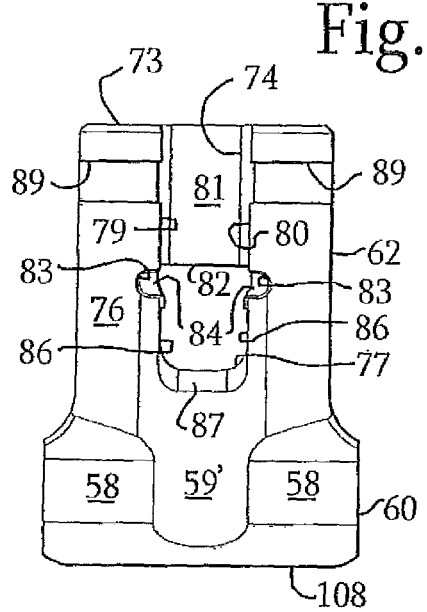
FIG. 4 is an enlarged side elevational view of the receiver of FIG. 1.
Figure 5:
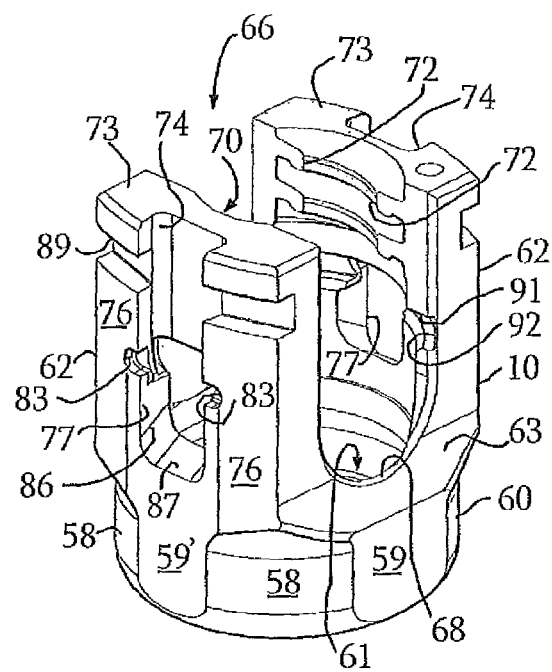
FIG. 5 is a perspective view of the receiver of FIG. 4.
Figure 6:
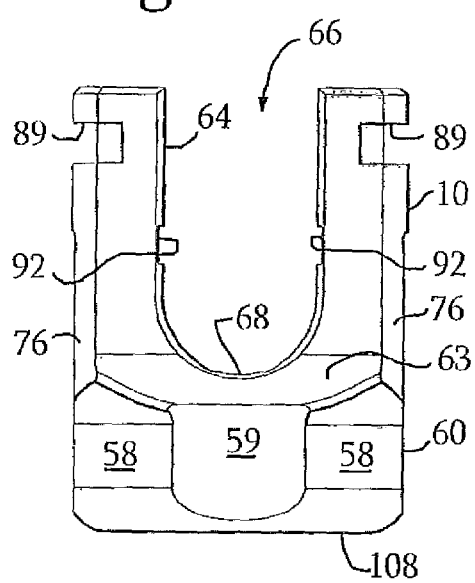
FIG. 6 is a front elevational view of the receiver of FIG. 4.
Figure 7:
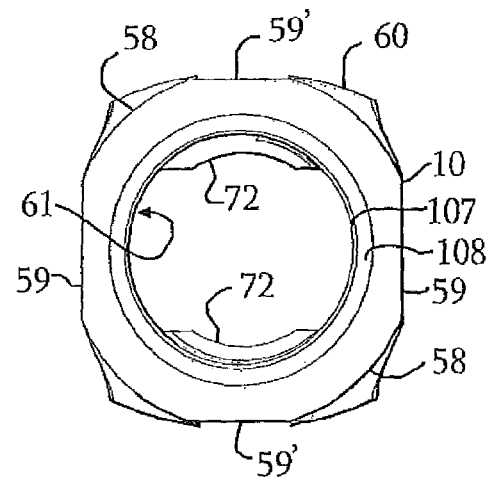
FIG. 7 is a bottom plan view of the receiver of FIG. 4.
Figure 8:
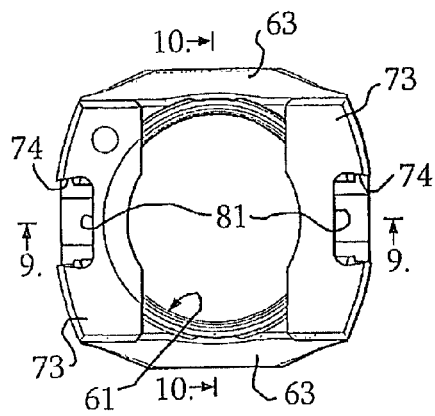
FIG. 8 is a top plan view of the receiver of FIG. 4.
Figure 9:
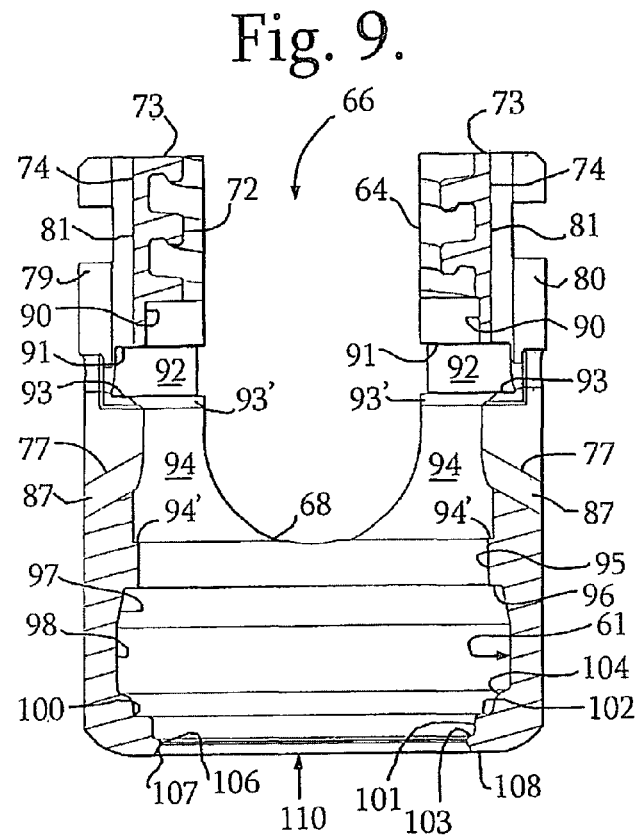
FIG. 9 is a cross-sectional view taken along the line 9-9 of FIG. 8.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. It is also noted that any reference to the words top, bottom, up and down, and the like, in this application refers to the alignment shown in the various drawings, as well as the normal connotations applied to such devices, and is not intended to restrict positioning of the bone attachment structures in actual use.

With reference to FIGS. 1-47, the reference number 1 generally represents a polyaxial bone screw apparatus or assembly according to an embodiment of the present invention. The assembly 1 includes a shank 4, that further includes a body 6 integral with an upwardly extending upper portion or head 8; a receiver 10; a friction fit retainer 12, and a crown-like compression or pressure insert 14. The receiver 10, retainer 12 and compression insert 14 are initially assembled and may be further assembled with the shank 4 either prior or subsequent to implantation of the shank body 6 into a vertebra 17, as will be described in greater detail below. FIGS. 1 and 37-39 further show a closure structure 18 for capturing a longitudinal connecting member, for example, a rod 21 which in turn engages the compression insert 14 that presses against the shank head 8 into fixed frictional contact with the retainer 12, so as to capture, and fix the longitudinal connecting member 21 within the receiver 10 and thus fix the member 21 relative to the vertebra 17. The receiver 10 and the shank 4 cooperate in such a manner that the receiver 10 and the shank 4 can be secured at any of a plurality of angles, articulations or rotational alignments relative to one another and within a selected range of angles both from side to side and from front to rear, to enable flexible or articulated engagement of the receiver 10 with the shank 4 until both are locked or fixed relative to each other near the end of an implantation procedure. The illustrated rod 21 is hard, stiff, non-elastic and cylindrical, having an outer cylindrical surface 22. In some embodiments, the rod 21 may be elastic, deformable and/or of different materials and cross-sectional geometries (see, e.g., FIGS. 40 and 41). As shown in FIG. 41, in some embodiments of the invention, the closure top presses directly on the insert 14, for example, when the rod is deformable.

Figure 31:
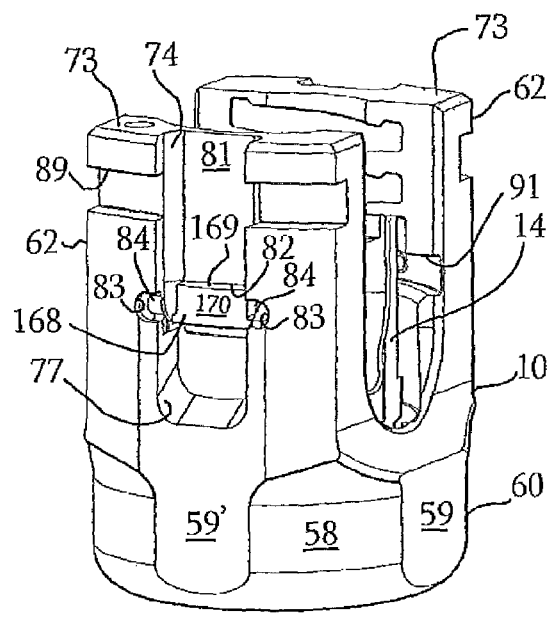
FIG. 31 is a perspective view of the retainer, receiver and insert of FIG. 30 showing the insert rotated into a desired position for assembly with the shank of FIG. 1 and showing the receiver crimped against the insert.

The shank 4, best illustrated in FIGS. 1-3, is elongate, with the shank body 6 having a helically wound bone implantable thread 24 (single or dual lead thread form and different thread types) extending from near a neck 26 located adjacent to the upper portion or head 8, to a tip 28 of the body 6 and extending radially outwardly therefrom. During use, the body 6 utilizing the thread 24 for gripping and advancement is implanted into the vertebra 17 leading with the tip 28 and driven down into the vertebra with an installation or driving tool (not shown), so as to be implanted in the vertebra to a location at or near the neck 26, as shown in FIG. 31, for example, and more fully described in the paragraphs below. The shank 4 has an elongate axis of rotation generally identified by the reference letter A.

The neck 26 extends axially upward from the shank body 6. The neck 26 may be of the same or is typically of a slightly reduced radius as compared to an adjacent upper end or top 32 of the body 6 where the thread 24 terminates. Further extending axially and outwardly from the neck 26 is the shank upper portion or head 8 that provides a connective or capture apparatus disposed at a distance from the upper end 32 and thus at a distance from the vertebra 17 when the body 6 is implanted in such vertebra.

The shank upper portion 8 is configured for a pivotable connection between the shank 4 and the retainer 12 and receiver 10 prior to fixing of the shank 4 in a desired position with respect to the receiver 10. The shank upper portion 8 has an outer, convex and substantially spherical surface 34 that extends outwardly and upwardly from the neck 26 that terminates at a substantially annular, planar rim surface 38 that is perpendicular to the shank central axis A. In some embodiments, a frusto-conical surface extends from the spherical surface 34 inwardly to the top surface 38, providing additional clearance during pivoting of the shank with respect to the receiver 10 and the insert 14. The spherical surface 34 has an outer radius configured for temporary frictional, non-floppy, sliding cooperation with one or more edges and/or surfaces of the retainer 12, as well as ultimate frictional engagement with the retainer 12 at, at least one lower inner edge thereof and ultimate frictional engagement with the insert 14 at an inner partially spherical surface thereof and/or stepped or ridged surfaces thereof, as will be discussed more fully in the paragraphs below. In FIG. 1 and some of the other figures, a dotted line 40 designates a hemisphere of the spherical surface 34. The spherical surface 34 shown in the present embodiment is substantially smooth, but in some embodiments may include a roughening or other surface treatment and is sized and shaped for cooperation and ultimate frictional engagement with the compression insert 14 as well as ultimate frictional engagement with a lower ring-like edge of the retainer 12. The shank spherical surface 34 is locked into place exclusively by the insert 14 and the retainer 12 lower edged portion and not by inner surfaces defining the receiver cavity.

A counter sunk and stepped or graduated annular seating surface or base 45 partially defines a portion of an internal drive feature or imprint 46. In some embodiments of the invention, the surface 45 is substantially planar. The illustrated internal drive feature 46 is an aperture formed in the top 38 and has a hex shape designed to receive a tool (not shown) of an Allen wrench type, into the aperture for rotating and driving the bone screw shank 4 into the vertebra 17. It is foreseen that such an internal tool engagement structure may take a variety of tool-engaging forms and may include one or more apertures of various shapes, such as a pair of spaced apart apertures or a multi-lobular or star-shaped aperture. The graduated seat or base surfaces 45 of the drive feature 46 are disposed substantially perpendicular to the axis A with the drive feature 46 otherwise being coaxial with the axis A. As illustrated in FIGS. 2 and 3, the drive seat 45 having beveled or stepped surfaces advantageously further enhances gripping with the driving tool. In operation, the driving tool (not shown) is received in the internal drive feature 46, being seated at the base 45 and engaging the faces of the drive feature 46 for both driving and rotating the shank body 6 into the vertebra 17, either before or after the shank 4 is connected to the receiver 10 via the retainer 12, the driving tool extending into the receiver 10 when the shank 4, retainer 12 and receiver 10 combination is driven into the vertebra 17.

The shank 4 shown in the drawings is cannulated, having a small central bore 50 extending an entire length of the shank 4 along the axis A. The bore 50 is defined by an inner cylindrical wall of the shank 4 and has a circular opening at the shank tip 28 and an upper circular opening communicating with the external drive 46 at the driving seat 45. The bore 50 is coaxial with the threaded body 6 and the upper portion or head 8. The bore 50 provides a passage through the shank 4 interior for a length of wire (not shown) inserted into the vertebra 17 prior to the insertion of the shank body 6, the wire providing a guide for insertion of the shank body 6 into the vertebra 17. It is foreseen that the shank could be solid and made of different materials, including metal and non-metals.

To provide a biologically active interface with the bone, the threaded shank body 6 may be coated, perforated, made porous or otherwise treated. The treatment may include, but is not limited to a plasma spray coating or other type of coating of a metal or, for example, a calcium phosphate; or a roughening, perforation or indentation in the shank surface, such as by sputtering, sand blasting or acid etching, that allows for bony ingrowth or ongrowth. Certain metal coatings act as a scaffold for bone ingrowth. Bio-ceramic calcium phosphate coatings include, but are not limited to: alpha-tri-calcium phosphate and beta-tri-calcium phosphate $(Ca_3(PO_4)_2)$, tetra-calcium phosphate $(Ca_4P_2O_9)$, amorphous calcium phosphate and hydroxyapatite $(Ca_{10}(PO_4)_6(OH)_2)$. Coating with hydroxyapatite, for example, is desirable as hydroxyapatite is chemically similar to bone with respect to mineral content and has been identified as being bioactive and thus not only supportive of bone ingrowth, but actively taking part in bone bonding.

With particular reference to FIGS. 1 and 4-10, the receiver 10 has a generally U-shaped appearance with partially discontinuous cylindrical inner and outer profiles as well as planar and other curved surfaces. The receiver 10 has an axis of rotation B that is shown in FIG. 1 as being aligned with and the same as the axis of rotation A of the shank 4, such orientation being desirable, but not required during assembly of the receiver 10 with the shank 4. After the receiver 10 is pivotally attached to the shank 4, either before or after the shank 4 is implanted in a vertebra 17, the axis B is typically disposed at an angle with respect to the axis A, as shown, for example, in FIGS. 42-47.

The receiver 10 includes a base 60 with various curved surfaces 58, opposed outer planar surfaces 59, and opposed outer planar surfaces 59', the base 60 defining a bore or inner cavity, generally 61, the base 60 being integral with a pair of opposed upstanding arms 62. At the base 60, the planar surfaces 59 are located between the arms 62 and an inset surface portion 63 is located above and adjacent to each planar surface 59, each inset surface portion 63 spanning between the pair of arms 62. The arms 62 form a cradle and define a U-shaped channel 64 between the arms 62 with an upper opening, generally 66, and a U-shaped lower channel portion or seat 68, the channel 64 having a width for operably snugly receiving the rod 21 or portion of another longitudinal connector (or sleeve of a tensioned cord connecting member) between the arms 62, the channel 64 communicating with the base cavity 61. Inner opposed substantially planar arm surfaces 69 partially define the channel 64 above the curved seat 68 and partially define outer sides of each arm interior surface generally 70, that includes various inner cylindrical profiles, an upper one of which is a partial helically wound guide and advancement structure 72 located adjacent top surfaces 73 of each of the arms 62. In the illustrated embodiment, the guide and advancement structure 72 is a partial helically wound interlocking flangeform configured to mate under rotation with a similar structure on the closure structure 18, as described more fully below. However, it is foreseen that for certain embodiments of the invention, the guide and advancement structure 72 could alternatively be a square-shaped thread, a buttress thread, a reverse angle thread or other thread-like or non-thread-like helically wound discontinuous advancement structures, for operably guiding under rotation and advancing the closure structure 18 downward between the arms 62, as well as eventual torquing when the closure structure 18 abuts against the rod 21 or other longitudinal connecting member. It is foreseen that the arms 62 could have break-off extensions.

An opposed pair of vertically extending outer grooves, generally 74, running substantially parallel to the receiver axis B are centrally formed in outer curved convex surfaces 76 of the arms 62. Each groove 74 runs centrally from the respective arm top surface 73 and terminates at a a lower through aperture 77. Each aperture 77 extends through the respective arm surface 77 to the respective inner arm surface 70 and is located spaced from the receiver base 60. Each groove 74 has an upper opening partially defined by a pair of opposed surfaces 79 and 80 and a substantially planar outer wall surface 81 extending between the surfaces 79 and 80. The planar wall surface terminates at the top arm surface 73 and at a lower surface 82 partially defining the aperture 77. The opposed surfaces 79 and 80 are disposed at a slight angle with respect to each other, forming the groove 74 as a dovetail-like space for easily receiving an elongate tool (not shown) that enters into the groove 74 at the arm top surface 73 and is kept in close sliding contact with the surface 81 by the orientation of the surfaces 79 and 80 angling toward one another with the tool sliding along the surface 81 and ultimately into contact with winged portions of the insert 14 that extend through the aperture 77 as will be described in greater detail below. At the through aperture 77, the dovetail surfaces 79 and 80 terminate near facing generally c-shaped ears 83 that do not extend completely through the respective arm 62, but rather include a thin wall that provides a crimping portion or wall 84. The crimping portions or walls 84 are sized and shaped for pressing or crimping some or all of the wall material into grooves or arms surfaces adjacent to the wings of the insert 14 to prohibit rotation and misalignment of the insert 14 with respect to the receiver 10 as will be described in greater detail below. In other embodiments of the invention, other surfaces at or near the grooves 74 may be inwardly crimped.

The illustrated through aperture 77 located below each grooves 74 is substantially the same width as the groove 74 there-above, each aperture 77 being partially defined by a pair of opposed side walls 86 and a bottom surface 87, resulting in the aperture 77 having a substantially rectangular profile. Each surface 87 slants outwardly and downwardly from the inner arm surface 70 toward the receiver base 60 outer planar surface 59'. The through apertures 77 are sized and shaped for receiving tooling and also the outer tangs of the retainer 12 during assembly as shown, for example, in FIG. 25.

The receiver 10 is a one-piece or integral structure and is devoid of any spring tabs or collet-like structures. Preferably the insert and/or receiver are configured with structure for blocking rotation of the insert with respect to the receiver, such as the crimp walls 84, but allowing some up and down movement of the insert with respect to the receiver during the assembly and implant procedure. Also formed in each outer arm surface 76 near the top surface 73 is an undercut tool receiving and engaging groove 89. Some or all of the apertures and grooves described herein, including, but not limited to grooves 74, apertures 77, and grooves 89 may be used for holding the receiver 10 during assembly with the insert 14, the retainer 12 and the shank 4; during the implantation of the shank body 6 into a vertebra when the shank is pre-assembled with the receiver 10; during assembly of the bone anchor assembly 1 with the rod 21 and the closure structure 18; and during lock and release adjustment of inserts, with respect to the receiver 10, either into or out of frictional engagement with the inner surfaces of the receiver 10 as will be described in greater detail below. It is foreseen that tool receiving grooves or apertures may be configured in a variety of shapes and sizes and be disposed at other locations on the receiver arm 62 outer surfaces 76 and/or inner surfaces 70 as well as the base 60 outer or inner surfaces.

Figure 10:
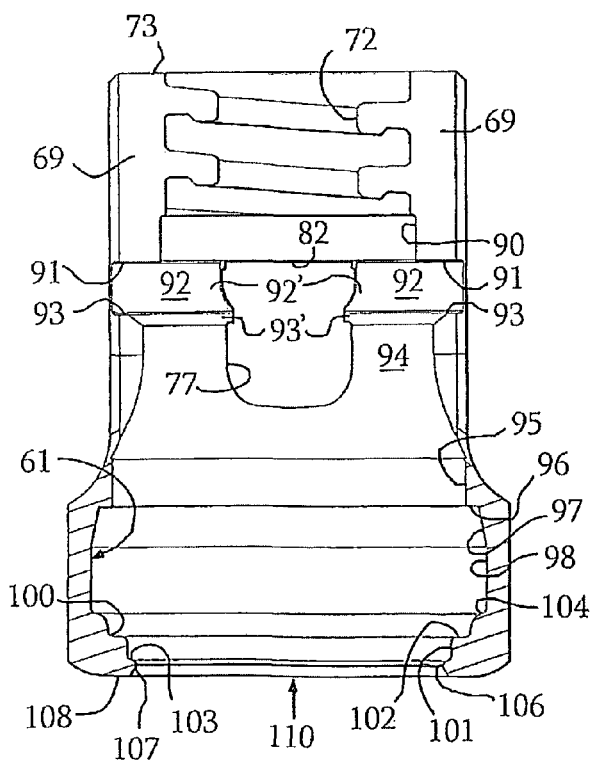
FIG. 10 is a cross-sectional view taken along the line 10-10 of FIG. 8.
Figure 11:
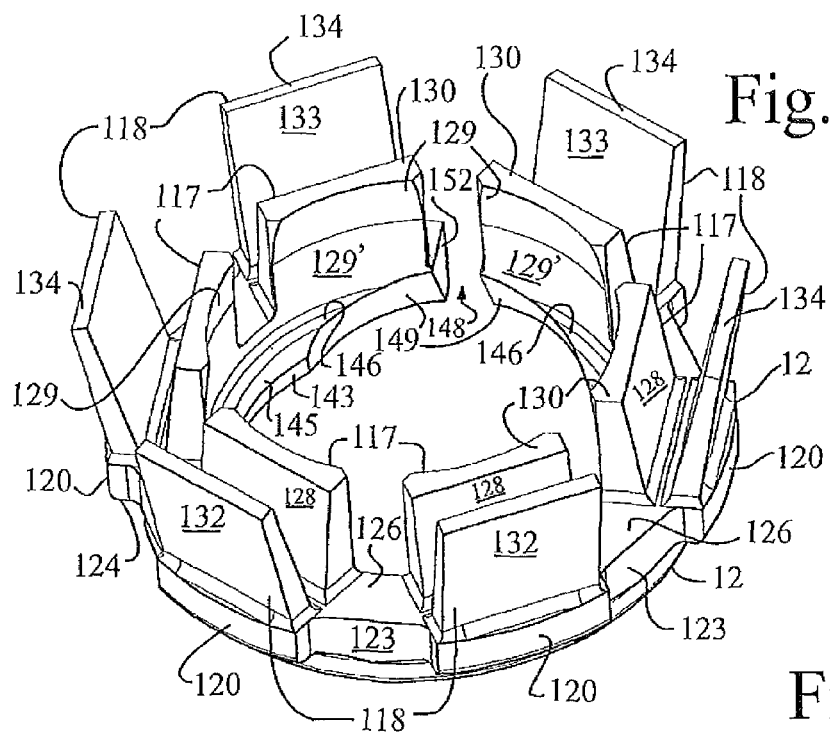
FIG. 11 is an enlarged perspective view of the retainer of FIG. 1.
Figure 12:
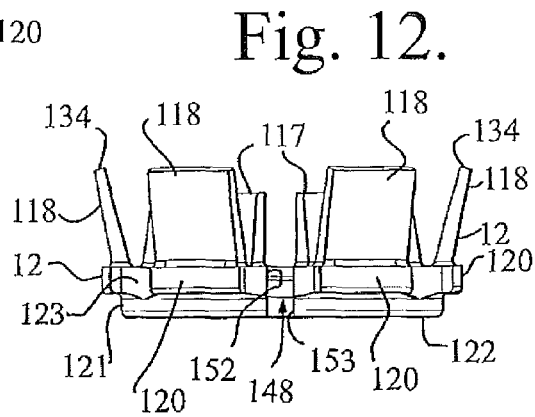
FIG. 12 is a front elevational view of the retainer of FIG. 11.
Figure 13:
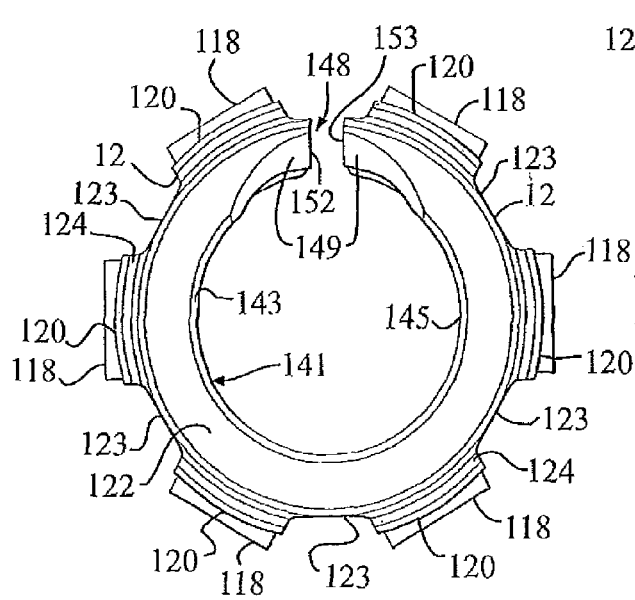
FIG. 13 is a bottom plan view of the retainer of FIG. 11.
Figure 17:
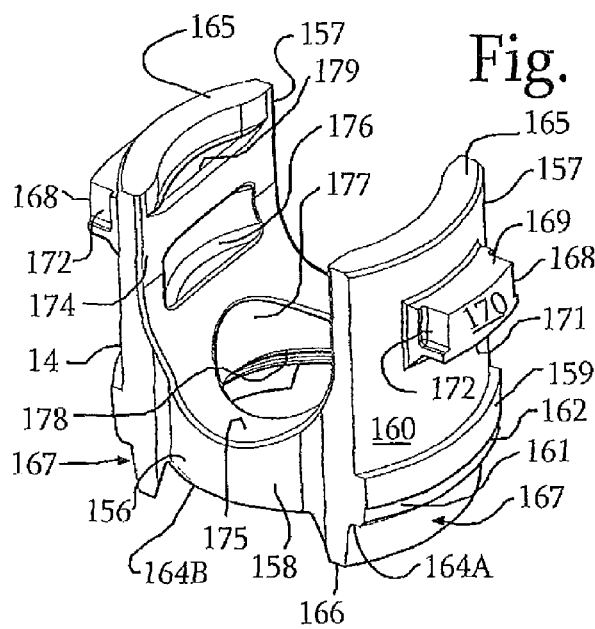
FIG. 17 is an enlarged perspective view of the insert of FIG. 1.
Figure 18:
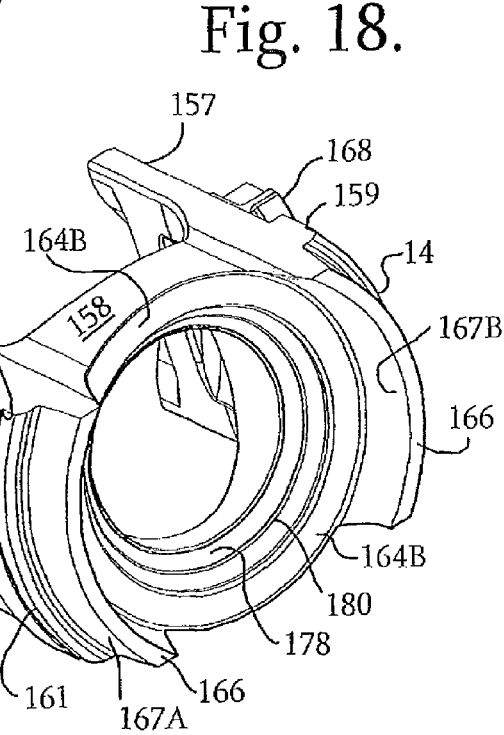
FIG. 18 is another perspective view of the insert of FIG. 17.
Figure 19:
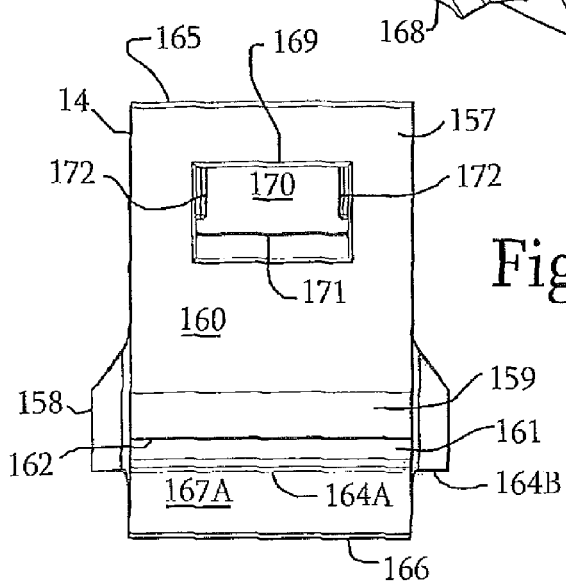
FIG. 19 is a side elevational view of the insert of FIG. 17.
Figure 23:
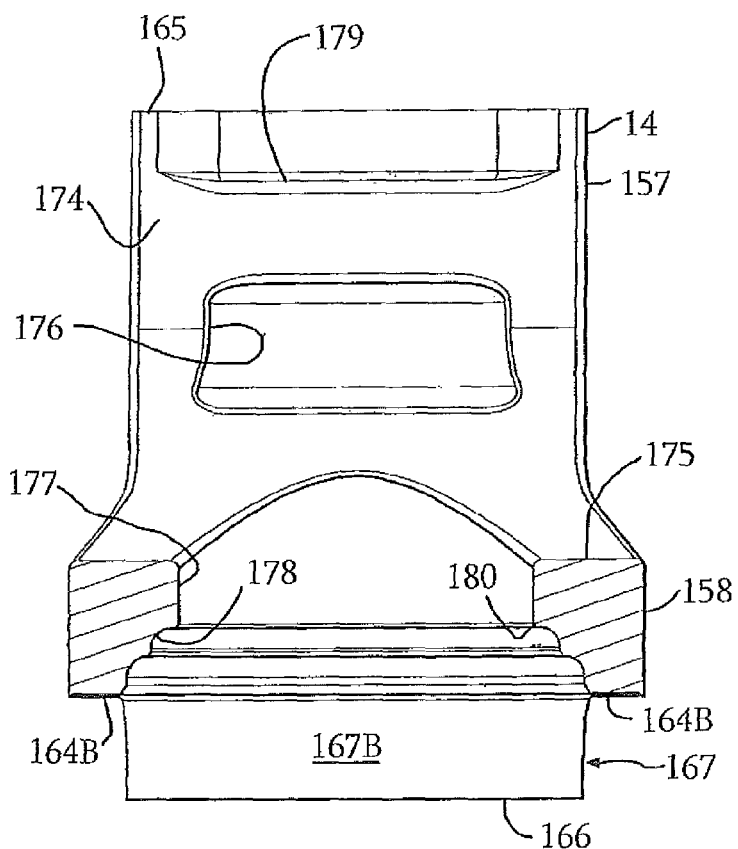
FIG. 23 is an enlarged cross-sectional view taken along the line 23-23 of FIG. 21.
Figure 24:
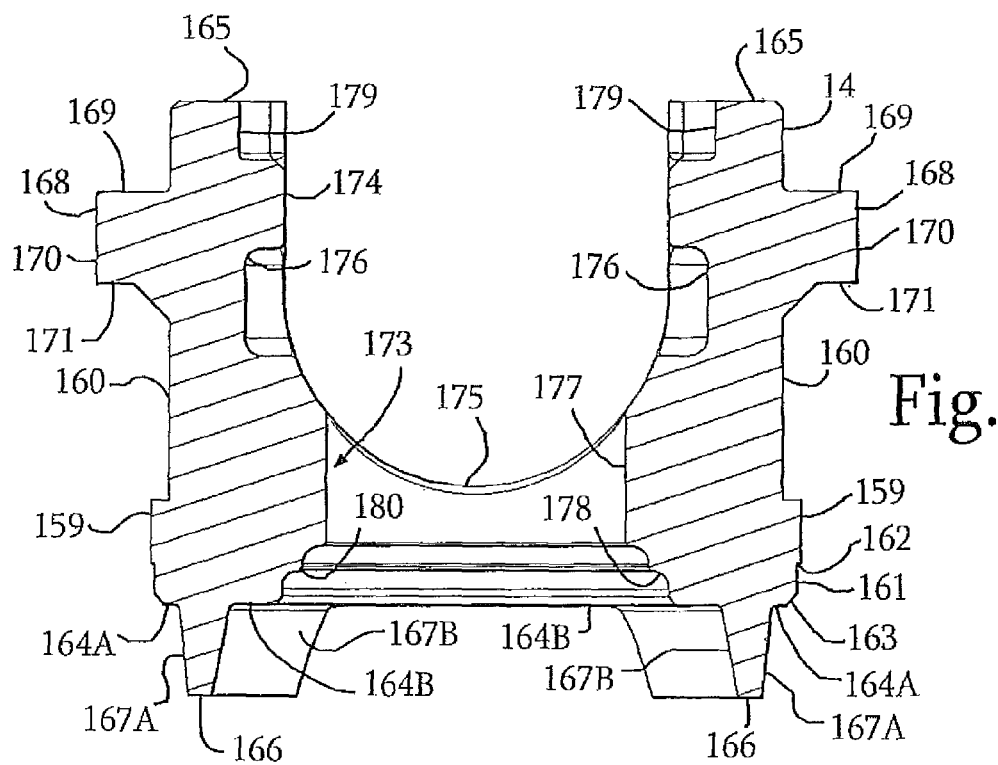
FIG. 24 is an enlarged cross-sectional view taken along the line 24-24 of FIG. 21.

Returning to the interior surface 70 of the receiver arms 62, located below the guide and advancement structure 72 is a discontinuous cylindrical surface 90 partially defining a run-out feature for the guide and advancement structure 72. Adjacent the surface 90 is a ledge or upper annular surface 91 that in turn is adjacent to another cylindrical surface 92 having a larger diameter than the cylindrical surface 90. As best shown in FIG. 10, the upper annular surface 91 includes the upper surface 82 that partially defines the aperture 77. The cylindrical surface 92 is sized and shaped to receive an upper winged portion of the insert 14 as will be described in greater detail below. Therefore, the surface 92 has a diameter greater than a greater diameter of the guide and advancement structure 72. The receiver 10 may further includes sloped, stepped or chamfered surfaces above and below the surface 92. The surface 92 is divided not only by the U-shaped channel 64, but also by each of the through apertures 77, resulting in the surface 92 being in four sections. At each aperture 77, the surface 92 includes a surface portion 92' that is located at the inside of ears 83 of the crimping wall portions 84, the surface portions 92' eventually in contact with the insert 14 as will be described below. A lower, substantially annular ledge 93 faces each upper ledge or annular surface 91 and is adjacent the cylindrical surface 92. An inwardly and downwardly sloping surface or chamfer 93' is adjacent to each surface 93 and also adjacent to another discontinuous cylindrical arm surface 94. Each cylindrical surface 94 has a diameter smaller than the surface 92 and extends all the way down to the U-shaped channel seat 68. A portion of each aperture 77 extends through each surface 94. A lower partially sloping or stepped ledge 94' at the base of the cylindrical surface 92 slopes downwardly toward the receiver base 60 and extends inwardly toward the axis B, the surface 94 terminating at a cylindrical surface 95 that extends completely around the receiver base 60 and thus runs beneath each arm 62 and is adjacent to the lower seat 68. The inner surface 95 thus defines an upper and inner portion of the receiver base 60. The cylindrical surface has a diameter slightly smaller than the diameter of the surface 94. The surface 95 terminates at a ledge surface or chamber ceiling 96 that extends outwardly away from the axis B, the surface 96 being substantially perpendicular to the axis B, but could be oblique. The surface 96 is annular and defines an upper ceiling or stop of a retainer ring expansion portion or chamber of the inner cavity 61 that is further defined by an adjacent outwardly sloping surface 97 and a cylindrical surface 98 that is adjacent the surface 97. The surface 97 also acts as a stop for and slidingly cooperates with outwardly and upwardly projecting retainer tangs or panels as will be described in greater detail below. The cylindrical surface 98 has a diameter greater than the diameter of the cylindrical surface 95. The cylindrical surfaces 92, 95 and 98 are all centrally aligned with and run parallel to the receiver axis B. The surface 98 defines a circumferential recess that is sized and shaped to receive the retainer 12 as it expands around the shank upper portion 8 as the shank 8 moves upwardly toward the channel 64 during assembly. It is foreseen that the recess could be tapered or conical in configuration.

Figure 37:
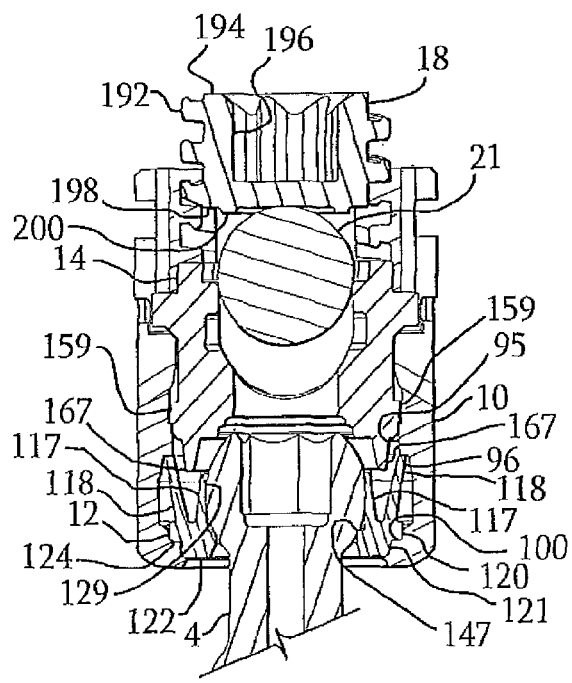
FIG. 37 is an enlarged and partial front elevational view with portions broken away, similar to FIG. 36, the shank upper portion with attached retainer being shown pulled down into a seated position within the lower receiver cavity, the retainer outer tangs in a substantially neutral state, extending outwardly and captured beneath a surface of the receiver, further shown is the rod and closure top of FIG. 1, also shown in an enlarged and partial front elevational view with portions broken away to show the detail thereof.
Figure 38:
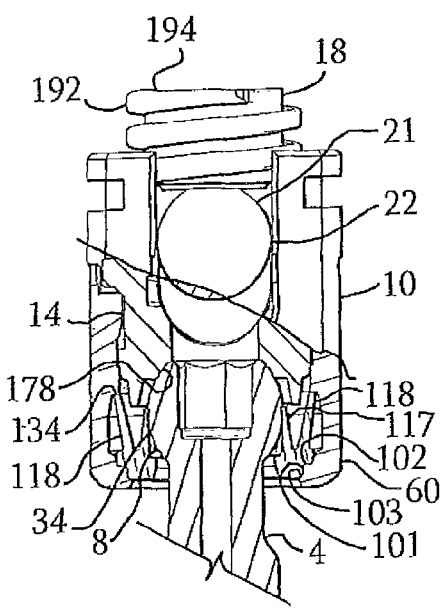
FIG. 38 is a reduced and partial front elevational view with portions broken away, similar to FIG. 37, the shank being shown in a maximum possible pushed up position prior to locking with the rod and closure top.

A pair of cylindrical surfaces 100 and 101 with an annular step surface 102 therebetween as well as a lower annular step 103 located below and adjacent to the surface 101 provide a lower seat for the retainer 12 as will be described in greater detail below. The surfaces 102 and 103 are substantially perpendicular to the surfaces 100 and 101 and the receiver axis B. The surfaces 100, 101, 102 and 103 are located below the cylindrical surface 98 in the lower part of the base 60 and are sized and shaped to closely receive and surround a lower base portion and lower skirt or substructure of the retainer 12 when the retainer is in a nominal or reduced deployment position as shown in FIGS. 37-39, for example. Thus, the cylindrical surface 101 has a diameter smaller than the diameter of the cylindrical surface 98 that defines the expansion area or expansion chamber for the retainer 12. The surface 101 is joined or connected to the surface 98 by one or more beveled, curved or conical transition step surfaces 104. The surfaces 104 allow for sliding and nominal or deployment positioning of the retainer 12 into the space defined by the surfaces 100 and 101 and ultimate seating of the retainer 12 on the lower substantially horizontal annular surfaces 102 and 103.

Located below and adjacent to the annular seating surface 103 is a lower edge or rim surface 106 that communicates with a beveled or flared bottom opening surface 107, the surface 107 communicating with an exterior base or bottom surface 108 of the base 60, defining a lower opening, generally 110, into the base cavity 61 of the receiver 10. In some embodiments of the invention, it is foreseen that one or more curvate cut-out or cupped surfaces may be formed in a portion of the base surface 108, as well as in portions of the surfaces 107, 106 and 100-104, typically located substantially centrally and directly below an arm 62. Such a cupped surface may be sized and shaped for providing clearance for an increased angle of articulation between the shank 4 and the receiver 10 (see, e.g., FIGS. 51-56).

With particular reference to FIGS. 1 and 11-16, the lower open or split friction fit retainer 12, that operates to capture the shank upper portion 8 within the receiver 10 is shown. In certain stages of assembly and operation, the retainer 12 is partially constrained within the receiver, being captured within the receiver cavity 61 at a location below the surface 96, the retainer 12 being rotatable with respect to the receiver, but not pivotable thereto and not readily removable out of the receiver once deployed downward into the receiver cavity 61. The retainer 12 has a central axis that is operationally the same as the axis B associated with the receiver 10 when the shank upper portion 8 and the retainer 12 are installed within the receiver 10. The retainer 12 includes a substantially annular, cylindrical discontinuous body 115. Extending upwardly and outwardly from the body 115, and integral thereto, are two sets of flexible panels or tangs, in particular, inner panels or tangs 117 and outer panels or tangs 118, the panels 117 and 118 extending upwardly in aligned pairs, allowing for lateral spaces between the pairs panels or tangs to provide clearance during assembly of the retainer 12 with the receiver 10 inner surfaces (see, e.g., FIGS. 25 and 26). The illustrated embodiment includes six pairs of inner and outer panels or tangs 117, 118, but it is foreseen that more or fewer panels or tangs may be used. The pairs of panels or tangs are generally equally spaced about the body 115. Also integral to the body 115 are six outer discontinuous cylindrical support surfaces 120, each surface 120 located beneath one of the outer panels 118 and extending radially outwardly from the body 115. Below the surfaces 120, the cylindrical body 115 forms a lower outer cylindrical skirt 121 broken only by a gap that will be described in greater detail below. The outer surface 121 is adjacent a bottom surface 122. The body 115 also includes outer surface portions 123 that are located between each outer panels 118 and support surfaces 120. The surface portions 123 are illustrated as substantially planar, but may be cylindrical. At each of the panels 118, a lower ledge surface 124 is adjacent to one of the outer support surfaces 120. Each lower ledge 124 spans between one of the surfaces 120 and the cylindrical skirt surface 121. The lower skirt 121 and the ledge surfaces 124, as well as the surfaces 120 are receiver seating surfaces as will be described in greater detail below. In the illustrated embodiment, transition areas where the body 115 meets the panels 117 and 118 or the retainer bottom 122 are curved or chamfered. Each body portion 123 is adjacent to a substantially planar body top surface 126 that is substantially located between pairs of panels 117 and 118 forming a planar surface with a trapezoidal profile and also includes a narrow strip that runs between the inner panels 117 and the outer panels 118.

The inner panels or tangs 117 each include a substantially planar outer surface 128 and a concave inner surface 129, the surfaces 129 each being partially radiused and partially cylindrical, making up a discontinuous curved surface sized and shaped for friction fit engagement with the shank head 8 as best shown in FIG. 37 and as will be described in greater detail below. The panels 117 generally slant or curve inwardly towards the central axis of the retainer 12 and thus ultimately inwardly toward the shank head 8. Each panel 117 includes a top surface 130 that is substantially planar and runs substantially parallel to the bottom surface 122 when the retainer is in a neutral position such as that shown in FIG. 16.

The outer panels or tangs 118 each have a planar outer surface 132, a planar inner surface 133 and a planar top surface 134 that slopes at an oblique angle with respect to the retainer bottom surface 122. The surfaces 134 are perpendicular to adjacent surfaces 132. The panels 118 generally extend outwardly away from the panels 117 as well as outwardly and upwardly from the central axis of the retainer body 115. Each surface 133 faces an outer surface 128 of one of the panels 117. The body top surface 126 is reduced to a narrow strip between each pair of panels 117 and 118. The panels or tangs 117 and 118 are resilient, the panels being expandable about the shank head 8 and the panels 118 being compressible inwardly and resiliently holding against the receiver inner surfaces during shipping and certain assembly steps. The panels 118 then return to an original or near original shape within the receiver cavity 61, capturing the retainer 12 within the receiver 10, but still allowing for rotation of the retainer 12 with respect to the receiver 10 about the receiver central axis B.

The retainer ring 12 is made from a resilient material, such as a stainless steel or titanium alloy, so that the retainer 12 body 115 may be expanded and the tabs or panels 117 and 118 of the retainer may be manipulated during various steps of assembly as will be described in greater detail below. The retainer 12 has a central channel or hollow through bore, generally 141, that passes entirely through the retainer 12 from the inner panel top surfaces 130 to the bottom surface 122 of the retainer body 115. Surfaces that define the channel or bore 141 at the body 115 include a discontinuous inner lower frusto-conical surface 143 adjacent to the retainer body bottom surface 122, a discontinuous, substantially cylindrical surface 145 adjacent the frusto-conical surface 143 and a discontinuous annular step 146 located adjacent the cylindrical surface 145, the surface 146 being substantially parallel to the bottom surface 122 and extending between the surface 145 and a lower cylindrical portion 129' of the inner surface 129 that partially forms the inner panels 117. The surfaces 145 and 146 terminate and join together at an edge 147 that is positioned and configured to engage the shank surface 34 as will be described in greater detail below. The inner cylindrical surface 129' adjacent the step 146 forms a continuous inner cylindrical wall except at a slit, generally 148 that runs through the body 115. The slit 148 creates a split or open ring retainer 12, the slit cutting entirely through the retainer body 115. In some embodiments, such a slit may run at an angle obtuse to the bottom surface 122. In the illustrated embodiment, the slit 148 runs substantially perpendicular to the surfaces 122. The slit 148 is primarily for expansion of the retainer 12 during pop-on or snap-on assembly with the shank head 8. However, the slit 148 also compresses during assembly with the receiver 10 as will be described in greater detail below. The slit 148 extends between the body top surface 126 and the bottom surface 122 and is located substantially centrally between two pairs of tangs or panels 117 and 118. Furthermore, at the location of the slit 148, a curved concave, cut-out surface 149 is formed in the bottom surface 122 and the frusto-conical surface 143. The cut-out surface 149 also extends into the cylindrical surface 145 and removes a portion of the step 146 at either side of the slit 148. The surface 149 is radiused or otherwise curved for engagement with the shank head 8 at the surface 34 as will be described in greater detail below. In the illustrated embodiment, the cut-out surface 149 is located substantially equally on either side of the slit 148 to provide for a desirable increased angle of orientation between the shank 8 and the retainer 12 and thus a desirable increased angle of articulation between the shank 8 and the receiver 10. The rotatability of the semi-constrained retainer 12 with respect to the receiver 10 allows for manipulation and placement of such an increased angle of articulation to a location desired by a surgeon. The through slit 148 of the resilient retainer 12 is defined by first and second end surfaces, 152 and 153 disposed in substantially parallel spaced relation to one another when the retainer is in a neutral or nominal state. Both end surfaces 152 and 153 are disposed perpendicular to the bottom surface 122, but in some embodiments may be disposed at an obtuse angle thereto. A width between the surfaces 152 and 153 is narrow to provide stability to the retainer 12 during operation, but wide enough to allow for some compression of the retainer during assembly as will be described in greater detail below. Because the retainer 12 is top loadable in a substantially neutral state and ultimately expands during locking of the polyaxial mechanism, the width of the slit 148 may be much smaller than might be required for a bottom loaded compressible retainer ring.

With particular reference to FIGS. 1 and 17-24, the locking compression insert 14 is illustrated that is sized and shaped to be received by and down-loaded into the receiver 10 at the upper opening 66. The compression insert 14 has an operational central axis that is the same as the central axis B of the receiver 10. In operation, the insert advantageously frictionally engages the bone screw shank upper portion 8 as well as engaging the receiver 10 in an interference fit engagement, locking the shank 4 in a desired angular position with respect to the receiver 10 that remains in such locked position even if, for example, a rod and closure top are later removed and the rod is replaced with another rod or other longitudinal connecting member or member component, such as a sleeve of a tensioned cord connecting member. Such locked position may also be released by the surgeon if desired with insert engaging tools (not shown). In some embodiments of the invention, the insert does not have the receiver interference fit feature, but otherwise performs like insert 14. In such embodiments, tooling may be used to hold the insert in temporary locking engagement with the shank, if desired. Both locking and non-locking inserts, as well as an alternative locking insert 14' for use with a deformable rod (shown in FIGS. 40 and 41) are preferably made from a solid resilient material, such as a stainless steel or titanium alloy, so that portions of the insert may be grasped, pinched or pressed, if necessary, and un-wedged from the receiver 10 with a release tool (not shown), if desired.

The locking compression insert 14 includes a body 156 with cylindrical surfaces of a variety of diameters, the body 156 being integral with a pair of upstanding arms 157. Located between the arms 157, the body 156 has an outer partial cylindrical surface 158. Located beneath each upstanding arm 157 is a discontinuous, cylindrical, interference fit surface or band 159 that extends outwardly from an arm and body outer substantially cylindrical surface 160, a diameter of the surface 159 being larger than a diameter of the surface 160. Beneath each surface 159 is a discontinuous cylindrical surface 161 having a diameter slightly smaller than the diameter of the surface 159 and the same or larger than the diameter of the surface 160. In the illustrated embodiment, the diameter of the surface 161 is greater than the diameter of the surface 160. A lower ledge surface 162 spans between each surface 159 and the corresponding lower cylindrical surface 161. The lower surface 161 is adjacent to a chamfered surface 163 that is in turn adjacent a substantially planar and annular surface or ledge 164A. Each lower annular surface or ledge 164A is in or approximately in a same plane as an annular bottom surface 164B of the located beneath the cylindrical body surface 158. Each arm 157 further includes a substantially top surface 165 and located opposite each top arm surface is a bottom surface 166 of a discontinuous frusto-conical substructure, generally 167 that has an outer surface 167A and an inner surface 167B. The outer surface 167A runs inwardly toward a central axis of the insert 14 from the ledge 164A to the bottom surface 166 and the inner surface 167B runs outwardly away from the insert central axis from the body bottom surface 164B outwardly to the substructure bottom surface 166. During final locking of the bone screw 1, the substructure inner surfaces 167B press downwardly and inwardly on the retainer inner tangs 117, pushing the tangs 117 into engagement with the shank head surface 34. Because the retainer 12 expands outwardly toward the receiver 10 during final locking, the inner tangs 117, that provide temporary friction fit during angular manipulation of the shank 8 with respect to the receiver 10, tend to move away from the shank head surface 34 during final locking. However, the downwardly pressing insert substructure 167 advantageously prohibits the tangs 117 from such outward movement and thus press or crush the resilient tangs 117 toward the shank head 8 and into final hard lock, prohibiting any further pivoting or other movement of the shank 4 with respect to the receiver 10.

The insert 14 The arms 157 are sized and configured for ultimate placement at or beneath the cylindrical run-out surface 90 located below the receiver guide and advancement structure 72. Inner grooves or apertures 179 located below arm top surfaces 165 provide holding surfaces for tools and also provide some clearance between the closure top 18 and the insert 14 when both are within the cylindrical run-out surface 90 of the receiver so that the closure top 18 frictionally engages the rod 21 only, pressing the rod 21 downwardly against the insert 14 that in turn presses against the shank 4 upper portion 8 that presses against the retainer 12 to lock the polyaxial mechanism of the bone screw assembly 1 at a desired angle. Additionally, the grooves 179 may be sized and shaped to cooperate with protrusions or extensions on sleeves that cooperate with a tensioned cord of a longitudinal connecting member assembly to center such a sleeve within the bone screw assembly 1.

An alternative locking insert 14' shown in FIGS. 40 and 41 includes all the features of the insert 14 with the exception of the grooves 179. Top surfaces 165' of the insert 14' that have more surface area than the surfaces 165 of the insert 14 directly engage the alternative closure top 18' for better locking of the polyaxial mechanism when an alternative deformable rod 21' is being captured between the insert 14' and the closure top 18'.

Returning to the insert 14 shown in FIGS. 17-24, located on the arms 157 and extending outwardly from each surface 160 at a location spaced from the top surfaces 165 are a pair of opposed extensions or wings 168. The wings 168 are partially defined by upper surfaces 169, by outer partially cylindrical surfaces 170 and by lower surfaces 171, the upper surfaces 169 and the lower surfaces 171 being substantially parallel to on another. Opposed, grooved or inset side surfaces 172 are located between top and bottom surfaces 169 and 171 respectively, of each wing 168, the side surfaces 172 being substantially perpendicular to adjacent top and bottom surfaces 169 and 171. The cylindrical surfaces 170 are sized and shaped for sliding rotation within the receiver arm cylindrical surfaces 92 during assembly of the insert 14 with the receiver 10 as will be described in greater detail below.

Returning to the inner surfaces of the insert 14, a through bore, generally 173, is disposed primarily within and through the body 156 and communicates with a generally U-shaped through channel formed by a saddle surface 174 that is substantially defined by the upstanding arms 157. Near the top surfaces 165, the saddle surface 174 is substantially planar, with the apertures 179 extending thereinto.

The saddle 174 has a lower seat 175 sized and shaped to closely, snugly engage the rod 21 or other longitudinal connecting member. It is foreseen that an alternative embodiment may be configured to include planar holding surfaces that closely hold a square or rectangular bar as well as hold a cylindrical rod-shaped, cord, or sleeved tensioned cord longitudinal connecting member. A second set of opposed, inwardly facing apertures 176 are located in the saddle 174 near the lower seat 175 and substantially directly below, but spaced from, the upper grooves or apertures 179. The grooves 176 are sized and shaped to receive tooling for rotation and other types of manipulation of the insert 14.

The bore, generally 173, is substantially defined at the body 156 by an inner cylindrical surface 177 that communicates with the seat 175 and also communicates with a lower concave, radiused or otherwise curved portion 178 having shank gripping surfaces or ridges 180, the portion 178 generally having a radius for closely mating with the surface 34 of the shank upper portion 8. The portion 178 terminates at the body base surface 164B. In some embodiments of the invention, the gripping surfaces or ridges 180 are located near the cylindrical surface 177 and a lower part of the portion 178 is a smooth, radiused or spherical surface. In the illustrated embodiment, the gripping ridges or steps 180 are sized and shaped to grip and penetrate into the shank head 8 when the insert 14 is locked against the head surface 34. It is foreseen that there may be more or fewer steps or ridges 180. It is foreseen that the gripping ridges 180 as well as a remainder of the lower shank engaging portion 178 may additionally or alternatively include a roughened or textured surface or surface finish, or may be scored, knurled, or the like, for enhancing frictional engagement with the shank upper portion 8.

The compression insert 14 through bore 173 is sized and shaped to receive a driving tool (not shown) therethrough that engages the shank drive feature 46 when the shank body 6 is driven into bone with the receiver 10 attached. Also, in some locking embodiments of the invention, the bore receives a manipulation tool (not shown) used for releasing the insert from a locked position with the receiver, the tool pressing down on the shank and also gripping the insert at the apertures 176 and/or 179, or with other tool engaging features. Each of the arms 157 and the insert body 156 may include more surface features, such as cut-outs notches, bevels, etc. to provide adequate clearance for inserting the insert 14 into the receiver and cooperating with the retainer 12 during the different assembly steps as will be described in greater detail below.

The insert body 156 cylindrical surface 158 has a diameter slightly smaller than a diameter between crests of the guide and advancement structure 72 of the receiver 10, allowing for top loading of the compression insert 14 into the receiver opening 66, with the arms 157 of the insert 14 being located between the receiver arms 62 during insertion of the insert 14 into the receiver 10. Once the arms 157 of the insert 14 are generally located beneath the guide and advancement structure 72, the insert 14 is rotated into place about the receiver axis B with the wings 168 entering the receiver groove formed by the cylindrical surface 92, the adjacent upper annular surface 91 and the adjacent lower annular surface 93 until the wings are located in the apertures 77 as will be described in greater detail below.

With reference to FIGS. 1 and 37-39, the illustrated elongate rod or longitudinal connecting member 21 (of which only a portion has been shown) can be any of a variety of implants utilized in reconstructive spinal surgery, but is typically a cylindrical, elongate structure having the outer substantially smooth, cylindrical surface 22 of uniform diameter. The rod 21 may be made from a variety of metals, metal alloys, non-metals and deformable and less compressible plastics, including, but not limited to rods made of elastomeric, polyetheretherketone (PEEK) and other types of materials, such as polycarbonate urethanes (PCU) and polyethelenes.

Longitudinal connecting members for use with the assembly 1 may take a variety of shapes, including but not limited to rods or bars of oval, rectangular or other curved or polygonal cross-section. The shape of the insert 14 may be modified so as to closely hold the particular longitudinal connecting member used in the assembly 1. Some embodiments of the assembly 1 may also be used with a tensioned cord. Such a cord may be made from a variety of materials, including polyester or other plastic fibers, strands or threads, such as polyethylene-terephthalate. Furthermore, the longitudinal connector may be a component of a longer overall dynamic stabilization connecting member, with cylindrical or bar-shaped portions sized and shaped for being received by the compression insert 14 of the receiver having a U-shaped, rectangular- or other-shaped channel, for closely receiving the longitudinal connecting member. The longitudinal connecting member may receive a cord and/or be integral or otherwise fixed or connected to a bendable or damping component that is sized and shaped to be located between adjacent pairs of bone screw assemblies 1, for example. A damping component or bumper may be attached to the longitudinal connecting member at one or both sides of the bone screw assembly 1. A rod or bar (or rod or bar component) of a longitudinal connecting member may be made of a variety of materials ranging from deformable plastics to hard metals, depending upon the desired application. Thus, bars and rods used in embodiments of the invention may be made of materials including, but not limited to metal and metal alloys including but not limited to stainless steel, titanium, titanium alloys and cobalt chrome; or other suitable materials, including plastic polymers such as polyetheretherketone (PEEK), ultra-high-molecular weight-polyethylene (UHMWP), polyurethanes and composites, including composites containing carbon fiber, natural or synthetic elastomers such as polyisoprene (natural rubber), and synthetic polymers, copolymers, and thermoplastic elastomers, for example, polyurethane elastomers such as polycarbonate-urethane elastomers.

With reference to FIGS. 1 and 37-39, the closure structure or closure top 18 shown with the assembly 1 is rotatably received between the spaced arms 62 of the receiver 10. It is noted that the closure 18 top could be a twist-in or slide-in closure structure. The illustrated closure structure 18 is substantially cylindrical and includes a an outer helically wound guide and advancement structure 182 in the form of a flange that operably joins with the guide and advancement structure 72 disposed on the arms 62 of the receiver 10. The flange form may take a variety of forms, including those described in Applicant's U.S. Pat. No. 6,726,689, which is incorporated herein by reference. Although it is foreseen that the closure structure guide and advancement structure could alternatively be a buttress thread, a square thread, a reverse angle thread or other thread like or non-thread like helically wound advancement structure, for operably guiding under rotation and advancing the closure structure 18 downward between the arms 62 and having such a nature as to resist splaying of the arms 62 when the closure structure 18 is advanced into the channel 64, the flange form illustrated herein as described more fully in Applicant's U.S. Pat. No. 6,726,689 is preferred as the added strength provided by such flange form beneficially cooperates with and counters any reduction in strength caused by the any reduced profile of the receiver 10 that may more advantageously engage longitudinal connecting member components. The illustrated closure structure 18 also includes a top surface 194 with an internal drive 196 in the form of an aperture that is illustrated as a star-shaped internal drive such as that sold under the trademark TORX, or may be, for example, a hex-shaped drive or other internal drives such as slotted, tri-wing, spanner, two or more apertures of various shapes, and the like. A driving tool (not shown) sized and shaped for engagement with the internal drive 196 is used for both rotatable engagement and, if needed, disengagement of the closure 18 from the receiver arms 62. It is also foreseen that the closure structure 18 may alternatively include a break-off head designed to allow such a head to break from a base of the closure at a preselected torque, for example, 70 to 140 inch pounds. Such a closure structure would also include a base having an internal drive to be used for closure removal. A base or bottom surface 198 of the closure is planar and further includes a rim 200 for engagement and penetration into the surface 22 of the rod 21 in certain embodiments of the invention. It is noted that in some embodiments, the closure top bottom surface 198 may further include a central point for penetration into the rod. It is also noted that other embodiments may or may not include the point and/or the rim. The closure top 18 may further include a cannulation through bore (not shown) extending along a central axis thereof and through the top and bottom surfaces thereof. Such a through bore provides a passage through the closure 18 interior for a length of wire (not shown) inserted therein to provide a guide for insertion of the closure top into the receiver arms 62.

An alternative closure top, such as the top 18' shown in FIGS. 40 and 41 for use with a deformable rod, such as a PEEK rod 21', for example, includes a bottom surface 198' that has domed portion 200' with a central nub 199' in lieu of the point and rim surface of the closure top 18. Otherwise, the closure top 18' includes a guide and advancement structure 192', a top surface 194' and an internal drive feature 196' the same or substantially similar to the respective guide and advancement structure 192, top surface 194 and internal drive feature 196 of the closure top 18.

The assembly 1 receiver 10, retainer 12 and compression insert 14 are typically assembled at a factory setting that includes tooling for holding and alignment of the component pieces and manipulating the retainer 12 and the insert 14 with respect to the receiver 10. In some circumstances, the shank 4 is also assembled with the receiver 10, the retainer 12 and the compression insert 14 at the factory. In other instances, it is desirable to first implant the shank 4, followed by addition of the pre-assembled receiver, retainer and compression insert at the insertion point. In this way, the surgeon may advantageously and more easily implant and manipulate the shanks 4, distract or compress the vertebrae with the shanks and work around the shank upper portions or heads without the cooperating receivers being in the way. In other instances, it is desirable for the surgical staff to pre-assemble a shank of a desired size and/or variety (e.g., surface treatment of roughening the upper portion 8 and/or hydroxyapatite on the shank 6), with the receiver, retainer and compression insert. Allowing the surgeon to choose the appropriately sized or treated shank 4 advantageously reduces inventory requirements, thus reducing overall cost and improving logistics and distribution.

Figure 28:
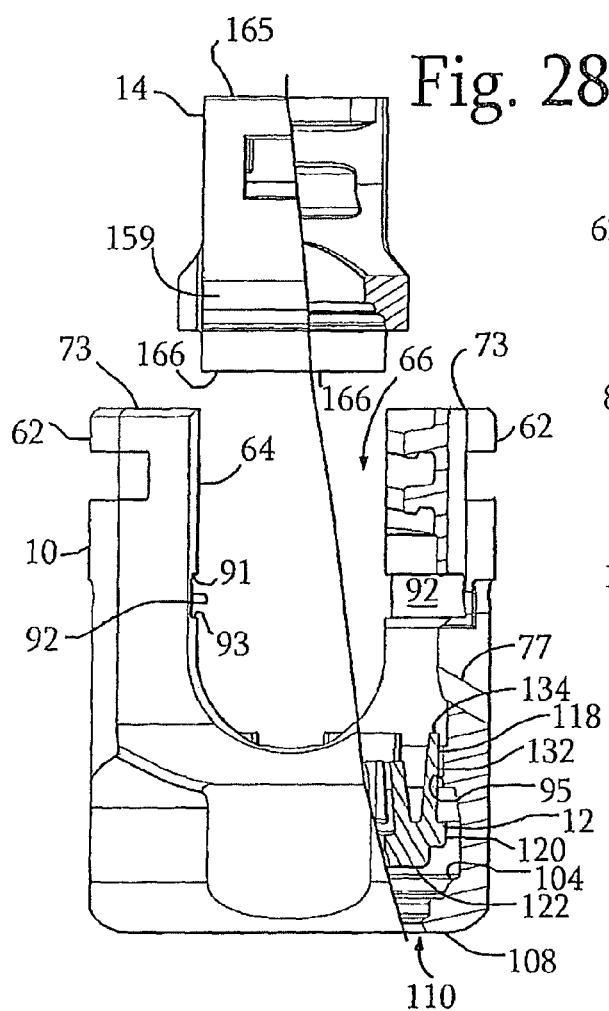
FIG. 28 is an enlarged front elevational view of the retainer and receiver with portions broken away, similar to what is shown in FIG. 26, showing the retainer positioned lower in the receiver cavity and further shows the insert in position for assembly with the receiver.

Pre-assembly of the receiver 10, retainer 12 and compression insert 14 is shown in FIGS. 25-32. With particular reference to FIG. 25, first the retainer 12 is inserted into the upper receiver opening 66, leading with the outer panels 118 with the panel 118 top surfaces 134 facing one arm 62 and the retainer bottom surface 122 facing the opposing arm 62 (shown in phantom). The retainer 12 is then lowered in such sideways manner into the channel 64 and partially into the receiver cavity 61, followed by tilting the retainer 12 such that at least one outer panel 118 is received into one of the apertures 77 and the opposed panel 118 is located beneath the guide and advancement structure 72. Then, with reference to FIG. 26, the retainer 12 is tilted into a position wherein the central axis of the retainer 12 is generally aligned with the receiver central axis B. As shown in FIG. 26, the retainer outer surfaces 120 engage the receiver inner cylindrical surface 95 and the retainer slit 148 is reduced such that the surfaces 152 and 153 that define the slit 148 are touching or almost touching as shown in FIG. 27 while the surfaces 120 are slid past the receiver surface 95. With reference to FIG. 28, the retainer 12 is pressed downwardly into the receiver to a location wherein the outer tangs 118 resiliently press against the receiver surface 95, holding the retainer within the receiver cavity 61 at a desired temporary position, but not allowing the retainer 12 to drop downwardly onto the receiver seating transition surfaces 104. At this time, the retainer 12 is not yet fully captured within the receiver base cavity 61, but cannot be readily removed unless the tangs 118 are squeezed toward one another using a tool or tools.

Figure 29:
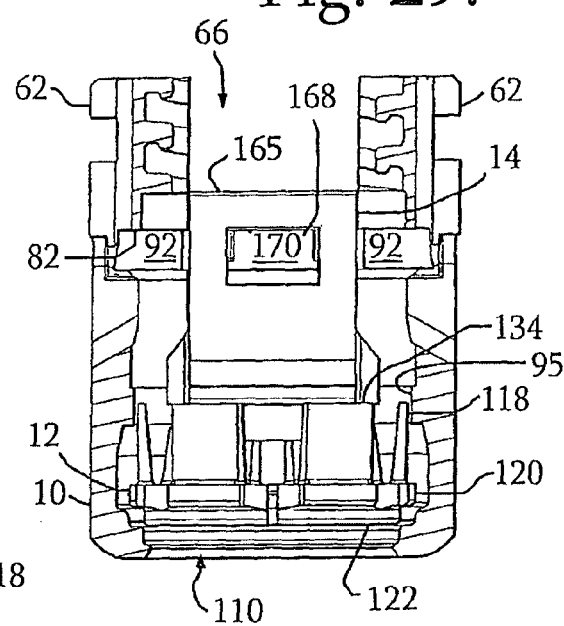
FIG. 29 is a reduced front elevational view of the retainer, receiver and insert with portions broken away, similar to what is shown in FIG. 28, further showing the insert downloaded into the receiver to a location suitable for rotation within the receiver.
Figure 30:
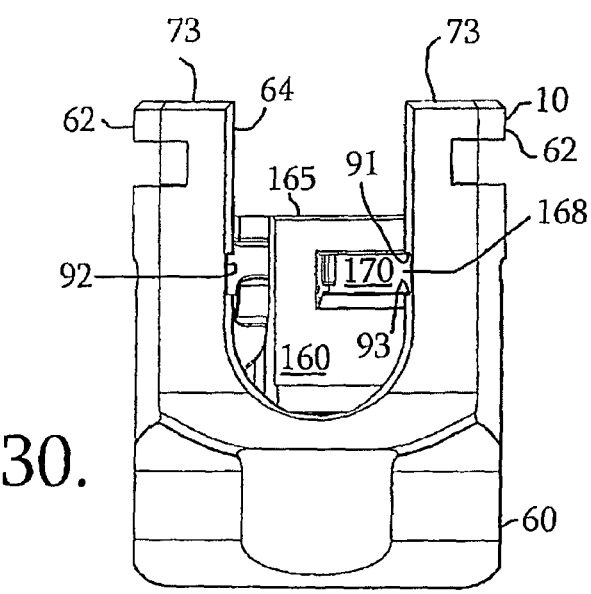
FIG. 30 is a front elevational view of the retainer, receiver and insert, similar to what is shown in FIG. 29, further showing the insert being partially rotated within the receiver.
Figure 32:
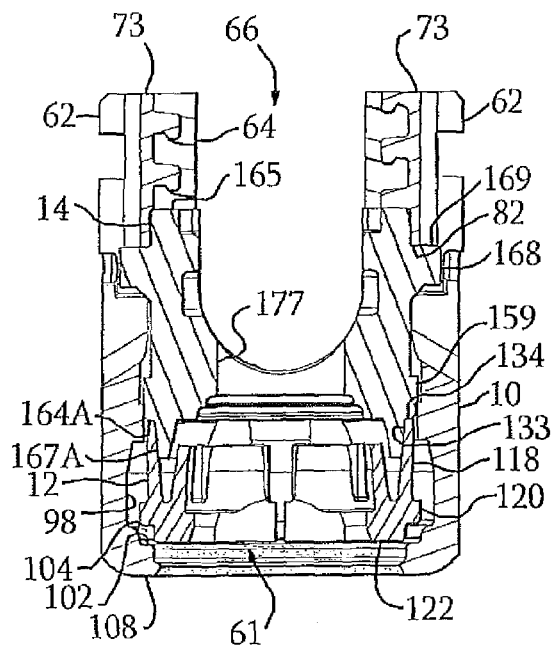
FIG. 32 is a front elevational view with portions broken away of the assembly of FIG. 31.

With further reference to FIG. 28 and with reference to FIGS. 29 and 30, the compression insert 14 is then downloaded into the receiver 10 through the upper opening 66 with the substructure bottom surfaces 166 facing the receiver arm top surfaces 73 and the insert arm outer surfaces 160 and the substructures 167 located between the opposed receiver arms 62. The insert 14 is then lowered toward the receiver base 60 until the insert 14 arm upper surfaces 165 are adjacent the run-out area below the guide and advancement structure 72 defined in part by the cylindrical surface 90 and the wings 168 are generally aligned with the receiver groove defined in part by the cylindrical surface 92. Thereafter, the insert 14 is rotated about the receiver axis B until the upper arm surfaces 165 are directly below the guide and advancement structure 72 with the U-shaped channel 173 of the insert 14 aligned with the U-shaped channel 64 of the receiver 10 and the insert wings 168 located at the apertures 77 as best shown in FIGS. 31 and 32. In some embodiments, the insert arms may need to be compressed slightly during rotation to clear some of the inner surfaces 70 of the receiver arms 62. With particular reference to FIG. 31, at this time, the four receiver crimping wall portions 84 are pressed inwardly towards the insert 14 at either side groove 172 of each wing 168, the crimping wall material pressing against the insert 14 near the wing surfaces 172 and thereby prohibiting the insert 14 from rotating with respect to the receiver axis B. At this time, there can be some upward and downward movement of the insert 14, but such movement is limited as the upper wall 82 defining the receiver aperture 77 stops further upward movement of the insert wings 168 and the retainer outer tang top surfaces 134 stop downward movement of the now trapped insert 14 at the outer ledge surfaces 164A with the insert substructure outer surfaces 167A in sliding engagement with the tang 118 inner surfaces 133. Thus, the frictional engagement between the tangs or panels 118 and the receiver inner surfaces 95 prohibit the retainer 12 and also the insert 14 from dropping further down into the receiver 10 cavity 61.

The retainer 12 and the insert 14 are now in a desired position for shipping as an assembly along with the separate shank 4.

Typically, the receiver and retainer combination are shipped or otherwise provided to the end user with the spring-like tangs 118 wedged against the receiver as shown in FIG. 32. The receiver 10, retainer 12 and insert 14 combination is now pre-assembled and ready for assembly with the shank 4 either at the factory, by surgery staff prior to implantation, or directly upon an implanted shank 4 as will be described herein.

Figure 33:
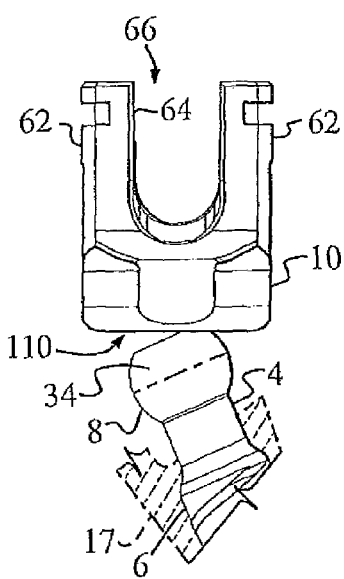
FIG. 33 is a reduced front elevational view of the assembly of FIG. 32, the figure further showing the shank of FIG. 1 in a partial front elevational view and implanted into a portion of a vertebra, a hemisphere of the shank head and the vertebra portion are both shown in phantom.

As illustrated in FIG. 33, the bone screw shank 4 or an entire assembly 1 made up of the assembled shank 4, receiver 10, retainer 12 and compression insert 14, is screwed into a bone, such as the vertebra 17 (shown in phantom), by rotation of the shank 4 using a suitable driving tool (not shown) that operably drives and rotates the shank body 6 by engagement thereof at the internal drive 46. Specifically, the vertebra 17 may be pre-drilled to minimize stressing the bone and have a guide wire (not shown) inserted therein to provide a guide for the placement and angle of the shank 4 with respect to the vertebra. A further tap hole may be made using a tap with the guide wire as a guide. Then, the bone screw shank 4 or the entire assembly 1 is threaded onto the guide wire utilizing the cannulation bore 50 by first threading the wire into the opening at the bottom 28 and then out of the top opening at the drive feature 46. The shank 4 is then driven into the vertebra using the wire as a placement guide. It is foreseen that the shank and other bone screw assembly parts, the rod 21 (also having a central lumen in some embodiments) and the closure top 18 (also with a central bore) can be inserted in a percutaneous or minimally invasive surgical manner, utilizing guide wires and attachable tower tools mating with the receiver. When the shank 4 is driven into the vertebra 17 without the remainder of the assembly 1, the shank 4 may either be driven to a desired final location or may be driven to a location slightly above or proud to provide for ease in assembly with the pre-assembled receiver, compression insert and retainer.

Figure 34:
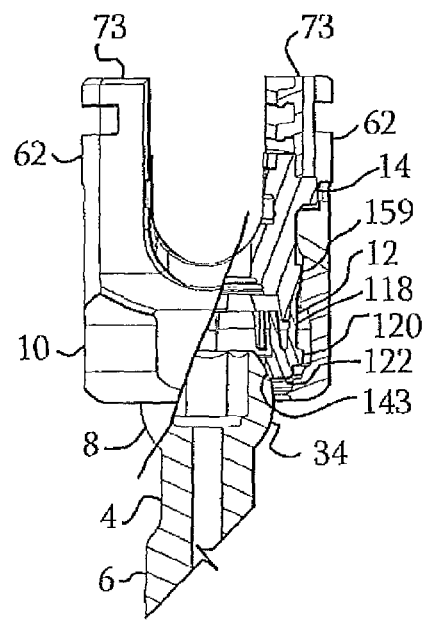
FIG. 34 is an enlarged and partial front elevational view with portions broken away, similar to FIG. 33, and further showing the shank in a first stage of assembly with the receiver and retainer.
Figure 35:
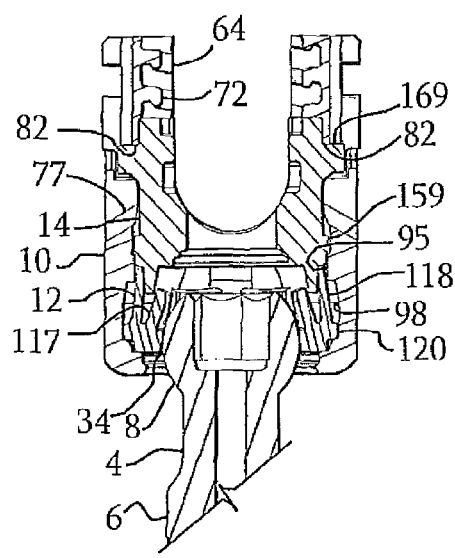
FIG. 35 is a partial front elevational view with portions broken away, similar to FIG. 34, showing the retainer lower portion in an expanded state about a mid-portion of the shank head.

With reference to FIGS. 33 and 34, the pre-assembled receiver, insert and retainer are placed above the shank upper portion 8 until the shank upper portion is received within the opening 110. With particular reference to FIG. 35, as the shank upper portion 8 is moved into the interior 61 of the receiver base, the shank upper portion 8 presses upwardly against the retainer 12 in the receiver recess partially defined by the cylindrical surface 98, specifically the surface portions 120 press against the surface 98 as the retainer 12 expands about the shank 8. As the shank head 8 continues to move upwardly toward the channel 64, the shank head surface 34 also forces the retainer 12 against the insert 14. However, the insert 14 is prohibited from moving upward by the wing upper surfaces 169 abutting against the surfaces 82 (that is also the ceiling annular surface 91 adjacent the groove 92) defining the apertures 77. Therefore, the upwardly moving shank head 8 forces a widening of the retainer slit 148 and corresponding outward movement of the body 115 of the retainer 12 towards the receiver cylindrical surfaces 98 and stepped or curved surface 104 defining the receiver expansion recess or chamber while the retainer tangs 118 near the top surfaces 134 thereof are generally maintained in a location below the insert 14 lower ledge surfaces 164A, with the tangs 118 being pressed inwardly toward the axis B at the termination of the receiver wall surface 95. At this time, the spherical surface 34 of the head 8 comes into contact with the retainer inner cylindrical body 145 and the edge 147.

Figure 36:
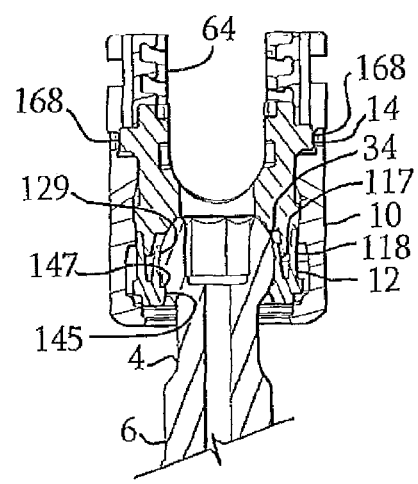
FIG. 36 is a reduced and partial front elevational view with portions broken away, similar to FIG. 35, the spherical shank upper portion or head shown fully captured by the retainer.

With reference to FIG. 36, the retainer 12 begins to return towards a neutral or nominal state as the center of the sphere of the shank head 8 passes beyond the retainer inner edge 147. By the time the hemisphere of the spherical surface 34 extends into a desired captured location within the retainer central bore 141, the shank surface 34 is in contact with the edge 147 as well as with the inner panels 117 at surfaces 129. The combination of the rim or edge 147 surface contact and the panel 117 surfaces 129 contact resiliently pressing against the radiused surface 34, provides a fairly tight friction fit between the head 8 and the retainer 12, the surface 34 being pivotable with respect to the retainer 12 with some force. Thus, a tight, non-floppy ball and socket joint is now created between the retainer 12 and the shank upper portion 8.

With reference to FIG. 37, the receiver is then pulled upwardly or the shank 4 and attached retainer 12 are then moved manually downwardly into a position wherein the retainer tangs 118 are disengaged from the receiver surfaces 95, allowing the tangs 118 to resiliently release and extend outwardly into a neutral or near-neutral position at a location below the receiver annular surface 96 that defines the ceiling of the receiver inner chamber 61. The tangs 118 are now captured within the receiver. Any upward movement of the retainer 12 results in the tang top surfaces 134 abutting against the receiver surfaces 96 and/or 97. However, although fully captured, the retainer 12/shank 4 combination is advantageously only partially restrained with respect to the receiver 10, as a user is able to rotate the retainer 12 about the receiver axis B prior to final locking of the shank head 8 with respect to the receiver 10. At this time also, the retainer surface 121 and bottom surface 122 that forms a lower skirt beneath the retainer body surfaces 120 and 124 are all seated within the stepped surfaces of the receiver. Specifically, the retainer lower surfaces 124 are seated on the receiver annular surface 102 and the bottom surface 122 is seated on the annular surface 103. Downward pressure of the shank head 8 on the retainer edge 147 further expands the retainer body 115 outwardly, with the outer surfaces 120 pressing against the receiver inner cylindrical surface 100 and the lower skirt surface 121 pressing against the receiver inner cylindrical surface 101. The retainer body formed in part by the lower skirt surface 121 advantageously allows for the head 8 to seat lower within the receiver than in other known polyaxial bone anchors. As will be described in greater detail below, the skirt feature that allows for a more stable lower seating surface in combination with the retainer cupped surface 149 that allows for increased angular orientation of the shank with respect to the retainer, and thus with respect to the entire bone screw assembly, allows for such an angular increase without the need to provide a cut-out or cupped surface at and near the receiver bottom 108. Also advantageous is the fact that the partially constrained retainer 12 may be rotated with respect to the receiver 10 about the axis B, allowing for the user to choose the location of the increased angle of orientation between the receiver 10 and the shank 4.

With further reference to FIG. 37, after the retainer 12 is moved downwardly into the receiver 10 and seated on the surfaces 102 and 103, the insert 14 remains located spaced above the shank head 8 as the outer surfaces 159 rest upon the receiver cylindrical surfaces 95, prohibiting downward movement of the insert 14 unless a downward force is applied on the insert either by a tool or the rod 21 and closure top 18, also shown in FIG. 37, for example. It is noted that FIG. 38 simply illustrates the extent of movement of the shank 4 if the shank is pressed upwardly into the receiver during this stage of assembly. In such case, the retainer 12 would remain in a relatively fixed position due to the outer tangs 118 being blocked from upward movement by the receiver ceiling surface 96. The shank head 8 would abut against the insert 14 at the surface 178 and gripping ridges 180, but the inner tangs 117 would continue to grip the shank spherical surface 34, so a friction fit would still be possible, even if the shank gets moved upwardly. With reference to FIG. 39, downward movement of the closure top 18 presses the rod 21 downwardly that in turn presses the insert 14 and the shank head 8 downwardly into locking engagement with the retainer 12. When the insert 14 is pressed downwardly toward the retainer 12 by downward movement of the rod and closure top 18, the insert sub-structure 167, specifically the surface 167B comes into contact with some of the tangs 117 that are otherwise moving outwardly away from the shank surface 34 as the retainer body is being pressed radially outwardly by the lower portion of the shank head 8. The sloping surface 167B presses radially inwardly on the outer surfaces 128 of some of the tangs 117. Thus, the insert 14 sub-structure prohibits outward movement of the tangs 117, compressing them into frictional locking engagement with the shank head 8 once the closure top 18 is in full mating engagement with the receiver 10.

In some embodiments, when the receiver 10 is pre-assembled with the shank 4, the entire assembly 1 may be implanted by inserting the driving tool (not shown) into the receiver and the shank drive 46 and rotating and driving the shank 4 into a desired location of the vertebra 17. At such time, prior to locking with a closure top, the receiver 10 may be articulated to a desired angular position with respect to the shank 4 (such as the angular orientations shown in FIGS. 42-47, for example), that will be held, but not locked, by the frictional engagement between the retainer 12 inner tangs 117 and the shank upper portion 8. In some cases it may be desirable to lock the insert 14 into the receiver 10 at this time, the insert 14 being pressed downwardly into locking engagement with the shank head 8 by a tool pressing downwardly on the insert, for example, with a tool (not shown) entering through the receiver outer grooves 74 and pressing downwardly on the tops 169 of the insert wings 168. Such a tool may also include (or alternatively be) a structure for gripping the receiver, for example, a pronged tool or tool portion with some of the tool extending into the receiver channel 64. Or, as explained above, the insert 14 may remain spaced above the shank head 8 until locked into place by the rod 21 and the closure top 18 pressing down upon the insert 14.

As explained above and as best shown in FIGS. 37 and 39, the diameter of the insert outer surface or band 159 is sized large enough to require that the surface 159 must be forced into the cylindrical surface 95 of the receiver by a tool or tools or by the closure top 18 forcing the rod 21 downwardly against the insert 14 with sufficient force to interferingly frictionally lock or wedge the insert 14 into the receiver 10 at the surface 159. This independent lock-and-release feature gives the surgeon flexibility to loosen the closure top and even remove the closure top and rod without affecting the locking of the polyaxial mechanism of the assembly 1, the anchor assembly functioning like a fixed monoaxial screw with the shank 4 in fixed relation with the receiver 10, but with the shank remaining in a desired angle with respect to the receiver. Thus, once a locking insert is in an interference fit locking engagement with the receiver as shown in FIG. 39, if a rod and closure top have been assembled with the receiver 10, the closure top 18 may be loosened or removed and/or the rod 21 may be adjusted and/or removed and the frictional engagement between the insert 14 and the receiver 10 at the receiver surface 95 will remain locked in place, advantageously maintaining a locked angular position of the shank 4 with respect to the receiver 10. At such time, another rod, such as a deformable rod 21' and cooperating alternative closure top 18' may be loaded onto the already locked-up assembly to result in an alternative assembly.

With reference to FIGS. 40 and 41, there is illustrated an alternative insert 14' that is identical to the insert 14 with the exception that an upper surface 165' is sized and shaped for direct engagement with the alternative closure top 18'. The illustrated rod 21' has the same or similar dimensions as the rod 21, with a cylindrical surface 22', but is made from a material, such as PEEK, that deforms in response to pressure from the closure top, thus making the closure top 18' having the domed surface 200' and central nub 199' a more desirable locking mechanism for keeping the deformable rod 18' in place within the receiver 10. Because the locking of the polyaxial mechanism of the assembly is not dependent on the force of the rod 21' and closure top 18' on the insert 14, any further deformation or eventual loosening of the rod with respect to the closure top 18' or the insert 14 does not affect the secure locking between the insert 14 and the receiver 10 and thus the shank 4 stays frictionally locked against both the insert 14 and the retainer 12, locking the shank 4 in a desired angular position with respect to the receiver 10.

If unlocking of the insert 14 or 14' with respect to the receiver 10 is desired, a tool (not shown) may be inserted into the through apertures 77 below the insert wings 168 and the insert 14 or 14' may be pulled away from the receiver 10. Such a tool may include a piston-like portion for pushing directly on the shank while the insert 14 is pulled away from the receiver. At such time, the shank 4 may be articulated with respect to the receiver 10, and the desired friction fit exists between the retainer 12 and the shank surface 34, so that an adjustable, but non-floppy relationship still exists between the shank 4 and the receiver 10. If further disassembly if the assembly is desired, such is accomplished in reverse order to the procedure described previously herein for the assembly 1.

Returning to FIGS. 37 and 39, the rod 21 is positioned in an open or percutaneous manner in cooperation with the at least two bone screw assemblies 1. The closure structure 18 is then advanced between the arms 62 of each of the receivers 10. The closure structure 18 is rotated, using a tool engaged with the inner drive 196 until a selected pressure is reached at which point the rod 21 engages the U-shaped saddle 173 of the compression insert 14, further pressing the insert spherical surface 178 and stepped shank gripping surfaces 180 against the shank spherical surface 34, the edges 180 penetrating into the spherical surface 34, pressing the shank upper portion 8 into locked frictional engagement with the retainer 12. Specifically, as the closure structure 18 rotates and moves downwardly into the respective receiver 10, the rim 200 engages and penetrates the rod surface 22, the closure structure 18 pressing downwardly against and biasing the rod 21 into compressive engagement with the insert 14 that urges the shank upper portion 8 toward the retainer 12 and into locking engagement therewith at the retainer edge surface 147, the retainer 12 frictionally abutting the receiver surfaces 102 and 103 and pressing outwardly against the receiver cylindrical surfaces 100 and 101. For example, about 80 to about 120 inch pounds of torque on the closure top may be applied for fixing the bone screw shank 6 with respect to the receiver 10. At this time, the retainer inner edge 147 engages and digs into the shank head 8. At this time, the inner tangs 117 are pressed toward the shank head 8 by the insert sub-structure 167 at the surface 167B. As best shown in FIG. 39, due to the position and geometry of the lower skirt surfaces 121 and 122 with respect to the receiver 10 and also due to the location of the inner edge 147, the shank head 8 sits low in the receiver cavity 61, allowing for desirable increased articulation of the shank 4 with respect to the retainer 12 and thus with respect to the receiver 10 as compared to a retainer that does not include such a lower skirt, for example. If disassembly if the assembly 1 is desired, such is accomplished in reverse order to the procedure described previously herein for assembly.

Figure 42:
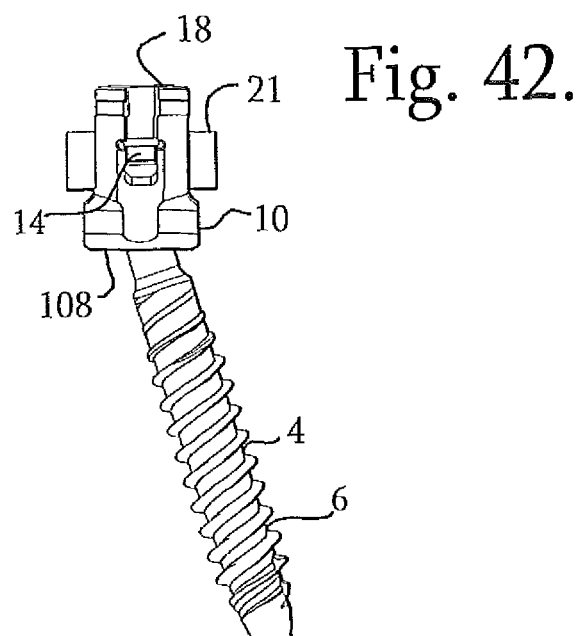
FIG. 42 is a reduced side elevational view of the assembly of FIG. 1, shown fully assembled with the shank disposed at an eighteen degree (cephalad) angle with respect to the receiver.
Figure 43:
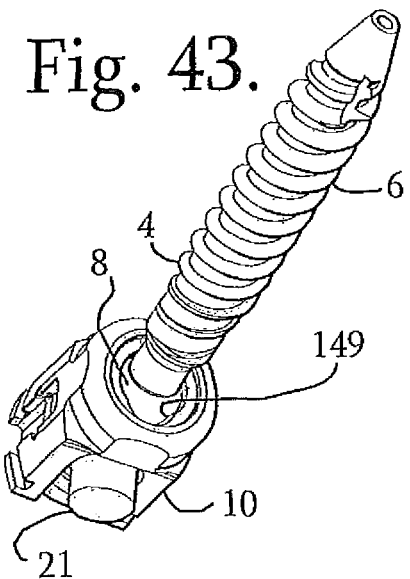
FIG. 43 is a perspective view of the assembly of FIG. 42.
Figure 44:
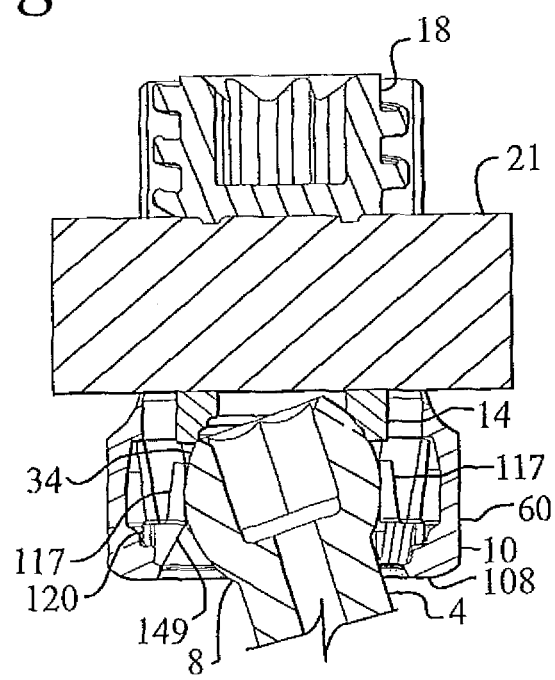
FIG. 44 is an enlarged and partial side elevational view of the assembly of FIG. 42 with portions broken away to show the detail thereof.

With reference to FIGS. 42-47, different angular or articulated positions of the shank 4 with respect to the receiver 10 are shown, some making full use of the slit 148 and adjacent cut-out or cupped surfaces 149 of the retainer 12. For example, compare FIGS. 45-47 wherein the shank 8 is pivoted toward and into engagement with the cupped surfaces 149 as compared to the arrangement shown in FIGS. 42-44, wherein the shank 4 is pivoted in a direction opposite to the retainer slit 148. In FIGS. 42-44 wherein the shank is pivoted in a direction away from the slit 148 and cupped surfaces 149, a resulting shank to receiver articulation is about eighteen degrees (cephalad, for example), which is a desirable degree of articulation in some instances. FIGS. 45-47 show a thirty degree (caudad) or slightly further articulation, possible when the shank head 8 abuts against both surfaces 149 as well as moving slightly into the gap formed by the slit 148.

Figure 48:
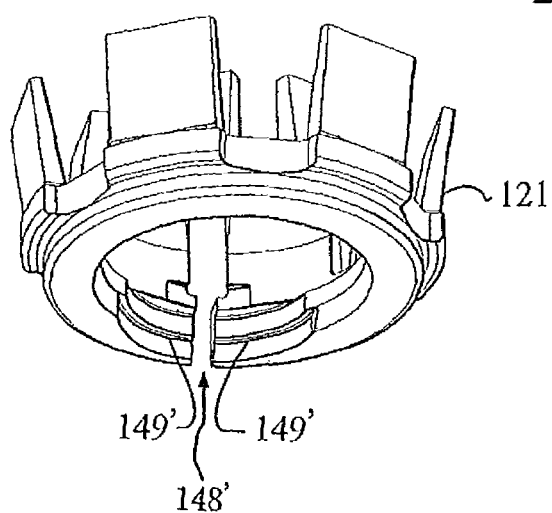
FIG. 48 is an enlarged perspective view of an alternative retainer for use in lieu of the retainer in the assembly of FIG. 1.
Figure 49:
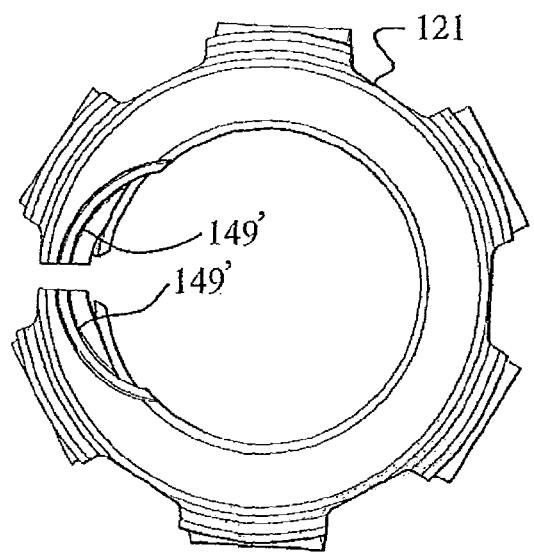
FIG. 49 is a bottom plan view of the retainer of FIG. 48.
Figure 50:
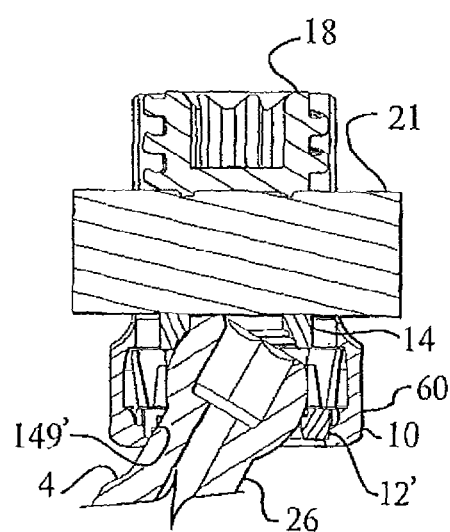
FIG. 50 is an enlarged and partial side elevational view of the assembly of FIG. 1 modified to include the retainer of FIG. 48 in lieu of the retainer shown in FIG. 1, and shown with portions broken away to show the detail thereof.

FIGS. 48-50 illustrate an alternative retainer 12' that includes cupped or cut-out surfaces 149' that are graduated or stepped as compared to the smooth surfaces 149 of the retainer 12. Otherwise, the retainer 12' is identical or substantially similar in form and function to the retainer 12 previously discussed herein. Thus, the retainer 12' fully cooperates with the receiver 10, insert 14, shank 4, rod 21 and closure top 18 in a manner substantially identical to what has been described above with respect to the assembly 1, with the exception that the stepped surfaces 149' grip or dig into the shank 4 at the neck 26 when the shank is pivoted to an about thirty degree articulation with respect to the receiver as shown in FIG. 50. It is foreseen that greater or fewer stepped surfaces may be included along the cupped surface portion 149'.

Figure 51:
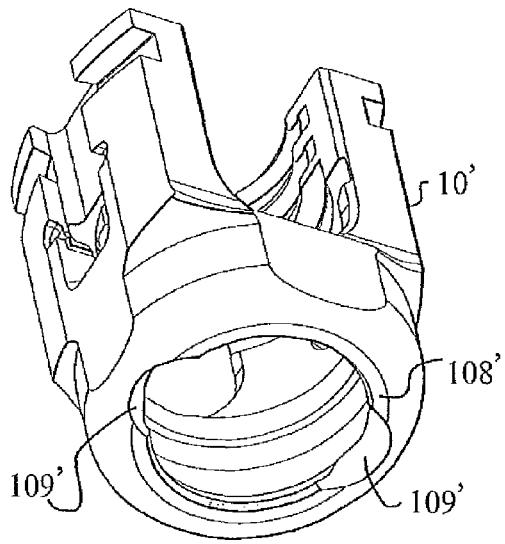
FIG. 51 is an enlarged perspective view of an alternative favored angle receiver of an embodiment according to the invention having opposed lower concave surfaces for cooperating with the retainer of FIG. 1 to allow for up to a forty degree angle of the shank of FIG. 1 with respect to the alternative receiver.
Figure 52:
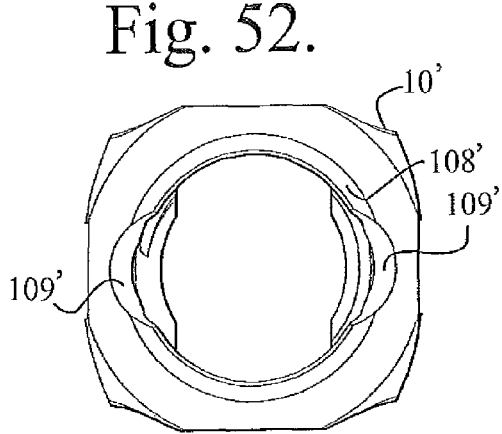
FIG. 52 is an enlarged bottom plan view of the alternative receiver of FIG. 51.
Figure 53:
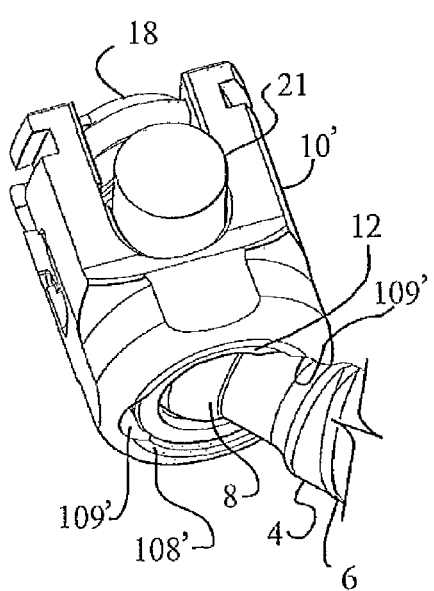
FIG. 53 is an enlarged and partial perspective view of the assembly of FIG. 1 modified to include the alternative receiver of FIG. 51 in lieu of the receiver shown in FIG. 1.
Figure 54:
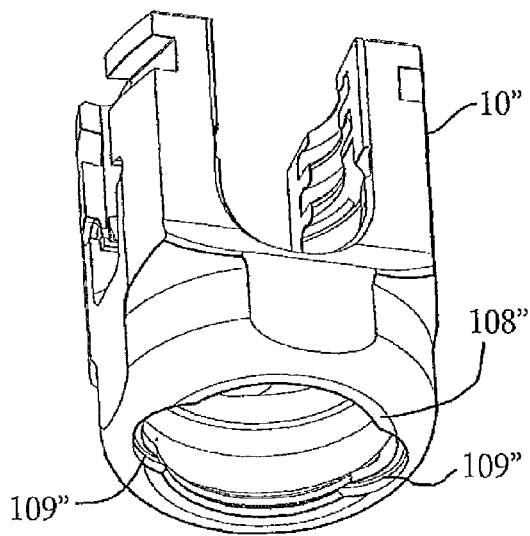
FIG. 54 is a perspective view of another alternative favored angle receiver embodiment according to the invention, similar to the receiver of FIG. 51, but having lower concave stepped surfaces.
Figures 55, 56:
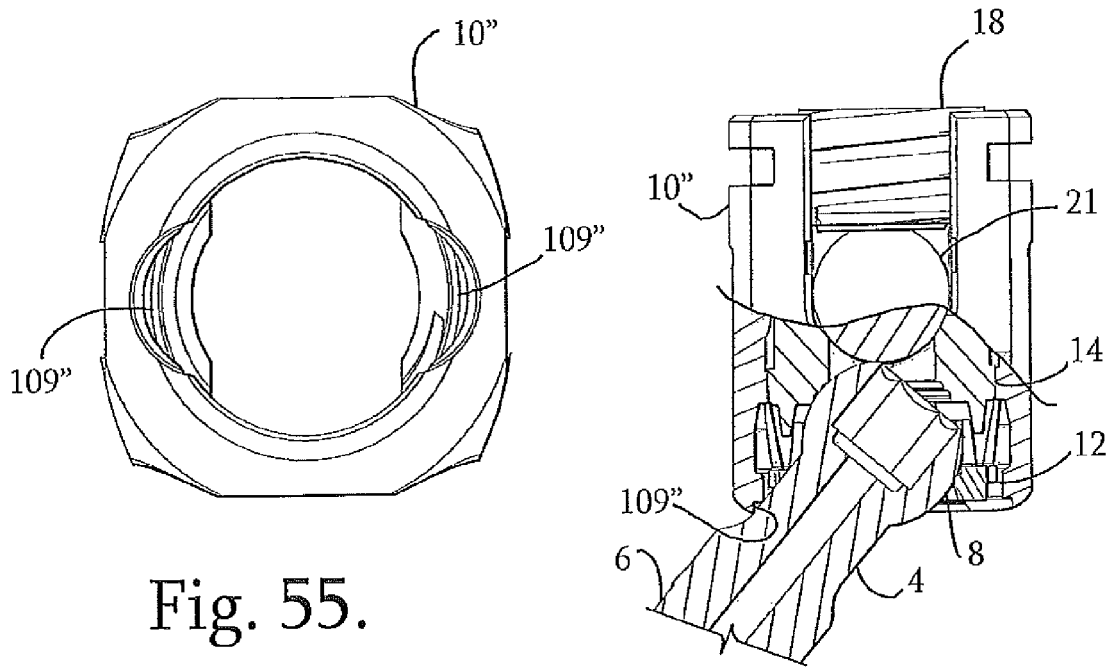
FIG. 55 is an enlarged bottom plan view of the alternative receiver of FIG. 54.
FIG. 56 is an enlarged and partial front elevational view of the assembly of FIG. 1 with portions broken away to show the detail thereof, the assembly modified to include the alternative receiver of FIG. 54 in lieu of the receiver shown in FIG. 1.

FIGS. 51-53 illustrate an alternative receiver 10' that includes a bottom surface 108' further defined by a pair of opposed, concave curved bottom surfaces 109'. Otherwise, the receiver 10' is identical to the receiver 10 described above and thus fully cooperates with the retainer 12, insert 14, shank 4, rod 21 and closure top 18 in a manner substantially identical to what has been described above with respect to the assembly 1. FIGS. 54-56 illustrate another alternative receiver 10" that is substantially similar to the receiver 10', also having opposed, concave curved bottom surfaces 109". The receiver 10" differs from the receiver 10' only in that the surfaces 109" are graduated or stepped. Just like the receiver 10, when the retainer 12 is fully assembled with the receiver 10' or the receiver 10", the retainer 12 is captured within the receiver inner cavity, but is only partially constrained therein, the retainer being rotatable about the central axis of the receiver 10' or 10". Thus, the retainer 12 slit 148 and surfaces 149 can be aligned with either of the receiver concave surfaces 109' or 109". When the retainer surfaces 149 are aligned with one of the surfaces 109' or 109", at least a forty degree angle of articulation between the shank 4 and the receiver 10' or 10" is possible.

An alternative non locking compression insert (not shown) may be used with the shank 4, receiver 10, retainer 12, closure top 18 and rod 21 previously described herein. Such a non-locking insert is substantially similar to the insert 14 previously described herein, having all the features of the insert 14 with the exception of the through apertures 167 and the enlarged interference fit surface 159. Instead, the insert includes either no lower band 159 or a band having a diameter sized to easily slidingly fit within the receiver surface 95 rather than interferingly fit with such surface. Such an alternative non-locking insert may be assembled with the receiver 10, retainer 12, shank 4, rod 21 and closure top 18 in a manner the same as previously described above with respect to the assembly 1, with the exception that the non-locking insert need not be forced downwardly into a locking interference fit with the receiver 10 when the shank 4 is locked in place. If the closure top 18 is loosened or if the closure top 18 and the rod 21 are removed from the assembly 1, the non-locking insert will also shift upwardly in the receiver 10 and the shank 4 will not remain locked with respect to the retainer 12 and the receiver 10. Tooling (not shown) cooperating with the receiver grooves 74 to press downwardly on the wings of such non-locking insert advantageously provides for a temporary locking of the polyaxial mechanism during surgery, if desired by the surgeon.

It is to be understood that while certain forms of the present invention have been illustrated and described herein, it is not to be limited to the specific forms or arrangement of parts described and shown.

What is claimed and desired to be secured by Letters Patent is as follows:

1. A polyaxial bone anchor assembly comprising:
   a) a shank having a body for fixation to a bone and an integral upper portion,
   b) an U-shaped receiver having a top portion and an integral base, the receiver top portion defining an open rod-receiving channel, the integral base defining a cavity communicating with a bottom opening, the bottom opening having at least one concave curved bottom surface, the integral upper portion of the shank positionable within the cavity, and the channel communicating with the cavity;
   c) a retainer positioned within the cavity prior to the shank being loaded and capturing the shank upper portion once loaded, the retainer being in a non-pivotal relationship with respect to the receiver; and wherein the retainer having a cut-out surface being sized and shaped to cooperate with the concave curved bottom surface of the receiver to provide for increased polyaxial motion in at least one direction for the shank with respect to the receiver.

2. The polyaxial bone anchor assembly of claim 1, wherein the receiver further comprises a receiver chamber, partially defined by a ceiling surface disposed substantially perpendicular to the central axis and an inner wall adjacent and substantially perpendicular to the ceiling surface, the inner wall located between a pair of receiver arms and a first planar loading surface and a second planar loading surface, the ceiling surface and the inner wall partially defining an expansion chamber for receiving an expandable open retainer about the shank upper portion.

3. The polyaxial bone anchor assembly of claim 2, wherein the retainer has an outer tapered surface located below and spaced from the receiver first and second planar loading surfaces when in a final locked position.

4. The polyaxial bone anchor assembly of claim 2, further comprising an insert located within the receiver, the insert having an inner lower surface in a friction fit with the shank upper portion during temporary manipulation of the shank with respect to the receiver, the shank upper portion being movable with respect to the insert with some resistance when a force is applied to the shank to pivot the shank with respect to the receiver, the insert being in locked frictional engagement with the shank upper portion when a force is applied on the insert that in turn presses the retainer into the expansion only locked position.

5. The polyaxial bone anchor assembly of claim 4, wherein the insert is spaced from the retainer.

6. The polyaxial bone anchor assembly of claim 4, wherein the receiver has a frusto-conical surface in contact with an outer surface of the insert that presses the insert inner lower surface toward the shank upper portion to create the temporary friction fit.

7. The polyaxial bone anchor assembly of claim 6, wherein the insert has a pair of opposed lower slots.

8. The polyaxial bone anchor assembly of claim 4, wherein the insert has a pair of opposed outer projections and each receiver arm has an aperture for receiving one of the outer projections.

9. The polyaxial bone anchor assembly of claim 8, wherein a receiver wall partially defining one of the apertures for receiving one of the insert outer projections further comprises a lip, the lip engaging one of the insert outer projections.

10. The polyaxial bone anchor assembly of claim 2, wherein the shank is bottom loaded.

11. The polyaxial bone anchor assembly of claim 1 further comprising a longitudinal connecting member, the member comprising:
    a) a cord held in tension at either end of the connecting member;
    b) a first hard sleeve having a body and opposed flanges sized and shaped for placement outside of the receiver, the body further having opposed protruding portions, the tensioned cord received by the sleeve, the sleeve body located within the receiver and seated on an insert;
    c) a closure top rotatably mated with the guide and advancement structure, the sleeve protruding portions engaging both the closure top and the insert; and
    d) a spacer, the spacer receiving the cord therethrough, the spacer located between the first sleeve and one of a second sleeve and an end blocker and set screw combination, the cord being held in tension at one of the second sleeve and the end blocker.

12. The polyaxial bone anchor assembly of claim 11, further comprising a compressible bumper located adjacent the blocker.

13. The polyaxial bone anchor assembly of claim 11, wherein each flange has a planar top surface and the spacer has an extended portion with a planar bottom surface in contact with the flange planar top surface.

14. The polyaxial bone anchor assembly of claim 13, wherein the spacer is engaged with both the first and second sleeves.

* * * * *